(12) United States Patent
Simmons et al.

(10) Patent No.: US 11,998,574 B2
(45) Date of Patent: *Jun. 4, 2024

(54) METHOD AND SYSTEM FOR MODULATING AN INDIVIDUAL'S SKIN MICROBIOME

(71) Applicant: Seed Health, Inc., Venice, CA (US)

(72) Inventors: Sheri Simmons, Brookline, MA (US); Tye Jensen, Telluride, CO (US); Raja Dhir, Venice, CA (US); Joseph E. Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/235,686

(22) Filed: Aug. 18, 2023

(65) Prior Publication Data

US 2024/0024378 A1  Jan. 25, 2024

Related U.S. Application Data

(63) Continuation-in-part of application No. 18/130,946, filed on Apr. 5, 2023, now Pat. No. 11,833,177, which is a continuation-in-part of application No. 18/178,847, filed on Mar. 28, 2023, now Pat. No. 11,839,632, which is a continuation-in-part of application No. 18/087,545, filed on Dec. 22, 2022, now Pat. No. 11,826,388, which is a continuation-in-part of application No. 17/854,422, filed on Jun. 30, 2022, now Pat. No. 11,672,835, which is a continuation-in-part of application No. 17/848,759, filed on Jun. 24, 2022, now Pat. No. 11,642,382, which is a continuation-in-part of application No. 17/835,204, filed on Jun. 8, 2022, now Pat. No. 11,529,379, which is a continuation-in-part of application No. 17/567,295, filed on Jan. 3, 2022, which is a continuation-in-part of application No. 17/337,600, filed on Jun. 3, 2021, now Pat. No. 11,213,552, which is a continuation-in-part of application No. 17/027,953, filed on Sep. 22, 2020, now Pat. No. 11,026,982, which is a continuation-in-part of application No. 16/917,096, filed on Jun. 30, 2020, now Pat. No. 10,940,169, which is a continuation-in-part of application No. 16/782,364, filed on Feb. 5, 2020, now Pat. No. 10,835,560, which is a continuation-in-part of application No. 16/423,375, filed on May 28, 2019, now Pat. No. 10,555,976, which is a continuation of application No. 16/160,336, filed on Oct. 15, 2018, now Pat. No. 10,314,866, which is a continuation of application No. 15/403,823, filed on Jan. 11, 2017, now Pat. No. 10,111,913, application No. 18/235,686 is a continuation-in-part of application No. 18/234,132, filed on Aug. 15, 2023, which is a continuation-in-part of application No. 18/232,980, filed on Aug. 11, 2023, which is a continuation-in-part of application No. 18/232,433, filed on Aug. 10, 2023, which is a continuation-in-part of application No. 18/143,399, filed on May 4, 2023, which is a continuation of application No. 17/893,384, filed on Aug. 23, 2022, (Continued)

(51) Int. Cl.
| | |
|---|---|
| A61K 35/74 | (2015.01) |
| A61K 31/58 | (2006.01) |
| A61K 31/715 | (2006.01) |
| A61K 35/00 | (2006.01) |
| A61K 38/17 | (2006.01) |

(52) U.S. Cl.
CPC .............. *A61K 35/74* (2013.01); *A61K 31/58* (2013.01); *A61K 31/715* (2013.01); *A61K 38/1709* (2013.01); *A61K 38/1758* (2013.01); *A61K 2035/11* (2013.01)

(58) Field of Classification Search
None
See application file for complete search history.

(56) References Cited

U.S. PATENT DOCUMENTS

| | | |
|---|---|---|
| 1,492,600 A | 5/1924 | Laskey |
| 3,178,341 A | 4/1965 | Hamill et al. |

(Continued)

FOREIGN PATENT DOCUMENTS

| | | |
|---|---|---|
| DE | 4412190 | 10/1995 |
| EP | 410696 | 1/1991 |

(Continued)

OTHER PUBLICATIONS

U.S. Appl. No. 17/854,389, filed Jun. 30, 2022, Kovarik.

(Continued)

*Primary Examiner* — Brian Gangle
(74) *Attorney, Agent, or Firm* — Sheridan Ross P.C.

(57) ABSTRACT

Compositions, systems and methods of improving the health of the microbiome of an individual's skin relate to the provision of skin contacting formulations containing beneficial bacteria, postbiotics, metabolites and other microbe components to foster the growth and maintenance of a healthy skin microbiome. One embodiment includes a topical application of *Lactobacillus crispatus* to ameliorate skin barrier damage and inflammation using unique combinations of probiotics, prebiotics, postbiotics, and other skin-beneficial ingredients, effectively treating inflammatory skin diseases, such as atopic dermatitis, psoriasis and acne, through the production of tryptophan metabolites that act as AHR agonists.

20 Claims, 11 Drawing Sheets

Related U.S. Application Data which is a continuation-in-part of application No. 17/694,775, filed on Mar. 15, 2022, which is a continuation-in-part of application No. 17/023,736, filed on Sep. 17, 2020, now Pat. No. 11,419,903, which is a continuation-in-part of application No. 17/011,175, filed on Sep. 3, 2020, now Pat. No. 11,273,187, which is a continuation-in-part of application No. 16/722,117, filed on Dec. 20, 2019, now Pat. No. 10,842,834, which is a continuation-in-part of application No. 16/229,252, filed on Dec. 21, 2018, now Pat. No. 10,512,661, which is a continuation-in-part of application No. 15/392,173, filed on Dec. 28, 2016, now Pat. No. 10,245,288, application No. 18/235,686 is a continuation-in-part of application No. 18/234,544, filed on Aug. 16, 2023, which is a continuation-in-part of application No. 18/103,768, filed on Jan. 31, 2023, which is a continuation-in-part of application No. 17/738,771, filed on May 6, 2022, which is a continuation-in-part of application No. 16/904,056, filed on Jun. 17, 2020, now Pat. No. 11,523,934, which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, application No. 18/235,686, filed on Aug. 18, 2023 is a continuation-in-part of application No. 17/836,079, filed on Jun. 9, 2022, which is a continuation-in-part of application No. 16/884,772, filed on May 27, 2020, now Pat. No. 11,357,722, which is a continuation-in-part of application No. 16/136,950, filed on Sep. 20, 2018, now Pat. No. 10,668,014, which is a continuation of application No. 15/385,278, filed on Dec. 20, 2016, now Pat. No. 10,085,938, application No. 18/235,686, filed on Aug. 18, 2023 is a continuation-in-part of application No. 17/543,992, filed on Dec. 7, 2021, which is a continuation-in-part of application No. 16/804,361, filed on Feb. 28, 2020, now Pat. No. 11,191,665, which is a continuation-in-part of application No. 16/020,433, filed on Jun. 27, 2018, now Pat. No. 10,583,033, which is a continuation-in-part of application No. 15/342,642, filed on Nov. 3, 2016, now Pat. No. 10,010,568, application No. 18/235,686, filed on Aug. 18, 2023 is a continuation-in-part of application No. 16/776,861, filed on Jan. 30, 2020, now Pat. No. 10,864,109, which is a continuation of application No. 16/142,171, filed on Sep. 26, 2018, now Pat. No. 10,548,761, which is a continuation-in-part of application No. 15/395,419, filed on Dec. 30, 2016, now Pat. No. 10,086,018, application No. 18/235,686, filed on Aug. 18, 2023 is a continuation-in-part of application No. 16/426,346, filed on May 30, 2019, now Pat. No. 10,716,815, which is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, which is a continuation-in-part of application No. 15/228,454, filed on Aug. 4, 2016, now Pat. No. 9,585,920, which is a continuation-in-part of application No. 14/954,074, filed on Nov. 30, 2015, now Pat. No. 9,457,077, application No. 18/235,686, filed on Aug. 18, 2023 is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 18/235,686, filed on Aug. 18, 2023 is a continuation-in-part of application No. 16/037,053, filed on Jul. 17, 2018, now abandoned, and a continuation-in-part of application No. 14/752,192, filed on Jun. 26, 2015, now Pat. No. 9,549,842.

(60) Provisional application No. 62/260,906, filed on Nov. 30, 2015, provisional application No. 62/296,186, filed on Feb. 17, 2016, provisional application No. 62/275,341, filed on Jan. 6, 2016, provisional application No. 62/387,405, filed on Dec. 24, 2015, provisional application No. 62/387,404, filed on Dec. 24, 2015, provisional application No. 62/274,550, filed on Jan. 4, 2016, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013.

(56) References Cited

U.S. PATENT DOCUMENTS

| | | |
|---|---|---|
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,568,639 A | 2/1986 | Lew |
| 4,572,832 A | 2/1986 | Kigasawa et al. |
| 4,668,232 A | 5/1987 | Cordes et al. |
| 4,687,841 A | 8/1987 | Spilburg et al. |
| 4,713,243 A | 12/1987 | Schiraldi et al. |
| 4,715,369 A | 12/1987 | Susuki et al. |
| 4,720,486 A | 1/1988 | Spilburg et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,995,555 A | 2/1991 | Woodruff |
| 5,002,970 A | 3/1991 | Eby, III |
| 5,059,189 A | 10/1991 | Cilento et al. |
| 5,064,654 A | 11/1991 | Berner et al. |
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,277,877 A | 1/1994 | Jeffrey et al. |
| 5,284,161 A | 2/1994 | Karell |
| 5,298,258 A | 3/1994 | Akemi et al. |

(56) References Cited

U.S. PATENT DOCUMENTS

| | | |
|---|---|---|
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,518,733 A | 5/1996 | Lamothe et al. |
| 5,578,315 A | 11/1996 | Chien et al. |
| 5,585,098 A | 12/1996 | Coleman |
| 5,614,501 A | 3/1997 | Richards |
| 5,629,003 A | 5/1997 | Horstmann et al. |
| 5,643,603 A | 7/1997 | Bottenberg et al. |
| 5,700,478 A | 12/1997 | Biegajski et al. |
| 5,713,852 A | 2/1998 | Anthony et al. |
| 5,718,702 A | 2/1998 | Edwards |
| 5,719,196 A | 2/1998 | Uhari et al. |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |
| 5,855,872 A | 1/1999 | Libin |
| 5,876,995 A | 3/1999 | Bryan |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya et al. |
| 6,250,307 B1 | 6/2001 | Conrad et al. |
| 6,284,235 B1 | 9/2001 | Foreman et al. |
| 6,287,610 B1 | 9/2001 | Bowling et al. |
| 6,352,711 B1 | 3/2002 | Campbell |
| 6,375,963 B1 | 4/2002 | Repka et al. |
| 6,390,096 B1 | 5/2002 | Conrad et al. |
| 6,431,174 B1 | 8/2002 | Knudson et al. |
| 6,432,986 B2 | 8/2002 | Levin |
| 6,439,238 B1 | 8/2002 | Brenzel et al. |
| 6,453,905 B1 | 9/2002 | Conrad et al. |
| 6,458,380 B1 | 10/2002 | Leaderman |
| 6,458,777 B1 | 10/2002 | Sonis et al. |
| 6,467,485 B1 | 10/2002 | Schmidt |
| 6,502,574 B2 | 1/2003 | Stevens et al. |
| 6,509,028 B2 | 1/2003 | Williams et al. |
| 6,523,542 B2 | 2/2003 | Knudson et al. |
| 6,552,024 B1 | 4/2003 | Chen et al. |
| 6,555,125 B2 | 4/2003 | Campbell |
| 6,569,474 B2 | 5/2003 | Clayton et al. |
| 6,578,580 B2 | 6/2003 | Conrad et al. |
| 6,585,997 B2 | 7/2003 | Moro et al. |
| 6,599,883 B1 | 7/2003 | Romeo et al. |
| 6,620,846 B1 | 9/2003 | Jonn et al. |
| 6,713,463 B2 | 3/2004 | Sonis et al. |
| 6,722,577 B2 | 4/2004 | Dobyns, III |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrell et al. |
| 7,097,853 B1 | 8/2006 | Garbe et al. |
| 7,122,198 B1 | 10/2006 | Singh et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,267,975 B2 | 9/2007 | Strobel et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,353,194 B1 | 4/2008 | Kerker et al. |
| 7,357,891 B2 | 4/2008 | Yang et al. |
| 7,425,292 B2 | 9/2008 | Yang et al. |
| 7,441,559 B2 | 10/2008 | Nelson et al. |
| 7,470,397 B2 | 12/2008 | Meathrel et al. |
| 7,500,484 B2 | 3/2009 | Nelson et al. |
| 7,540,432 B2 | 6/2009 | Majerowski et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan et al. |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,820,420 B2 | 10/2010 | Whitlock |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,862,808 B2 | 1/2011 | Isolauri et al. |
| 7,901,925 B2 | 3/2011 | Bojrab |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,104,478 B2 | 1/2012 | Pflueger et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,383,201 B2 | 2/2013 | Berry et al. |
| 8,420,074 B2 | 4/2013 | Rehberger et al. |
| 8,454,729 B2 | 6/2013 | Mittelmark et al. |
| 8,481,299 B2 | 7/2013 | Gueniche et al. |
| 8,496,914 B2 | 7/2013 | Bonfiglio |
| 8,584,685 B2 | 11/2013 | Kovarik et al. |
| 8,585,588 B2 | 11/2013 | Kovarik et al. |
| 8,591,412 B2 | 11/2013 | Kovarik et al. |
| 8,657,879 B2 | 2/2014 | Shalon et al. |
| 8,685,389 B2 | 4/2014 | Baur et al. |
| 8,701,671 B2 | 4/2014 | Kovarik |
| 8,716,327 B2 | 5/2014 | Zhao et al. |
| 8,757,173 B2 | 6/2014 | Kovarik et al. |
| 8,758,764 B2 | 6/2014 | Masignani et al. |
| 8,815,538 B2 | 8/2014 | Lanzalaco et al. |
| 8,829,165 B2 | 9/2014 | Jackson et al. |
| 8,859,741 B2 | 10/2014 | Jackson et al. |
| 8,865,211 B2 | 10/2014 | Tzannis et al. |
| 8,936,030 B2 | 1/2015 | Kovarik et al. |
| 8,945,839 B2 | 2/2015 | Zhang et al. |
| 8,951,775 B2 | 2/2015 | Castiel et al. |
| 8,999,372 B2 | 4/2015 | Davidson et al. |
| 9,010,340 B2 | 4/2015 | Kovarik et al. |
| 9,011,834 B1 | 4/2015 | McKenzie et al. |
| 9,016,221 B2 | 4/2015 | Brennan et al. |
| 9,017,718 B2 | 4/2015 | Tan et al. |
| 9,028,841 B2 | 5/2015 | Henn et al. |
| 9,044,420 B2 | 6/2015 | Dubensky, Jr. |
| 9,045,547 B2 | 6/2015 | Jackson et al. |
| 9,056,912 B2 | 6/2015 | Grandi et al. |
| 9,095,704 B2 | 8/2015 | McGuire et al. |
| 9,131,884 B2 | 9/2015 | Holmes et al. |
| 9,149,429 B2 | 10/2015 | Kovacs et al. |

(56) References Cited

U.S. PATENT DOCUMENTS

| | | |
|---|---|---|
| 9,234,204 B2 | 1/2016 | Qvit-Raz et al. |
| 9,254,295 B2 | 2/2016 | Adams et al. |
| 9,288,981 B2 | 3/2016 | Gandhi et al. |
| 9,295,682 B2 | 3/2016 | Nunes et al. |
| 9,314,489 B2 | 4/2016 | Kelly et al. |
| 9,408,880 B2 | 8/2016 | Kovarik et al. |
| 9,445,936 B2 | 9/2016 | Kovarik |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 9,795,641 B2 | 10/2017 | Nardelli et al. |
| 9,987,224 B2 | 6/2018 | Kovarik et al. |
| 10,085,938 B2 | 10/2018 | Kovarik et al. |
| 10,086,018 B2 | 10/2018 | Kovarik |
| 10,111,913 B2 | 10/2018 | Kovarik |
| 10,195,273 B2 | 2/2019 | Clube |
| 10,245,288 B2 | 4/2019 | Kovarik |
| 10,314,865 B2 | 6/2019 | Kovarik |
| 10,314,866 B2 | 6/2019 | Kovarik |
| 10,512,661 B2 | 12/2019 | Kovarik |
| 10,548,761 B2 | 2/2020 | Kovarik |
| 10,555,976 B2 | 2/2020 | Kovarik |
| 10,668,014 B2 | 6/2020 | Kovarik et al. |
| 10,683,323 B2 | 6/2020 | Prakash et al. |
| 10,687,975 B2 | 6/2020 | Kovarik et al. |
| 10,716,815 B2 | 7/2020 | Kovarik et al. |
| 10,730,827 B2 | 8/2020 | Wortmann et al. |
| 10,760,075 B2 | 9/2020 | Sommer et al. |
| 10,835,560 B2 | 11/2020 | Kovarik |
| 10,842,834 B2 | 11/2020 | Kovarik |
| 10,864,109 B2 | 12/2020 | Kovarik |
| 10,940,169 B2 | 3/2021 | Kovarik et al. |
| 11,026,982 B2 | 6/2021 | Kovarik |
| 11,083,760 B2 | 8/2021 | Han |
| 11,213,552 B2 | 1/2022 | Kovarik |
| 11,273,187 B2 | 3/2022 | Kovarik |
| 11,357,722 B2 | 6/2022 | Kovarik et al. |
| 11,419,903 B2 | 8/2022 | Kovarik |
| 11,523,934 B2 | 12/2022 | Kovarik et al. |
| 11,529,379 B2 | 12/2022 | Kovarik |
| 11,642,382 B2 | 5/2023 | Kovarik |
| 11,672,835 B2 | 6/2023 | Kovarik |
| 2002/0009520 A1 | 1/2002 | Clayton et al. |
| 2002/0022057 A1 | 2/2002 | Battey et al. |
| 2002/0037310 A1 | 3/2002 | Jonn et al. |
| 2002/0044988 A1 | 4/2002 | Fuchs et al. |
| 2003/0031737 A1 | 2/2003 | Rosenbloom |
| 2003/0062050 A1 | 4/2003 | Schmidt |
| 2003/0083287 A1 | 5/2003 | Burgess et al. |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2003/0206995 A1 | 11/2003 | Bowling et al. |
| 2004/0053352 A1 | 3/2004 | Ouyang et al. |
| 2004/0057962 A1 | 3/2004 | Timmerman |
| 2004/0096569 A1 | 5/2004 | Barkalow et al. |
| 2004/0110111 A1 | 6/2004 | Wasylucha |
| 2004/0115223 A1 | 6/2004 | Follansbee |
| 2004/0120991 A1 | 6/2004 | Gardner et al. |
| 2004/0136923 A1 | 7/2004 | Davidson et al. |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0180080 A1 | 9/2004 | Furasawa et al. |
| 2004/0224007 A1 | 11/2004 | Zhang |
| 2004/0228804 A1 | 11/2004 | Jones et al. |
| 2005/0004417 A1 | 1/2005 | Nelson et al. |
| 2005/0159637 A9 | 1/2005 | Nelson et al. |
| 2005/0118655 A1 | 6/2005 | Weinstock et al. |
| 2005/0137109 A1 | 6/2005 | Quan et al. |
| 2005/0196358 A1 | 9/2005 | Georgiades et al. |
| 2005/0260544 A1 | 11/2005 | Jones et al. |
| 2006/0018843 A1 | 1/2006 | Fine |
| 2006/0035008 A1 | 2/2006 | Virgallito et al. |
| 2006/0064903 A1 | 3/2006 | Tucker |
| 2006/0127330 A1 | 6/2006 | Tsuchida et al. |
| 2006/0188813 A1 | 8/2006 | Shimada |
| 2006/0204591 A1 | 9/2006 | Burrel et al. |
| 2006/0207721 A1 | 9/2006 | Slominski et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis et al. |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0093420 A1 | 4/2007 | Yeomans et al. |
| 2007/0098744 A1 | 5/2007 | Knorr et al. |
| 2007/0102010 A1 | 5/2007 | Lemperle et al. |
| 2007/0122455 A1 | 5/2007 | Myers et al. |
| 2007/0123448 A1 | 5/2007 | Kaplan et al. |
| 2007/0148136 A1 | 6/2007 | Whitlock |
| 2007/0202057 A1 | 8/2007 | Fankhauser et al. |
| 2007/0207955 A1 | 9/2007 | Tanihara et al. |
| 2007/0218114 A1 | 9/2007 | Duggan |
| 2007/0227545 A1 | 10/2007 | Conrad et al. |
| 2007/0231923 A1 | 10/2007 | Cumberland et al. |
| 2007/0246052 A1 | 10/2007 | Hegde et al. |
| 2007/0261701 A1 | 11/2007 | Sanders |
| 2007/0280964 A1 | 12/2007 | Knorr et al. |
| 2007/0293587 A1 | 12/2007 | Haley |
| 2007/0295340 A1 | 12/2007 | Buscemi |
| 2008/0032253 A1 | 2/2008 | Montgomery et al. |
| 2008/0075825 A1 | 3/2008 | Fuisz et al. |
| 2008/0112983 A1 | 5/2008 | Bufe et al. |
| 2008/0242543 A1 | 10/2008 | Banerjee et al. |
| 2008/0267933 A1 | 10/2008 | Ohlson et al. |
| 2008/0286210 A1 | 11/2008 | He et al. |
| 2008/0305089 A1 | 12/2008 | Bufe et al. |
| 2009/0004275 A1 | 1/2009 | Martyn et al. |
| 2009/0098192 A1 | 4/2009 | Fuisz |
| 2009/0130199 A1 | 5/2009 | Kovacs et al. |
| 2009/0148482 A1 | 6/2009 | Peters |
| 2009/0196907 A1 | 8/2009 | Bunick et al. |
| 2009/0196908 A1 | 8/2009 | Lee et al. |
| 2009/0205083 A1 | 8/2009 | Gupta et al. |
| 2010/0029832 A1 | 2/2010 | Pinnavaia et al. |
| 2010/0040593 A1 | 2/2010 | Hedman et al. |
| 2010/0040712 A1 | 2/2010 | Fisher |
| 2010/0081681 A1 | 4/2010 | Blagosklonny |
| 2010/0092406 A1 | 4/2010 | Perez-Davidi et al. |
| 2010/0143447 A1 | 6/2010 | Hansen et al. |
| 2010/0229876 A1 | 9/2010 | Knudson et al. |
| 2010/0247644 A1 | 9/2010 | Domb et al. |
| 2010/0260720 A1 | 10/2010 | Sprenger |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Schobel et al. |
| 2011/0217368 A1 | 9/2011 | Prakash et al. |
| 2011/0230587 A1 | 9/2011 | MacInnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2011/0290694 A1 | 12/2011 | Fuisz et al. |
| 2012/0027786 A1 | 2/2012 | Gupta et al. |
| 2012/0029832 A1 | 2/2012 | Dodgson |
| 2012/0039806 A1 | 2/2012 | Lahoud et al. |
| 2012/0058094 A1 | 3/2012 | Blaser et al. |
| 2012/0128597 A1 | 5/2012 | Peters et al. |
| 2012/0142548 A1 | 6/2012 | Corsi et al. |
| 2012/0148629 A1 | 6/2012 | Holvoet et al. |
| 2012/0276143 A1 | 11/2012 | O'Mahony et al. |
| 2012/0276149 A1 | 11/2012 | Littman et al. |
| 2012/0276525 A1 | 11/2012 | Kovarik et al. |
| 2012/0283269 A1 | 11/2012 | Blagosklonny et al. |
| 2012/0294822 A1 | 11/2012 | Russo et al. |

(56) References Cited

U.S. PATENT DOCUMENTS

| | | |
|---|---|---|
| 2012/0301452 A1 | 11/2012 | Gueniche et al. |
| 2013/0059815 A1 | 3/2013 | Fournell et al. |
| 2013/0087155 A1 | 4/2013 | Hedman et al. |
| 2013/0157876 A1 | 6/2013 | Lynch et al. |
| 2013/0225440 A1 | 8/2013 | Friedman et al. |
| 2013/0236488 A1 | 9/2013 | Dashper et al. |
| 2013/0252983 A1 | 9/2013 | Cerione et al. |
| 2013/0259834 A1 | 10/2013 | Klaenhammer et al. |
| 2013/0310416 A1 | 11/2013 | Blagosklonny |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon et al. |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0125550 A1 | 5/2014 | Kaneko et al. |
| 2014/0154290 A1 | 6/2014 | Peters et al. |
| 2014/0199266 A1 | 7/2014 | Park et al. |
| 2014/0255351 A1 | 9/2014 | Berstad et al. |
| 2014/0271867 A1 | 9/2014 | Myers et al. |
| 2014/0294915 A1 | 10/2014 | Barreca et al. |
| 2014/0296139 A1 | 10/2014 | Cohen et al. |
| 2014/0333003 A1 | 11/2014 | Allen et al. |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0017143 A1 | 1/2015 | Holvoet et al. |
| 2015/0017227 A1 | 1/2015 | Kim et al. |
| 2015/0038594 A1 | 2/2015 | Borges et al. |
| 2015/0045546 A1 | 2/2015 | Siksnys et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0093473 A1 | 4/2015 | Barrangou et al. |
| 2015/0132263 A1 | 5/2015 | Liu et al. |
| 2015/0147371 A1 | 5/2015 | Kovarik et al. |
| 2015/0150792 A1 | 6/2015 | Klingman |
| 2015/0166641 A1 | 6/2015 | Goodman et al. |
| 2015/0190435 A1 | 7/2015 | Henn et al. |
| 2015/0202136 A1 | 7/2015 | Lanzalaco et al. |
| 2015/0216917 A1 | 8/2015 | Jones et al. |
| 2015/0224072 A1 | 8/2015 | Pellikaan |
| 2015/0252358 A1 | 9/2015 | Maeder et al. |
| 2015/0259728 A1 | 9/2015 | Cutliffe et al. |
| 2015/0329555 A1 | 11/2015 | Liras et al. |
| 2015/0329875 A1 | 11/2015 | Gregory et al. |
| 2015/0352023 A1 | 12/2015 | Berg et al. |
| 2015/0353901 A1 | 12/2015 | Liu et al. |
| 2015/0361436 A1 | 12/2015 | Hitchcock et al. |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Akins et al. |
| 2016/0069921 A1 | 3/2016 | Holmes et al. |
| 2016/0089315 A1 | 3/2016 | Kleinberg et al. |
| 2016/0089405 A1 | 3/2016 | Lue |
| 2016/0095316 A1 | 4/2016 | Goodman et al. |
| 2016/0120915 A1 | 5/2016 | Blaser et al. |
| 2016/0122806 A1 | 5/2016 | Amini et al. |
| 2016/0151427 A1 | 6/2016 | Whitlock et al. |
| 2016/0151428 A1 | 6/2016 | Bryan |
| 2016/0158294 A1 | 6/2016 | Von Maltzahn et al. |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206564 A1 | 7/2016 | Trachtman |
| 2016/0206666 A1 | 7/2016 | Falb et al. |
| 2016/0206668 A1 | 7/2016 | Kort et al. |
| 2016/0213702 A1 | 7/2016 | Von Maltzahn et al. |
| 2016/0243132 A1 | 8/2016 | Adams et al. |
| 2016/0271106 A1 | 9/2016 | Shi et al. |
| 2016/0271189 A1 | 9/2016 | Cutcliffe et al. |
| 2016/0311913 A1 | 10/2016 | Sun et al. |
| 2016/0314281 A1 | 10/2016 | Apte et al. |
| 2016/0354416 A1 | 12/2016 | Gajewski et al. |
| 2016/0374941 A1 | 12/2016 | Barreca et al. |
| 2017/0014341 A1 | 1/2017 | Armer et al. |
| 2017/0020932 A1 | 1/2017 | Cutcliffe et al. |
| 2017/0027914 A1 | 2/2017 | Qi |
| 2017/0042860 A1 | 2/2017 | Kashyap et al. |
| 2017/0042924 A1 | 2/2017 | Otsuka et al. |
| 2017/0071986 A1 | 3/2017 | Kovarik et al. |
| 2017/0079947 A1 | 3/2017 | Richards |
| 2017/0100328 A1 | 4/2017 | Kovarik et al. |
| 2017/0232043 A1 | 8/2017 | Falb et al. |
| 2017/0240625 A1 | 8/2017 | Zeller et al. |
| 2017/0246269 A1 | 8/2017 | Hajishengallis et al. |
| 2017/0298115 A1 | 10/2017 | Loomis et al. |
| 2017/0312232 A1 | 11/2017 | Vitetta et al. |
| 2017/0342141 A1 | 11/2017 | Russo et al. |
| 2017/0348303 A1 | 12/2017 | Bosse et al. |
| 2018/0000878 A1 | 1/2018 | Goodman et al. |
| 2018/0015131 A1 | 1/2018 | Gajewski et al. |
| 2018/0016647 A1 | 1/2018 | Van Sinderen et al. |
| 2018/0092899 A1 | 4/2018 | Liu et al. |
| 2018/0100169 A1 | 4/2018 | Soucaille et al. |
| 2018/0110795 A1 | 4/2018 | Frias-Lopez |
| 2018/0111984 A1 | 5/2018 | Bigal et al. |
| 2018/0127490 A1 | 5/2018 | Bigal et al. |
| 2018/0134772 A1 | 5/2018 | Sharma et al. |
| 2018/0140698 A1 | 5/2018 | Clube et al. |
| 2018/0207165 A1 | 7/2018 | Harmsen et al. |
| 2018/0235987 A1 | 8/2018 | Von Maltzahn et al. |
| 2018/0258100 A1 | 9/2018 | Gregory et al. |
| 2018/0296582 A1 | 10/2018 | von Maltzahn et al. |
| 2018/0303658 A1 | 10/2018 | Kovarik et al. |
| 2018/0312851 A1 | 11/2018 | Falb et al. |
| 2018/0326008 A1 | 11/2018 | Schreiber et al. |
| 2018/0371405 A1 | 12/2018 | Barrangou et al. |
| 2019/0000815 A1 | 1/2019 | Melin |
| 2019/0018012 A1 | 1/2019 | Kovarik |
| 2019/0059314 A1 | 2/2019 | Aharoni et al. |
| 2019/0290605 A1 | 6/2019 | Rasochova et al. |
| 2019/0120960 A1 | 7/2019 | Konradi et al. |
| 2019/0262298 A1 | 8/2019 | Kanthasamy et al. |
| 2019/0315642 A1 | 10/2019 | Parsley et al. |
| 2019/0388471 A1 | 12/2019 | June et al. |
| 2019/0390284 A1 | 12/2019 | Kim |
| 2020/0009185 A1 | 1/2020 | Shin et al. |
| 2020/0009268 A1 | 1/2020 | Scholz |
| 2020/0032224 A1 | 1/2020 | Schaefer et al. |
| 2020/0148642 A1 | 5/2020 | Konradi et al. |
| 2020/0155447 A1 | 5/2020 | Edwards |
| 2020/0188454 A1 | 6/2020 | Slykerman |
| 2020/0190494 A1 | 6/2020 | Hou et al. |
| 2020/0197215 A1 | 6/2020 | Kovarik et al. |
| 2020/0199555 A1 | 6/2020 | Zhang |
| 2021/0169954 A1 | 6/2021 | Balani et al. |
| 2021/0198665 A1 | 7/2021 | Sommer et al. |
| 2021/0308028 A1 | 10/2021 | Yang et al. |
| 2021/0321756 A1 | 10/2021 | McLaughlin et al. |
| 2021/0361560 A1 | 11/2021 | Krueger et al. |
| 2021/0386659 A1 | 12/2021 | Kim |
| 2022/0000760 A1 | 1/2022 | Rasochova |
| 2022/0023259 A1 | 1/2022 | Davidson et al. |
| 2022/0031590 A1 | 2/2022 | Pesaro et al. |
| 2022/0031767 A1 | 2/2022 | Duportet et al. |
| 2022/0071877 A1 | 3/2022 | Zenobia et al. |
| 2022/0088001 A1 | 3/2022 | Kovarik et al. |
| 2022/0088090 A1 | 3/2022 | Lobacki et al. |
| 2022/0118031 A1 | 4/2022 | Kovarik |
| 2022/0135987 A1 | 5/2022 | Leveau et al. |
| 2022/0193150 A1 | 6/2022 | Kovarik |

(56) References Cited

U.S. PATENT DOCUMENTS

| | | | |
|---|---|---|---|
| 2022/0193157 | A1 | 6/2022 | Zimmerman et al. |
| 2022/0257410 | A1 | 8/2022 | Kovarik |
| 2022/0296500 | A1 | 9/2022 | Kovarik |
| 2022/0331374 | A1 | 10/2022 | Richter et al. |
| 2022/0339208 | A1 | 10/2022 | Abel et al. |
| 2022/0387402 | A1 | 12/2022 | Aspnes et al. |
| 2023/0040879 | A1 | 2/2023 | Kovarik |
| 2023/0106721 | A1 | 4/2023 | Catania et al. |
| 2023/0131201 | A1 | 4/2023 | Kovarik |
| 2023/0165706 | A1 | 6/2023 | Tye et al. |
| 2023/0218682 | A1 | 7/2023 | Tye et al. |
| 2023/0241129 | A1 | 8/2023 | Simmons et al. |

FOREIGN PATENT DOCUMENTS

| | | |
|---|---|---|
| JP | S56-100714 | 8/1981 |
| WO | WO 98/22097 | 5/1998 |
| WO | WO 2006/007922 | 1/2006 |
| WO | WO 2006/015445 | 2/2006 |
| WO | WO 2006/133879 | 12/2006 |
| WO | WO 2008/088426 | 7/2008 |
| WO | WO 2008/097890 | 8/2008 |
| WO | WO 2009/052421 | 4/2009 |
| WO | WO 2010/041143 | 4/2010 |
| WO | WO 2011/020780 | 2/2011 |
| WO | WO 2011/029701 | 3/2011 |
| WO | WO 2013/026000 | 2/2013 |
| WO | WO 2013/107750 | 7/2013 |
| WO | WO 2013/182038 | 12/2013 |
| WO | WO 2014/103488 | 7/2014 |
| WO | WO 2014/152338 | 9/2014 |
| WO | WO 2014/182632 | 11/2014 |
| WO | WO 2014/196913 | 12/2014 |
| WO | WO 2015/069682 | 5/2015 |
| WO | WO 2016/070151 | 5/2016 |
| WO | WO 2017/211753 | 12/2017 |
| WO | WO 2019/067621 | 4/2019 |
| WO | WO 2022/187274 | 9/2022 |

OTHER PUBLICATIONS

U.S. Appl. No. 18/143,399, filed May 4, 2023, Kovarik.
U.S. Appl. No. 18/232,433, filed Aug. 10, 2023, Simmons et al.
U.S. Appl. No. 18/232,980, filed Aug. 11, 2023, Kovarik.
U.S. Appl. No. 18/234,132, filed Aug. 15, 2023, Simmons et al.
U.S. Appl. No. 18/234,544, filed Aug. 16, 2023, Simmons et al.
"Oral Cavity," University of Michigan Medical School, Date Unknown, retrieved Nov. 20, 2019 from https://histology.medicine.umich.edu/resources/oral-cavity, 5 pages.
"The structure behind the simplicity of CRISPR/Cas9," The Scinder at Medium.com, Dec. 23, 2015, retrieved from https://medium.com/the-scinder/the-structure-behind-the-simplicity-of-crispr-cas9-6f8cb60695c4, 8 pages.
Abruzzo et al., "Influence of Lactobacillus Biosurfactants on Skin Permeation of Hydrocortisone," Pharmaceutics, vol. 13, No. 6, May 2021, 14 pages.
Agrawal et al., "Technique to Control pH in Vicinity of Biodegrading PLA-PGA Implants," Journal of Biomedical Materials Research, vol. 38, No. 2, 1997, pp. 105-114.
Aguilar-Toala et al., "Potential role of natural bioactive peptides for development of cosmeceutical skin products," Peptides, vol. 122, No. 170170, Dec. 2019, 8 pages. Abstract only.
Athanasiou et al., "In Vitro Degradation and Release Characteristics of Biodegradable Implants Containing Trypsin Inhibitor," Clinical Orthopaedics and Related Research, vol. 315, Jun. 1995, pp. 272-281. Abstract only.
Auerbach et al., "Angiogenesis assays: Problems and pitfalls," Cancer and Metastasis Reviews, vol. 19, 2000, pp. 167-172.
Basseri et al., "Antibiotics for the Treatment of Irritable Bowel Syndrome," Gastroenterology & Hepatology, vol. 7, No. 7, Jul. 2011, pp. 455-493.
Baud et al., "Microbial diversity in the vaginal microbiota and its link to pregnancy outcomes," Scientific Reports, vol. 13, No. 9061, 2023, 12 pages.
Blumen et al., "Radiofrequency Ablation for the Treatment of Mild to Moderate Obstructive Sleep Apnea," The Laryngoscope, vol. 112, No. 11, Nov. 2002, pp. 2086-2092.
Bocheva et al., "Protective Role of Melatonin and Its Metabolites in Skin Aging," International Journal of Molecular Sciences, vol. 23, No. 1238, Jan. 2022, 23 pages.
Brietzke et al., "Injection Snoreplasty: Extended Follow-Up and New Objective Data," Otolaryngology—Head and Neck Surgery, vol. 128, No. 5, May 2003, pp. 605-615. Abstract only.
Brietzke et al., "Injection Snoreplasty: How to Treat Snoring without All the Pain and Expense," Otolaryngology—Head and Neck Surgery, vol. 124, No. 5, May 2001, pp. 503-510. Abstract only.
Brietzke et al., "Injection Snoreplasty: Investigation of Alternative Sclerotherapy Agents," Otolaryngology—Head and Neck Surgery, vol. 130, No. 1, Jan. 2004, pp. 47-57. Abstract only.
Brown et al., "Improving the Diagnosis of Vulvovaginitis: Perspectives to Align Practice, Guidelines, and Awareness," Population Health Management, vol. 23, Suppl. 1, 2020, pp. S3- S12.
Catalano et al., "Additional palatal implants for refractory snoring," Otolaryngology—Head and Neck Surgery, vol. 137, No. 1, Jul. 2007, pp. 105-109. Abstract only.
Charulatha et al., "Influence of different crosslinking treatments on the physical properties of collagen membranes," Biomaterials, vol. 24, No. 5, 2003, pp. 759-767.
Chen et al., "Targeting Aldehyde Dehydrogenase 2: New Therapeutic Opportunities," Physiological Reviews, vol. 94, No. 1, 2014, 65 pages.
Choi et al., "Therapeutic Effects of Cold-Pressed Perilla Oil Mainly Consisting of Linolenic acid, Oleic Acid and Linoleic Acid on UV-Induced Photoaging in NHDF Cells and SKH-1 Hairless Mice," Molecules, vol. 25, Feb. 2020, 19 pages.
Chuang et al., "Effects of exogenous crosslinking on in vitro tensile and compressive moduli of lumbar intervertebral discs," Clinical Biomechanics, vol. 22, No. 1, Jan. 2007, pp. 14-20. Abstract only.
Courage, "Fiber-Famished Gut Microbes Linked to Poor Health," Scientific American, Mar. 23, 2015, retrieved from https://www.scientificamerican.com/article/fiber-famished-gut-microbes-linked-to-poor-health, 10 pages.
De Seta et al., "The Vaginal Community State Types Microbiome-Immune Network as Key Factor for Bacterial Vaginosis and Aerobic Vaginitis," Frontiers in Microbiology, vol. 10, No. 2451, Oct. 30, 2019, 8 pages.
Ding et al., "Resveratrol accelerates wound healing by inducing M2 macrophage polarisation in diabetic mice," Pharmaceutical Biology, vol. 60, No. 1, 2022, pp. 2328-2337.
Douam et al., "Genetic Dissection of the Host Tropism of Human-Tropic Pathogens," Annual Review of Genetics, vol. 49, 2015, pp. 21-45.
Dunkley et al., "A role for CD4+ T cells from orally immunized rats in enhanced clearance of Pseudomonas aeruginosa from the lung," Immunology, vol. 83, 1994, pp. 362-369.
Earlia et al., "GC/MS Analysis of Fatty Acids on Pliek U Oil and Its Pharmacological Study by Molecular Docking to Filaggrin as a Drug Candidate in Atopic Dermatitis Treatment," Scientific World Journal, Nov. 2019, 7 pages.
Enomoto et al., "Koji amazake Maintains Water Content in the Left Cheek Skin of Healthy Adults: A Randomized, Double-Blind, Placebo-Controlled, Parallel-Group, Comparative Trial," Clinical, Cosmetic and Investigational Dermatology, vol. 15, Jul. 2022, pp. 1283-1291.
Farhadihosseinabadi et al., "The in vivo effect of Lacto-N-neotetraose (LNnT) on the expression of type 2 immune response involved genes in the wound healing process," Scientific Reports, vol. 10, No. 997, Jan. 2020, 11 pages.
Fischer et al., "[Radiofrequency ablation of the soft palate (somnoplasty). A new method in the treatment of habitual and obstructive snoring].," HNO, vol. 48, No. 1, Jan. 2000, pp. 33-40. Abstract only.
Friedman et al., "Patient Selection and Efficacy of Pillar Implant Technique for Treatment of Snoring and Obstructive Sleep Apnea/

(56) References Cited

OTHER PUBLICATIONS

Hypopnea Syndrome," Otolaryngology—Head and Neck Surgery, vol. 134, No. 2, Feb. 2006, pp. 187-196. Abstract only.
Gajer et al., "Temporal Dynamics of the Human Vaginal Microbiota," Science Translational Medicine, vol. 4, No. 132, May 2, 2012, 21 pages.
Gratzer et al., "Control of pH Alters the Type of Cross-linking Produced by 1-Ethyl-3-(3-Dimethylaminopropyl)-Carbodiimide (EDC) Treatment of Acellular Matrix Vascular Grafts," Journal of Biomedical Materials Research, vol. 58, No. 2, 2001, pp. 172-179.
Guilleminault et al., "Snoring (I). Daytime sleepiness in regular heavy snorers," Chest, vol. 99, 1991, pp. 40-48.
Guilleminault et al., "The sleep apnea syndromes," Annual Review of Medicine, vol. 27, Feb. 1976, pp. 465-484. First Page Only.
Gura, "Systems for Identifying New Drugs Are Often Faulty," Science, vol. 278, No. 5340, Nov. 7, 1997, pp. 1041-1042.
Han et al., "Proanthocyanidin: A natural crosslinking reagent for stabilizing collagen matrices," Journal of Biomedical Materials Research, vol. 65A, No. 1, Apr. 2003, pp. 118-124. Abstract only.
Hedman et al., "Exogenous Cross-Linking Increases the Stability of Spinal Motion Segments," Spine, vol. 31, No. 15, Jul. 2006, pp. E480-E485. Abstract only.
Hennessy et al., "Statins as next generation anti-microbials: Is there potential for repurposing?," Antimicrob. Agents Chemother., Jun. 20, 2016, 46 pages.
Hildebrand et al., "Vaginitis," NCBI Bookshelf, Updated Nov. 14, 2022, 12 pages.
Hoffmann et al., "Glutaraldehyde and oxidised dextran as crosslinker reagents for chitosan-based scaffolds for cartilage tissue engineering," Journal of Materials Science: Materials in Medicine, vol. 20, Mar. 2009, pp. 1495-1503.
Hunter et al., "Meniscal material properties are minimally affected by matrix stabilization using glutaraldehyde and glycation with ribose," Journal of Orthopaedic Research, vol. 23, 2005, pp. 555-561.
Jain, "Barriers to Drug Delivery in Solid Tumors," Scientific American, Jul. 1994, pp. 58-65.
Kilkkinen et al., "Use of antimicrobials and risk of type 1 diabetes in a population-based mother-child cohort," Diabetologia, vol. 49, 2006, pp. 66-70.
Kim et al., "Kaempferol tetrasaccharides restore skin atrophy via PDK1 inhibition in human skin cells and tissues: Bench and clinical studies," Biomedicine & Pharmacotherapy, vol. 156, No. 113864, Dec. 2022, 13 pages.
Kim et al., "Spermidine-induced recovery of human dermal structure and barrier function by skin microbiome," Communications Biology, vol. 4, No. 231, 2021, 11 pages.
Kim et al., "β-Glucogallin isolated from Fusidium coccineum and its enhancement of skin barrier effects," Applied Biological Chemistry, vol. 63, No. 77, Nov. 2020, 7 pages.
Kimoto et al., "New Lactococcus Strain with Immunnomodulatory Activity: Enhancement of Th1-Type Immune Response," Microbiol. Immunol., vol. 48, No. 2, 2004, pp. 75-82.
Klapperich et al., "A novel biocompatible adhesive incorporating plant-derived monomers," Journal of Biomedical Materials Research Part A, vol. 91, No. 2, pp. 378-374.
Klingspor et al., "Research Article: Enterococcus faecium NCIMB 10415 Modulates Epithelial Integrity, Heat Shock Protein, and Proinflammatory Cytokine Response in Intestinal Cells," Mediators of Inflammation, vol. 2015, No. 304149 ,2015, 12 pages.
Ko, "Effects of Glycogen on Ceramide Production in Cultured Human Keratinocytes via Acid Sphingomyelinase Activation," Master's Thesis Submitted to the Graduate School of Public Health (Korea), 2018, 53 pages.
Komuro et al., "Sphingomyelin maintains the cutaneous barrier via regulation of the STAT3 pathway," The FASEB Journal, vol. 36, No. 4, Apr. 2022, 17 pages.
Kurek-Gorecka et al., "Bee Products in Dermatology and Skin Care," Molecules, vol. 25, No. 3, Jan. 2020, 17 pages.

Kyriakopoulos et al., "Taurine and N-Bromotaurine in Topical Treatment of Psoriasis," Advances in Experimental Medicine and Biology, vol. 1370, 2022, pp. 99-111. Abstract only.
Laneri et al., "Plant cell culture extract of Cirsium eriophorum with skin pore refiner activity by modulating sebum production and inflammatory response," Phytotherapy Research, vol. 35, No. 1, Jan. 2021, pp. 530-540.
Lebeer et al., "Selective targeting of skin pathobionts and inflammation with topically applied lactobacilli," Cell Reports Medicine, vol. 3, No. 2, Feb. 2022, 22 pages.
Lenger et al., "D-mannose vs other agents for recurrent urinary tract infection prevention in adult women: a systematic review and meta-analysis," American Journal of Obstetrics and Gynecology, vol. 223, No. 2, Aug. 2020, pp. 265.e1-265.e13.
Lew et al., "Bioactives from probiotics for dermal health: functions and benefits," Journal of Applied Microbiology, vol. 114, No. 5, May 2013, pp. 1241-1253.
Lewis et al., "Vaginal Microbiome and Its Relationship to Behavior, Sexual Health, and Sexually Transmitted Diseases," Obstetrics & Gynecology, vol. 129, No. 4, Apr. 2017, pp. 643-654.
Liu et al., "Activation of aryl hydrocarbon receptor in Langerhans cells by a microbial metabolite of tryptophan negatively regulates skin inflammation," Journal of Dermatological Science, vol. 100, No. 3, Dec. 2020, pp. 192-200. Abstract only.
Liu et al., "The potential of *Streptococcus thermophiles* (TCI633) in the anti-aging," Journal of Cosmetic Dermatology, vol. 21, No. 6, Jun. 2022, pp. 2635-2647.
Ma et al., "The vaginal microbiome: rethinking health and diseases," Annual Review of Microbiology, vol. 66, 2012, pp. 371-389.
Mach et al., "Endurance exercise and gut microbiota: A review," Journal of Sport and Health Science, vol. 6, No. 2, Jun. 2017, pp. 179-197.
Mahdiani et al., "Protective effect of luteolin against chemical and natural toxicants by targeting NF-κB pathway," Biofactors, vol. 48, No. 4, Jul. 2022, pp. 744-762. Abstract only.
Malaguarnera et al., "Bifidobacterium longum with Fructo-Oligosaccharides in Patients with Non Alcoholic Steatohepatitis," Digestive Diseases and Sciences, vol. 57, 2012, pp. 545-553.
Matsui et al., "Biological Rhythms in the Skin," International Journal of Molecular Sciences, vol. 17, No. 801, May 2016, 15 pages.
Mayrovitz et al., "Assessing Potential Circadian, Diurnal, and Ultradian Variations in Skin Biophysical Properties," Cureus, vol. 13, No. 9, Sep. 2021, 18 pages.
McFadzean, "Exercise can help modulate human gut microbiota," Honors Thesis Submitted to the University of Colorado Department of Evolutionary Biology, Apr. 7, 2014, 34 pages.
Nakai et al., "Effects of Topical N-Acetylcysteine on Skin Hydration/Transepidermal Water Loss in Healthy Volunteers and Atopic Dermatitis Patients," Annals of Dermatology, vol. 27, No. 4, Aug. 2015, pp. 450-451.
Neves et al., "Efficacy of a topical serum containing L-ascorbic acid, neohesperidin, pycnogenol, tocopherol, and hyaluronic acid in relation to skin aging signs," Journal of Cosmetic Dermatology, vol. 21, No. 10, Oct. 2022, pp. 4462-4469. Abstract only.
Nisbet et al., "Clinical and in vitro evaluation of new anti-redness cosmetic products in subjects with winter xerosis and sensitive skin," International Journal of Cosmetic Science, vol. 41, No. 6, Dec. 2019, pp. 534-547.
Norton et al., "The immune response to Lactococcus lactis: Implications for its use as a vaccine delivery vehicle," FEMS Microbiology Letters, vol. 120, No. 3, Jul. 15, 1994, pp. 249-256. Abstract only.
O'Hanlon et al., "In vaginal fluid, bacteria associated with bacterial vaginosis can be suppressed with lactic acid but not hydrogen peroxide," BMC Infectious Diseases, vol. 11, No. 200, 2011, 8 pages.
Paladine et al., "Vaginitis: Diagnosis and Treatment," American Family Physician, vol. 97, No. 5, Mar. 1, 2018, pp. 321-329.
Park et al., "Fermented black rice and blueberry with Lactobacillus plantarum MG4221 improve UVB-induced skin injury," Food and Agricultural Immunology, vol. 32, No. 1, 2021, pp. 499-515.

(56) References Cited

OTHER PUBLICATIONS

Pinto et al., "Plantaricin A synthesized by Lactobacillus plantarum induces in vitro proliferation and migration of human keratinocytes and increases the expression of TGF-β1, FGF7, VEGF-A and IL-8 genes," Peptides, vol. 32, No. 9, Sep. 2011, pp. 1815-1824. Abstract only.

Ragusa et al., "Spirulina for Skin Care: A Bright Blue Future," Cosmetics, vol. 8, No. 1, Jan. 2021, 19 pages.

Ravel et al., "Vaginal microbiome of reproductive-age women," PNAS, vol. 108, Suppl. 1, Mar. 15, 2011, pp. 4680-4687.

Repa et al., "Mucosal co-application of lactic acid bacteria and allergen induces counter-regulatory immune responses in a murine model of birch pollen allergy," Vaccine, vol. 22, No. 1, 2003, pp. 87-95. Abstract only.

Scaglione et al., "Considerations on D-mannose Mechanism of Action and Consequent Classification of Marketed Healthcare Products," Frontiers In Pharmacology, vol. 12, No. 636377, Mar. 2, 2021, 7 pages.

Schaeffer et al., "Effect of Carbohydrates on Adherence of *Escherichia coli* to Human Urinary Tract Epithelial Cells," Infection and Immunity, vol. 30, No. 2, Nov. 1980, pp. 531-537.

Sevilla et al., "Revisiting the role of melatonin in human melanocyte physiology: A skin context perspective," Journal of Pineal Research, vol. 72, No. 3, Apr. 2022, 23 pages.

Sheikh, "Is Crispr the Next Antibiotic?," The New York Times, Oct. 29, 2019, retrieved from https://www.nytimes.com/2019/28/health/crispr-genetics-antibiotic-resistance.html, 2 pages.

Shen et al., "Propionibacterium acnes related anti-inflammation and skin hydration activities of madecassoside, a pentacyclic triterpene saponin from Centella asiatica," Bioscience, Biotechnology, and Biochemistry, vol. 83, No. 3, 2019, pp. 561-568.

Sheweita et al., "Preclinical studies on melanogenesis proteins using a resveratrol-nanoformula as a skin whitener," International Journal of Biological Macromolecules, vol. 223, Part A, Dec. 2022, pp. 870-881. Abstract only.

Simmering et al., "The Increase in Hospitalizations for Urinary Tract Infections and the Associated Costs in the United States, 1998-2011," Open Forum Infectious Diseases, vol. 4, No. 1, Feb. 24, 2017, 7 pages.

Sivieri et al., "Lactobacillus acidophilus CRL 1014 improved "gut health" in the SHIME reactor," BMC Gastroenterology, vol. 13, No. 100, 2013, 9 pages.

Spinler et al., "Human-derived probiotic Lactobacillus reuteri demonstrate antimicrobial activities targeting diverse enteric bacterial pathogens," Anaerobe, vol. 14, Feb. 29, 2008, pp. 166-171.

Sporn et al., "Chemoprevention of cancer," Carcinogenesis, vol. 21, No. 3, 2000, pp. 525-530.

Thongaram et al., "Human milk oligosaccharide consumption by probiotic and human-associated bifidobacteria and lactobacilli," Journal of Dairy Science, vol. 100, No. 10, Oct. 2017, pp. 7825-7833.

Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins, vol. 11, No. 6, May 2019, 12 pages.

Van Der Veer et al., "Comparative genomics of human Lactobacillus crispatus isolates reveals genes for glycosylation and glycogen degradation: implications for in vivo dominance of the vaginal microbiota," Microbiome, vol. 7, No. 49, 2019, 14 pages.

Van Hemert et al., "Migraine associated with gastrointestinal disorders: review of the literature and clinical implications," Frontiers in Neurology, vol. 5, No. 241, Nov. 2014, 4 pages.

Wan et al., "Luteolin-7-glucoside Promotes Human Epidermal Stem Cell Proliferation by Upregulating β-Catenin, c-Myc, and Cyclin Expression," Stem Cells International, vol. 2019, No. 1575480, Jun. 2019, 10 pages.

Wilbie et al., "Delivery Aspects of CRISPR/Cas for in Vivo Genome Editing," Accounts of Chemical Research, vol. 52, 2019, pp. 1555-1564.

Yamamura et al., "Oral mucosal adhesive Film containing local anesthetics: in vitro and clinical evaluation." Journal of Biomedical Materials Research, Fall 1998, vol. 43, No. 3, pp. 313-317. Abstract only.

Yatsuhashi et al., "Effects of Glycogen on Ceramide Production in Cultured Human Keratinocytes via Acid Sphingomyelinase Activation," Journal of Applied Glycoscience, vol. 68, 2021, pp. 41-46.

Yosipovitch et al., "Time-Dependent Variations of the Skin Barrier Function in Humans: Transepidermal Water Loss, Stratum Corneum Hydration, Skin Surface pH, and Skin Temperature," Journal of INvestigative Dermatology, vol. 110, No. 1, Jan. 1998, pp. 20-23.

Zahedi et al., "Development of plasma functionalized polypropylene wound dressing for betaine hydrochloride controlled drug delivery on diabetic wounds," Scientific Reports, vol. 11, No. 9641, 2021, 18 pages.

Zhao et al., "Microbiome-generated amyloid and potential impact on amyloidogenesis in Alzheimer's disease (AD)," Journal of Nature and Science, vol. 1, No. 7, 2015, pp. 1-5.

Zhou et al., "Nicotinamide Mononucleotide Combined With Lactobacillus fermentum TKSN041 Reduces the Photoaging Damage in Murine Skin by Activating AMPK Signaling Pathway," Frontiers in Pharmacology, vol. 12, No. 643089, Mar. 2021, 17 pages.

Official Action for U.S. Appl. No. 14/574,517 dated Jan. 6, 2016, 13 pages.

Notice of Allowance for U.S. Appl. No. 14/574,517, dated Apr. 15, 2016, 8 pages.

Corrected Notice of Allowance for U.S. Appl. No. 14/574,517, dated Jul. 7, 2016, 2 pages.

Official Action for U.S. Appl. No. 14/954,074, dated Jun. 30, 2016, 4 pages.

Notice of Allowance for U.S. Appl. No. 14/954,074, dated Jul. 20, 2016, 7 pages.

Official Action for U.S. Appl. No. 15/270,034, dated Apr. 6, 2017, 5 pages.

Notice of Allowance for U.S. Appl. No. 15/270,034, dated May 5, 2017, 7 pages.

Official Action for U.S. Appl. No. 15/392,173, dated Jan. 22, 2018, 8 pages.

Official Action for U.S. Appl. No. 15/392,173, dated Jul. 6, 2018, 13 pages.

Notice of Allowance for U.S. Appl. No. 15/392,173, dated Dec. 5, 2018, 8 pages.

Official Action for U.S. Appl. No. 16/229,252, dated Feb. 28, 2019, 5 pages.

Notice of Allowance for U.S. Appl. No. 16/229,252, dated Aug. 21, 2019, 7 pages.

Official Action for U.S. Appl. No. 16/722,117, dated Feb. 20, 2020, 6 pages.

Notice of Allowance for U.S. Appl. No. 16/722,117, dated Jul. 30, 2020, 8 pages.

Official Action for U.S. Appl. No. 17/011,175, dated Jun. 17, 2021, 9 pages.

Notice of Allowance for U.S. Appl. No. 17/011,175, dated Nov. 5, 2021, 8 pages.

Official Action for U.S. Appl. No. 17/023,736, dated Nov. 10, 2021, 7 pages.

Notice of Allowance for U.S. Appl. No. 17/023,736, dated Apr. 14, 2022, 8 pages.

Official Action for U.S. Appl. No. 17/893,384, dated May 9, 2023, 8 pages.

Notice of Allowance for U.S. Appl. No. 17/893,384, dated Aug. 23, 2023, 7 pages.

Official Action for U.S. Appl. No. 15/403,823, dated Oct. 30, 2017, 7 pages.

Official Action for U.S. Appl. No. 15/403,823, dated May 25, 2018, 9 pages.

Notice of Allowance for U.S. Appl. No. 15/403,823, dated Jun. 28, 2018, 9 pages.

Official Action for U.S. Appl. No. 16/160,336, dated Nov. 27, 2018, 6 pages.

Notice of Allowance for U.S. Appl. No. 16/160,336, dated Feb. 15, 2019, 7 pages.

(56) References Cited

OTHER PUBLICATIONS

Official Action for U.S. Appl. No. 16/423,375, dated Jul. 3, 2019, 6 pages.
Notice of Allowance for U.S. Appl. No. 16/423,375, dated Oct. 16, 2019, 8 pages.
Official Action for U.S. Appl. No. 16/782,364, dated Apr. 9, 2020, 5 pages.
Notice of Allowance for U.S. Appl. No. 16/782,364, dated Jul. 27, 2020, 7 pages.
Official Action for U.S. Appl. No. 16/917,096, dated Jul. 31, 2020, 5 pages.
Official Action for U.S. Appl. No. 16/617,096, dated Oct. 19, 2020, 8 pages.
Official Action for U.S. Appl. No. 17/027,953, dated Jan. 29, 2021, 5 pages.
Notice of Allowance for U.S. Appl. No. 17/027,953, dated Apr. 19, 2021, 8 pages.
Official Action for U.S. Appl. No. 17/337,600, dated Jul. 6, 2021, 5 pages.
Notice of Allowance for U.S. Appl. No. 17/337,600, dated Sep. 9, 2021, 7 pages.
Official Action for U.S. Appl. No. 17/835,204, dated Jul. 28, 2022, 6 pages.
Notice of Allowance for U.S. Appl. No. 17/835,204, dated Aug. 24, 2022, 7 pages.
Official Action for U.S. Appl. No. 17/848,759, dated Sep. 14, 2022, 6 pages.
Notice of Allowance for U.S. Appl. No. 17/848,759, dated Dec. 29, 2022, 7 pages.
Corrected Notice of Allowance for U.S. Appl. No. 17/848,759, dated Jan. 12, 2023, 4 pages.
Official Action for U.S. Appl. No. 17/854,422, dated Sep. 28, 2022, 7 pages.
Official Action for U.S. Appl. No. 17/854,422, dated Jan. 10, 2023, 6 pages.
Notice of Allowance for U.S. Appl. No. 17/854,422, dated Feb. 17, 2023, 7 pages.
Official Action for U.S. Appl. No. 18/087,545, dated May 24, 2023, 5 pages.
Notice of Allowance for U.S. Appl. No. 18/087,545, dated Jul. 26, 2023, 7 pages.
Official Action for U.S. Appl. No. 18/178,847, dated Jul. 13, 2023, 8 pages.
Notice of Allowance for U.S. Appl. No. 18/178,847, dated Aug. 8, 2023, 8 pages.
Official Action for U.S. Appl. No. 18/130,946, dated Jun. 30, 2023, 6 pages.
Notice of Allowance for U.S. Appl. No. 18/130,946, dated Aug. 1, 2023, 8 pages.
Official Action for U.S. Appl. No. 15/228,454, dated Sep. 23, 2016, 11 pages.
Notice of Allowance for U.S. Appl. No. 15/228,454, dated Jan. 23, 2017, 7 pages.
Official Action for U.S. Appl. No. 15/437,976, dated Mar. 29, 2017, 8 pages.
Notice of Allowance for U.S. Appl. No. 15/437,976, dated Jul. 12, 2017, 7 pages.
Official Action for U.S. Appl. No. 15/639,767, dated Aug. 14, 2017, 11 pages.
Official Action for U.S. Appl. No. 15/639,767, dated Sep. 27, 2018, 13 pages.
Notice of Allowance for U.S. Appl. No. 15/369,767, dated Feb. 15, 2019, 8 pages.
Official Action for U.S. Appl. No. 16/426,346, dated Aug. 2, 2019, 10 pages.
Official Action for U.S. Appl. No. 16/426,346, dated Jan. 13, 2020, 7 pages.
Notice of Allowance for U.S. Appl. No. 16/426,346, dated Mar. 25, 2020, 7 pages.
Official Action for U.S. Appl. No. 13/367,052, dated Jan. 16, 2014, 8 pages.
Notice of Allowance for U.S. Appl. No. 13/367,052, dated Feb. 24, 2014, 5 pages.
Official Action for U.S. Appl. No. 14/225,503, dated May 4, 2016, 6 pages.
Notice of Allowance for U.S. Appl. No. 14/225,503, dated Jul. 20, 2016, 5 pages.
Official Action for U.S. Appl. No. 14/752,192, dated Jul. 8, 2016, 8 pages.
Notice of Allowance for U.S. Appl. No. 14/752,192, dated Sep. 16, 2016, 5 pages.
Official Action for U.S. Appl. No. 15/378,425, dated May 15, 2019, 82 pages.
Official Action for U.S. Appl. No. 15/378,425, dated Oct. 2, 2019, 41 pages.
Official Action for U.S. Appl. No. 15/378,425, dated Jul. 15, 2020, 21 pages.
Official Action for U.S. Appl. No. 15/378,425, dated Nov. 10, 2020, 29 pages.
Official Action for U.S. Appl. No. 15/385,278, dated Oct. 30, 2017, 23 pages.
Official Action for U.S. Appl. No. 15/385,278, dated Apr. 13, 2018, 18 pages.
Notice of Allowance for U.S. Appl. No. 15/385,278, dated May 31, 2018, 10 pages.
Official Action for U.S. Appl. No. 16/136,950, dated Nov. 25, 2019, 11 pages.
Official Action for U.S. Appl. No. 16/136,950, dated Jan. 31, 2020, 8 pages.
Official Action for U.S. Appl. No. 16/884,772, dated Sep. 30, 2021, 8 pages.
Notice of Allowance for U.S. Appl. No. 16/884,772, dated Feb. 22, 2022, 7 pages.
Official Action for U.S. Appl. No. 15/384,716, dated Nov. 1, 2017, 31 pages.
Notice of Allowance for U.S. Appl. No. 15/384,716, dated Apr. 2, 2018, 9 pages.
Official Action for U.S. Appl. No. 15/983,250, dated Mar. 5, 2019, 23 pages.
Official Action for U.S. Appl. No. 15/983,250, dated May 24, 2019, 21 pages.
Official Action for U.S. Appl. No. 15/983,250, dated Jan. 14, 2020, 8 pages.
Notice of Allowance for U.S. Appl. No. 15/983,250, dated Feb. 14, 2020, 8 pages.
Official Action for U.S. Appl. No. 16/904,056, dated Dec. 6, 2021, 12 pages.
Official Action for U.S. Appl. No. 16/904,056, dated May 17, 2022, 11 pages.
Notice of Allowance for U.S. Appl. No. 16/904,056, dated Aug. 11, 2022, 8 pages.
Corrected Notice of Allowance for U.S. Appl. No. 16/904,056, dated Aug. 24, 2022, 6 pages.
Official Action for U.S. Appl. No. 18/103,768, dated Apr. 25, 2023, 5 pages.
Notice of Allowance for U.S. Appl. No. 18/103,768, dated Aug. 1, 2023, 7 pages.
Official Action for U.S. Appl. No. 18/143,399, dated Sep. 7, 2023, 8 pages.

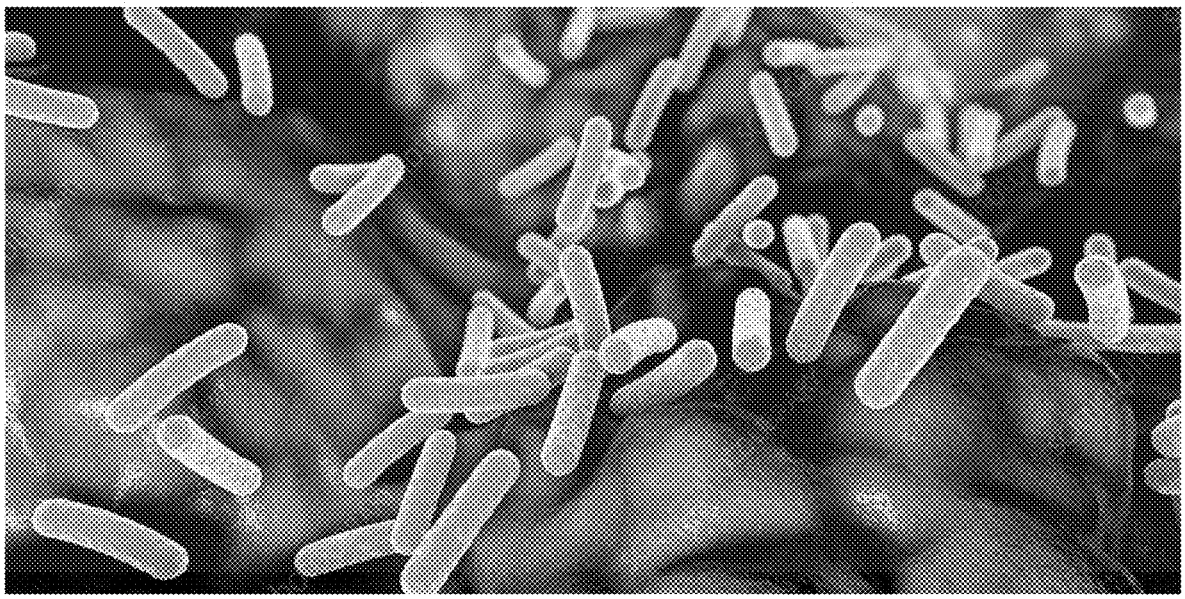
Fig. 1. - *Faecalibacterium prausnitzii*
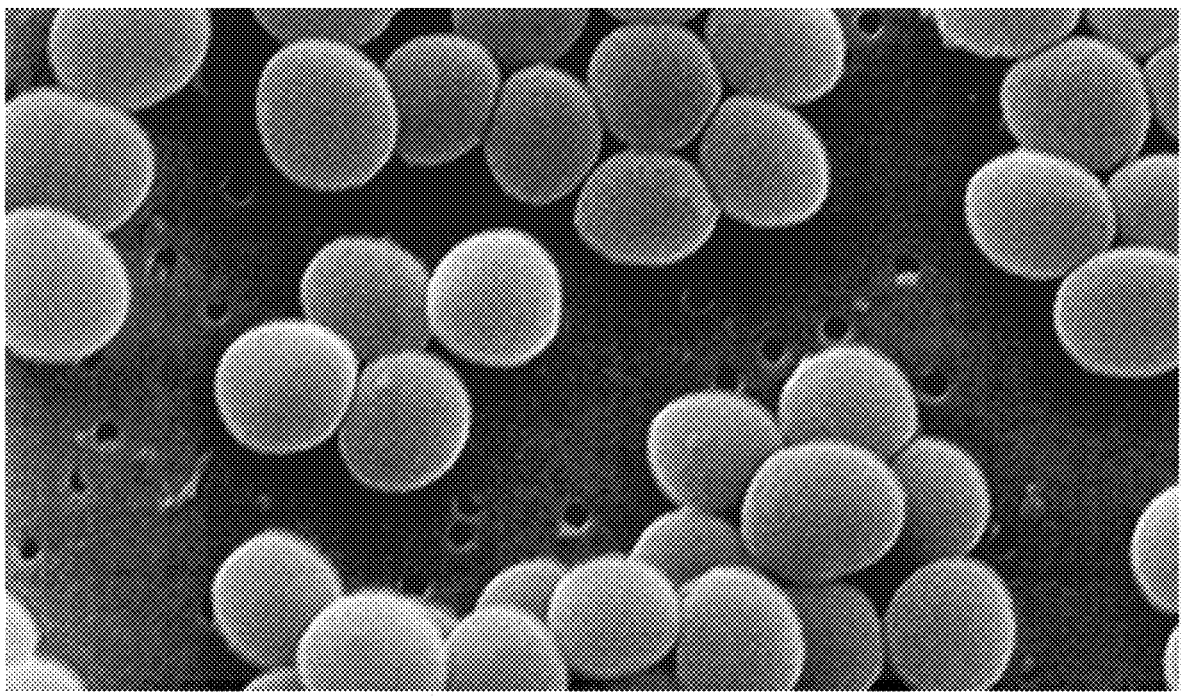
Fig. 2 - *Akkermansia muciniphila*

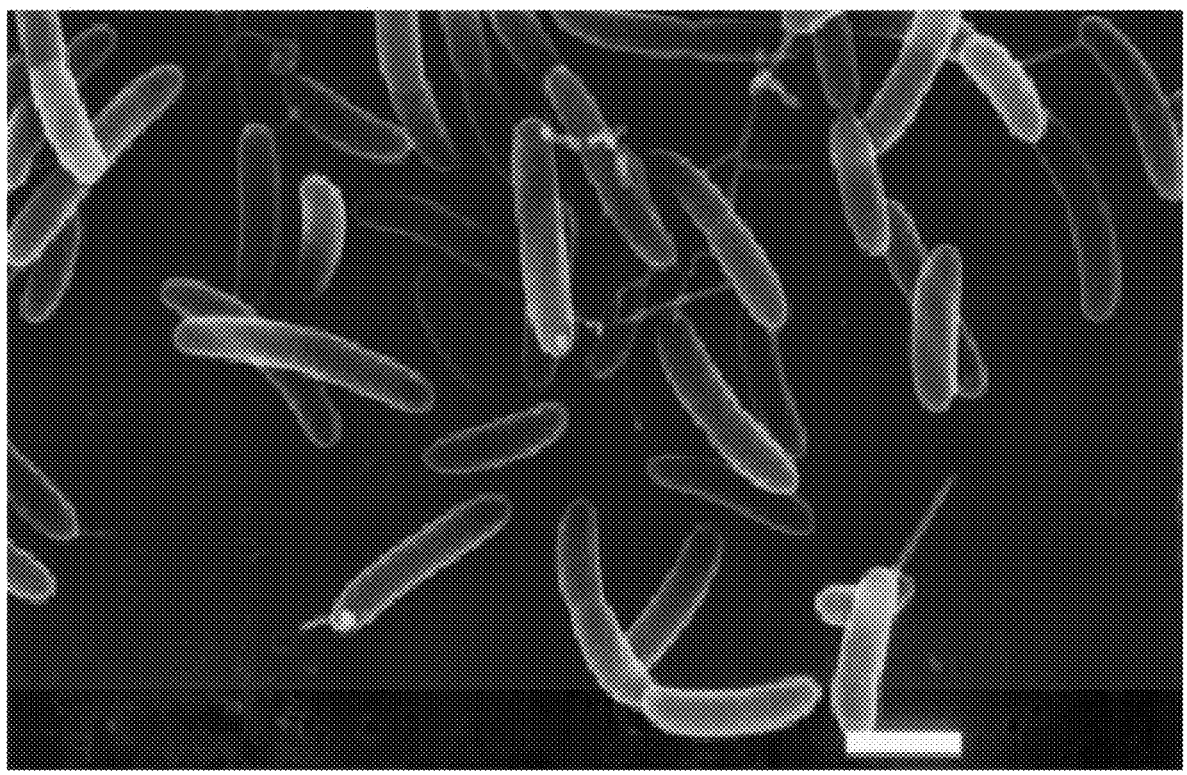
Fig. 3 - Roseburia

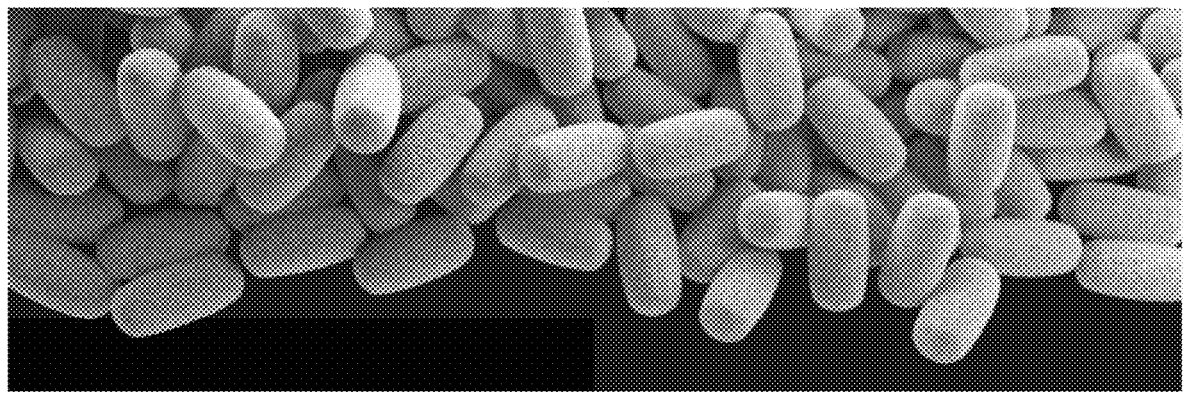
Fig. 4 - *Clostridium*
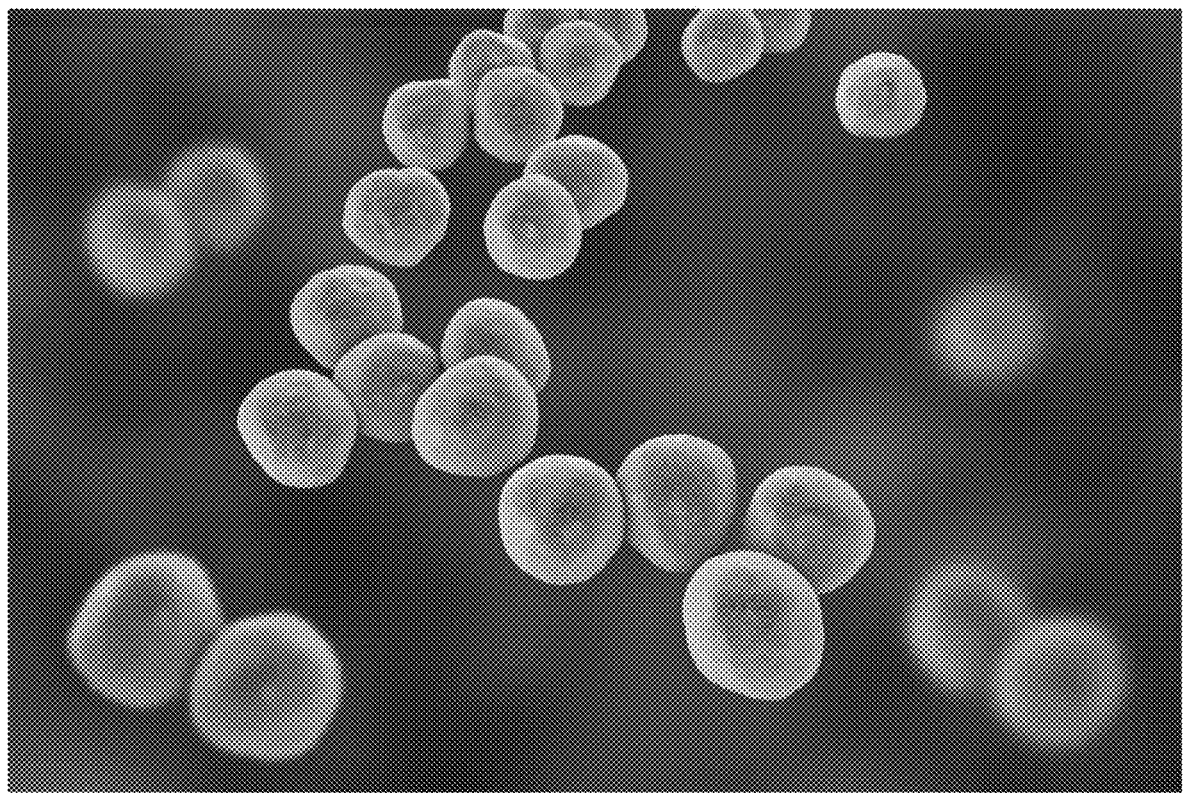
Fig. 5 - *Veillonella*

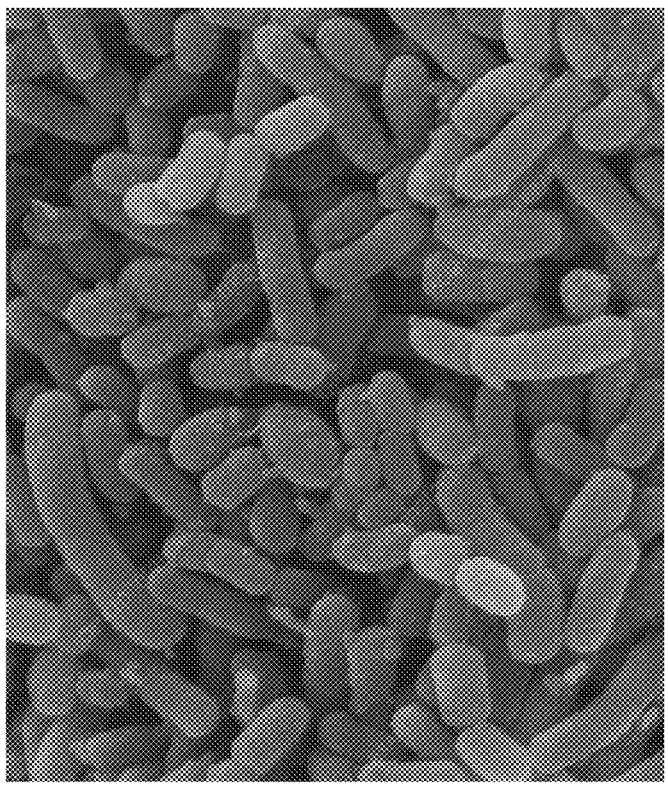
Fig. 6 – *Prevotella*
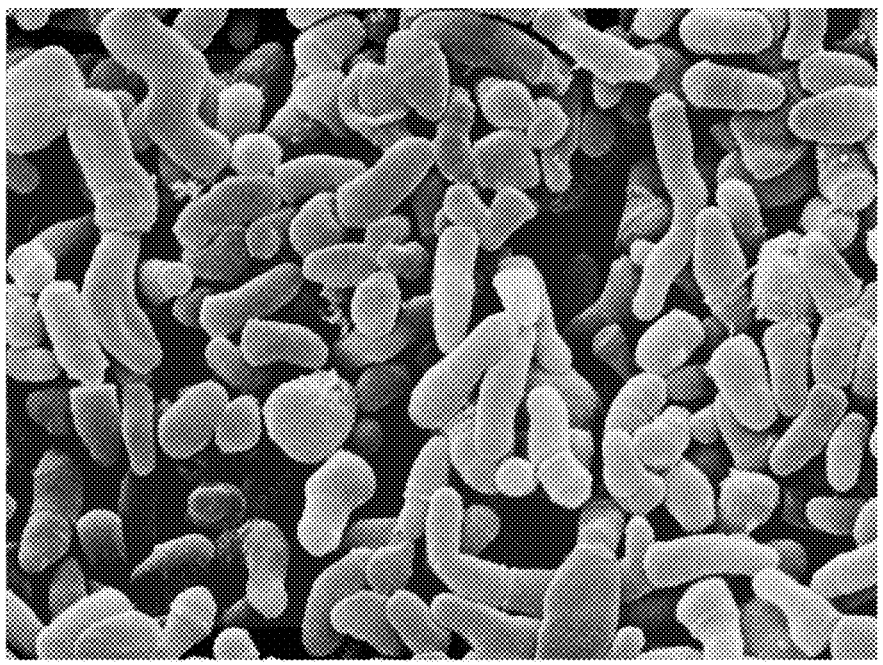
Fig. 7 – *Propionibacterium*

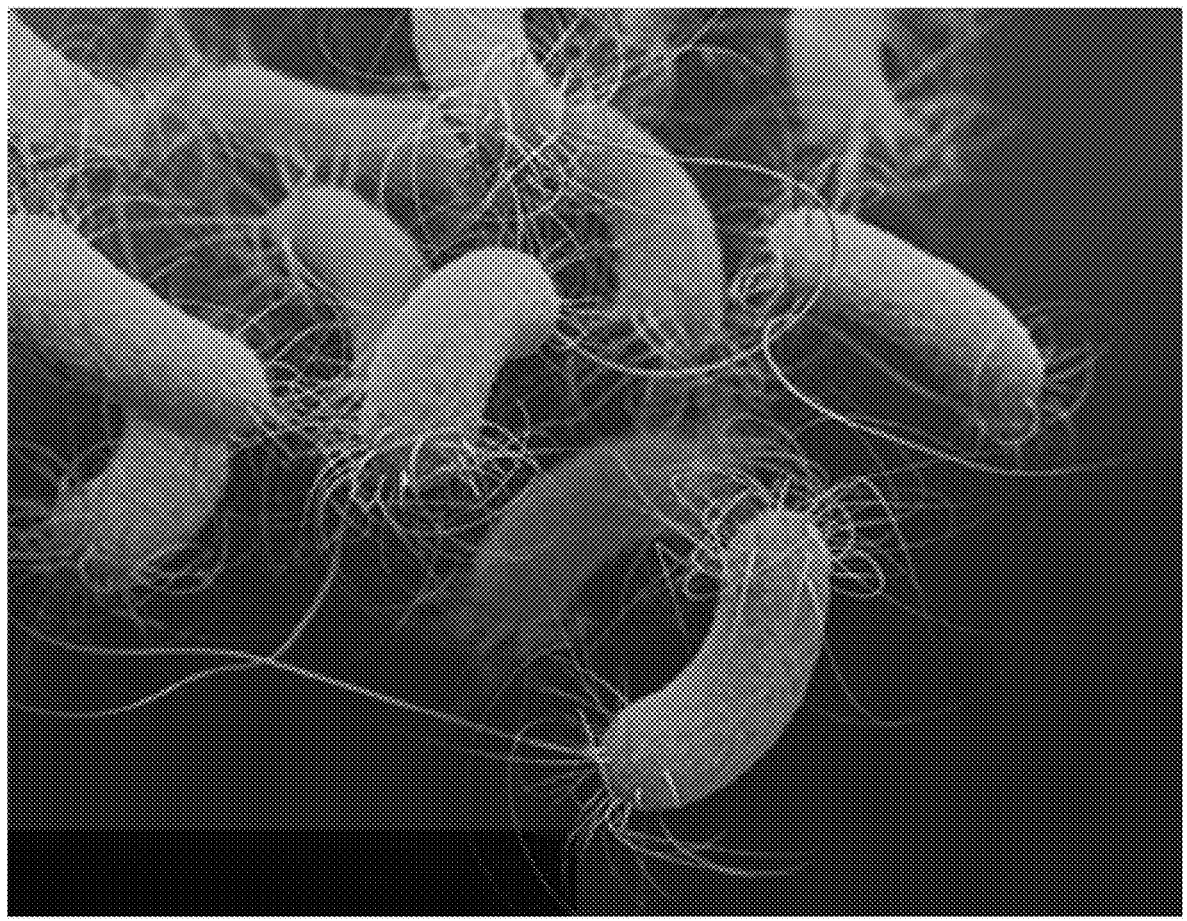
Fig. 8 - *Pseudomonas aeuroginosa*

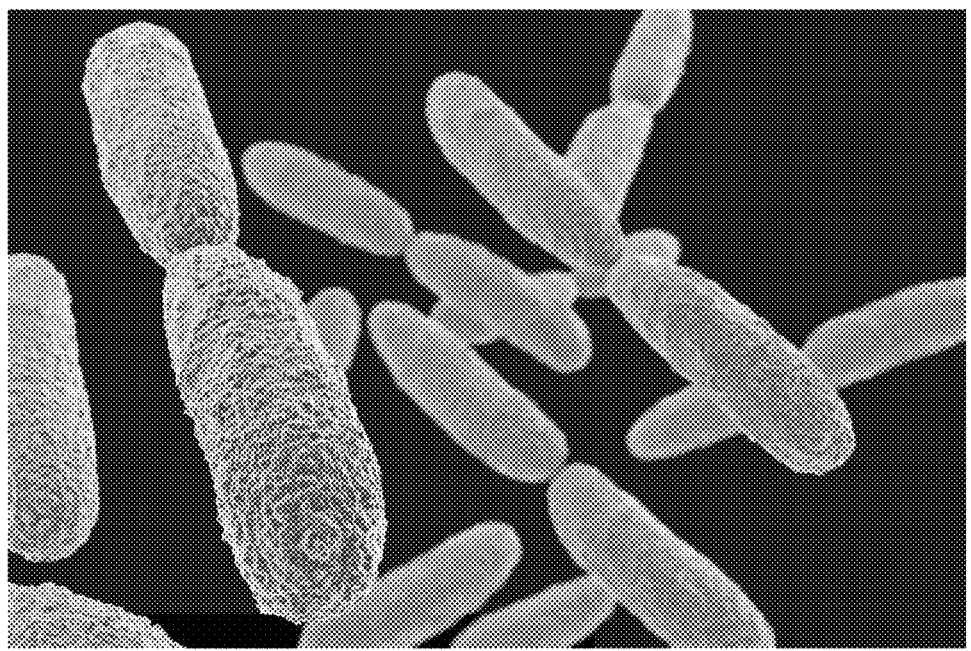
Fig. 9 – *Klebsiella*
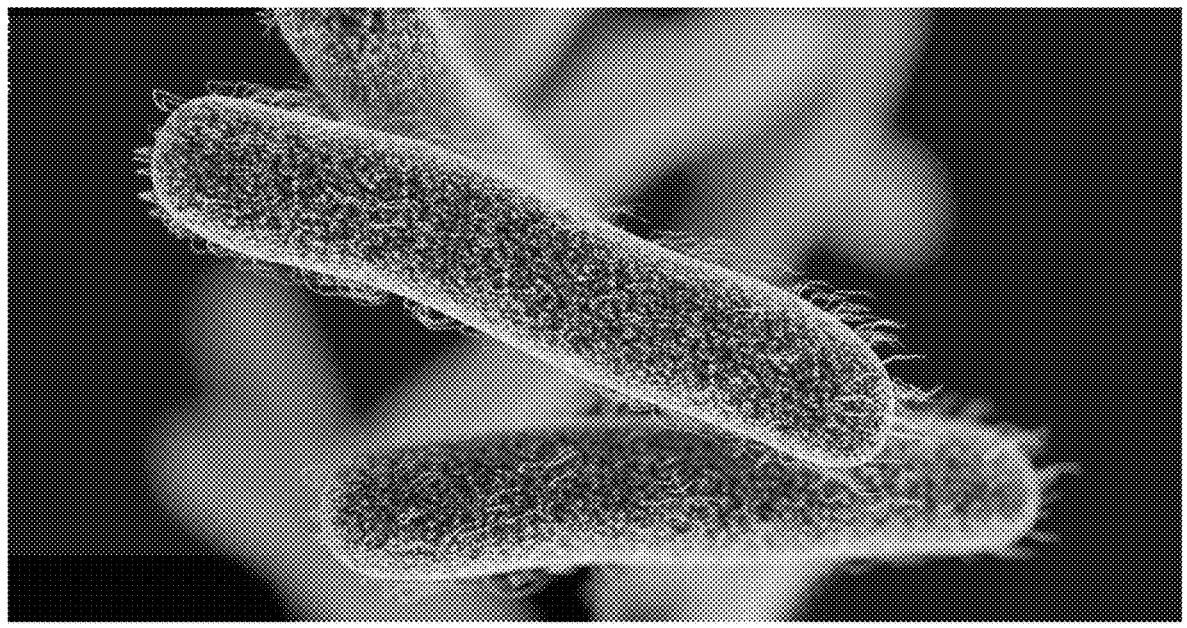
Fig. 10 – Shignella

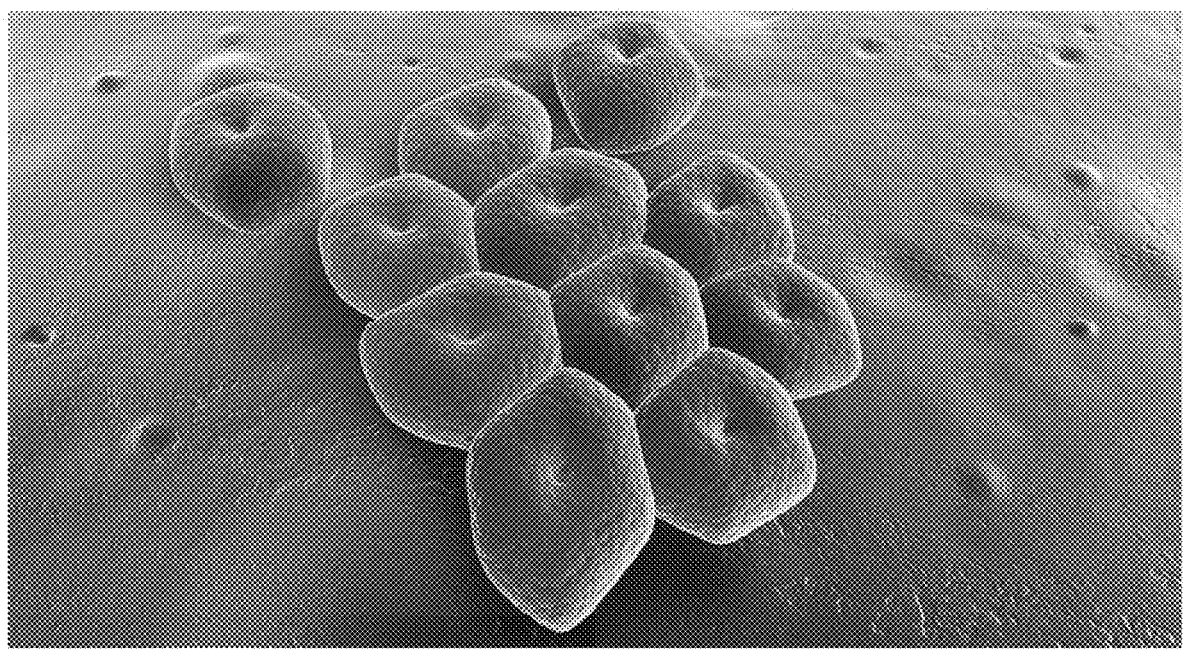
Fig. 11 - *Acinetobacter baumannii*

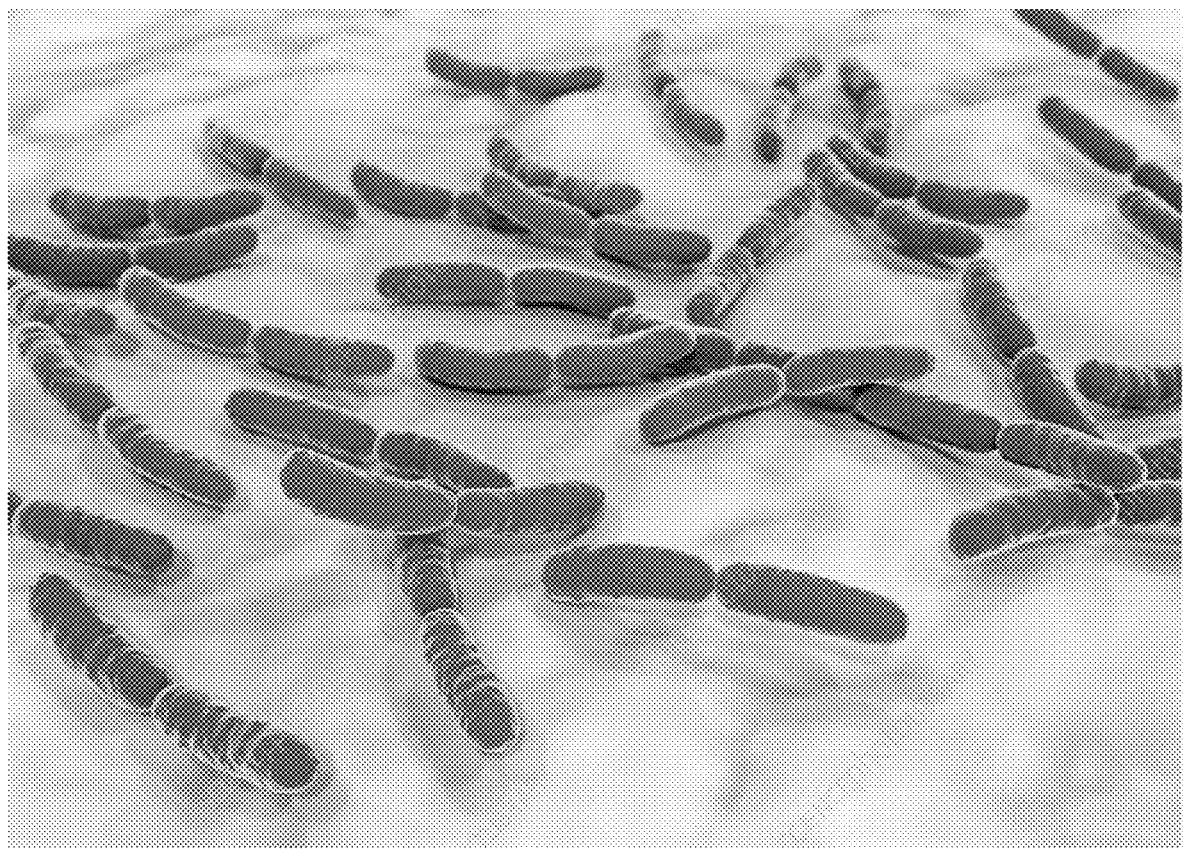
Fig. 13 – L. crispatus

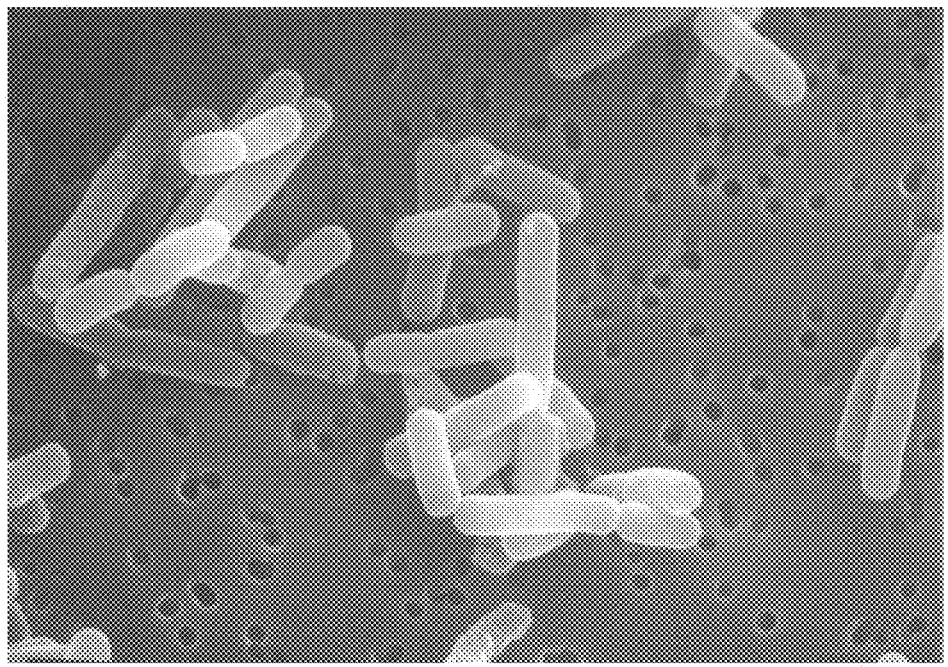
Fig. 14 – *Lactobacillus reteri*
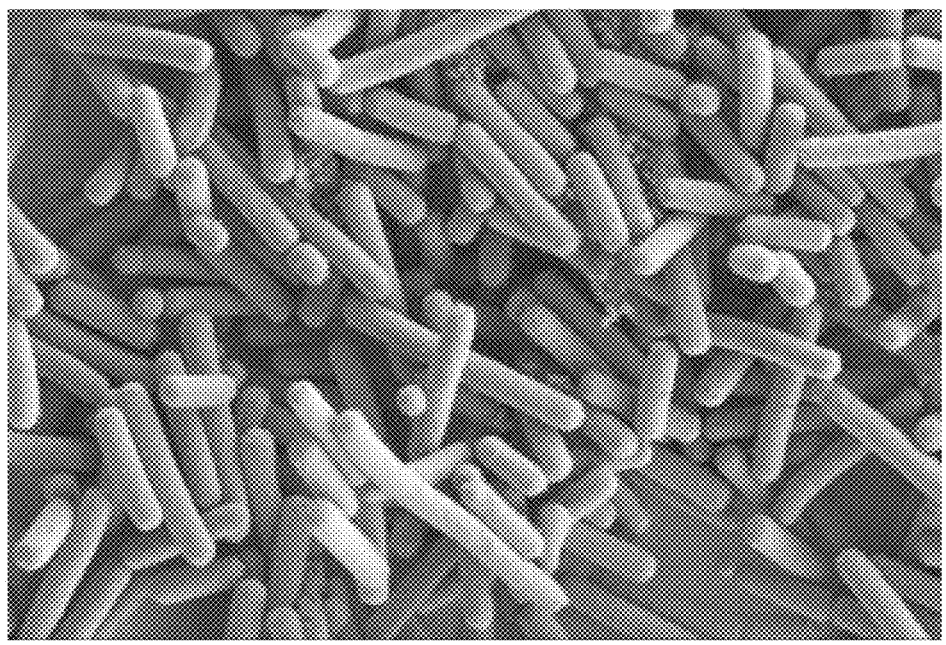
Fig. 15 - *Lactobacillus johnsonii*

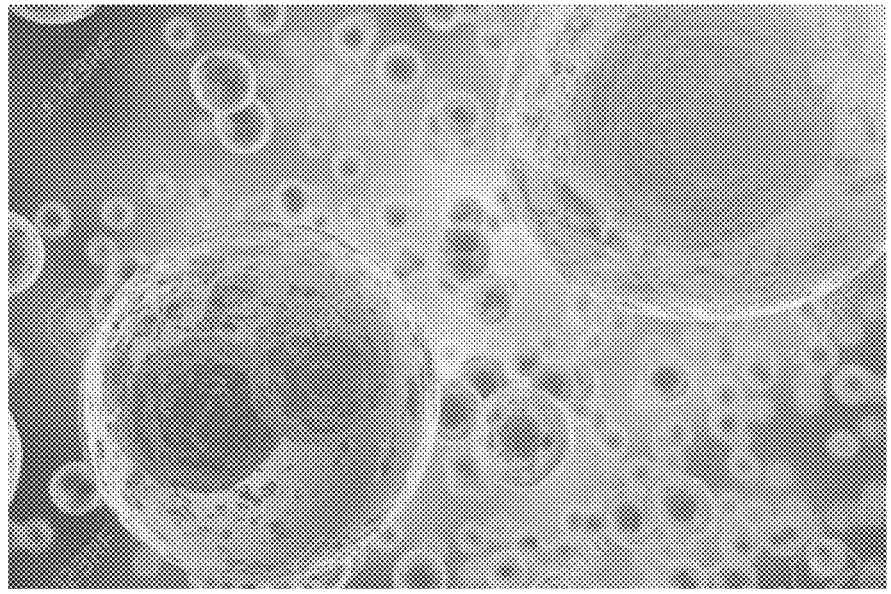
Fig. 16 - *Nitrosomonas eutropha*
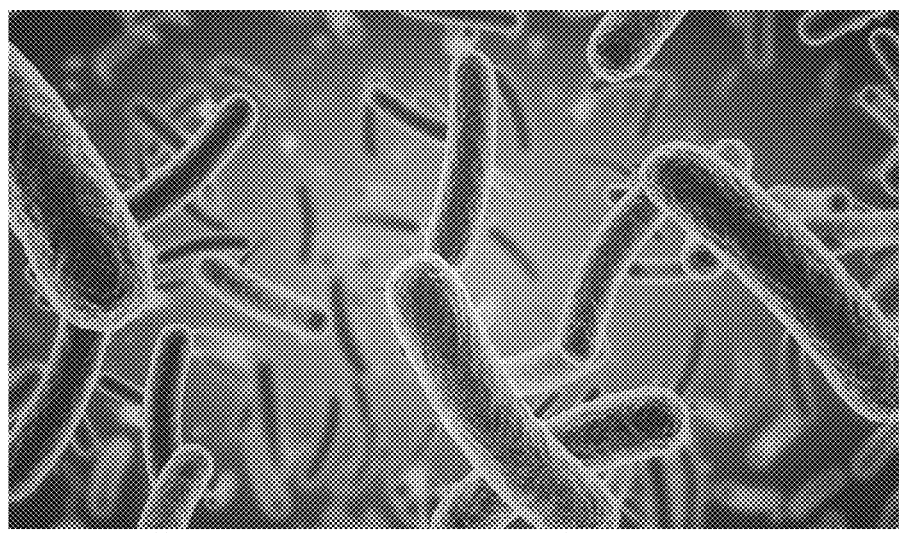
Fig. 17 - *Cutibacterium acnes*

METHOD AND SYSTEM FOR MODULATING AN INDIVIDUAL'S SKIN MICROBIOME

RELATED APPLICATIONS

This application is a continuation-in-part of U.S. patent application Ser. No. 18/130,946, filed Apr. 5, 2023, which is continuation-in-part of U.S. patent application Ser. No. 18/178,847, filed Mar. 28, 2023, which is a continuation-in-part of U.S. patent application Ser. No. 18/087,545, filed Dec. 22, 2022, which is a continuation-in-part of U.S. patent application Ser. No. 17/854,422, filed Jun. 30, 2022 (now U.S. Pat. No. 11,672,835, issued Jun. 13, 2023), which is a continuation-in-part of U.S. patent application Ser. No. 17/848,759, filed Jun. 24, 2022 (now U.S. Pat. No. 11,642,382, issued May 9, 2023), which is a continuation-in-part of U.S. patent application Ser. No. 17/835,204 filed Jun. 8, 2022 (now U.S. Pat. No. 11,529,379, issued Dec. 20, 2022), which is a continuation-in-part of U.S. patent application Ser. No. 17/567,295 filed Jan. 3, 2022, which is a continuation-in-part of U.S. patent application Ser. No. 17/337,600, filed Jun. 3, 2021 (now U.S. Pat. No. 11,213,552, issued Jan. 4, 2022), which is a continuation-in-part of Ser. No. 17/027,953, filed on Sep. 22, 2020 (now U.S. Pat. No. 11,026,982, issued Jun. 8, 2021), which is a continuation-in-part of U.S. patent application Ser. No. 16/917,096, filed Jun. 30, 2020 (now U.S. Pat. No. 10,940,169, issued Mar. 9, 2021), which is a continuation-in-part of U.S. patent application Ser. No. 16/782,364, filed Feb. 5, 2020 (now U.S. Pat. No. 10,835,560, issued Nov. 17, 2020), which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application is a continuation-in-part of U.S. patent application Ser. No. 18/234,132, filed Aug. 15, 2023, which is a continuation-in-part of U.S. patent application Ser. No. 18/232,980 filed Aug. 11, 2023, which is a continuation-in-part of U.S. patent Application Ser. No. 18/232,433 filed Aug. 10, 2023, which is a continuation-in-part of, U.S. patent application Ser. No. 18/143,399, filed May 4, 2023, which is a continuation-in-part application of U.S. patent application Ser. No. 17/893,384, filed Aug. 23, 2022, which is a continuation-in-part application of U.S. patent application Ser. No. 17/694,775, filed Mar. 15, 2022, which is a continuation-in-part of U.S. patent application Ser. No. 17/023,736, filed Sep. 17, 2020 (now U.S. Pat. No. 11,419,903, issued Aug. 23, 2022, which is a continuation-in-part of U.S. patent application Ser. No. 17/011,175, filed Sep. 3, 2020 (now U.S. Pat. No. 11,273,187, issued Mar. 15, 2022), which is a continuation-in-part of U.S. patent application Ser. No. 16/722,117, filed Dec. 20, 2019 (now U.S. Pat. No. 10,842,834, issued Nov. 24, 2020), which is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

This application is a continuation-in-part of U.S. patent application Ser. No. 18/234,544, filed Aug. 16, 2023, which is a continuation-in-part of U.S. patent application Ser. No. 18/103,768, filed Jan. 31, 2023, which is a continuation-in-part of U.S. patent application Ser. No. 17/738,771, filed May 6, 2022, which is a continuation-in-part of U.S. patent application Ser. No. 16/904,056, filed Jun. 17, 2020 (now U.S. Pat. No. 11,523,934, issued Dec. 13, 2022), which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is also a continuation-in-part of U.S. patent application Ser. No. 17/836,079, filed Jun. 9, 2022, which is a continuation-in-part of U.S. patent application Ser. No. 16/884,772 filed on May 27, 2020 (now U.S. Pat. No. 11,357,722, issued Jun. 14, 2022, which is a continuation-in-part of U.S. patent application Ser. No. 16/136,950, filed Sep. 20, 2018 (now U.S. Pat. No. 10,668,014, issued Jun. 2, 2020), which is a continuation of U.S. patent application Ser. No. 15/385,278, filed Dec. 20, 2016 (now U.S. Pat. No. 10,085,938, issued Dec. 2, 2018), which claims the benefit of U.S. Provisional Application Ser. No. 62/387,404, filed Dec. 24, 2015.

The present application is a continuation-in-part of U.S. patent application Ser. No. 17/543,992, filed Dec. 7, 2021, which is a continuation-in-part of U.S. patent application Ser. No. 16/804,361, filed Feb. 28, 2020 (now U.S. Pat. No. 11,191,665, issued Dec. 7, 2021), which is a continuation-in-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat. No. 10,010,568, issued Jul. 3, 2018), which seeks priority from U.S. Provisional Patent Application Ser. No. 62/260,906, filed Nov. 30, 2015.

This application is a continuation-in-part application of U.S. patent application Ser. No. 16/776,861, filed Jan. 30, 2020 (now U.S. Pat. No. 10,864,109, issued Dec. 15, 2020), which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 30, 2016 (now U.S. Pat. No. 10,086,018, issued Oct. 2, 2018), which is a non-provisional of U.S. Provisional Patent Application Ser. No. 62/274,550, filed on Jan. 4, 2016.

This application is a continuation-in-part of U.S. patent application Ser. No. 16/426,346, filed May 30, 2019 (now U.S. Pat. No. 10,716,815, issued Jul. 21, 2020), which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016).

The present application is a continuation-in-part of U.S. patent application Ser. No. 17/543,992, filed Dec. 7, 2021, which is a continuation-in-part of U.S. patent application Ser. No. 16/804,361, filed Feb. 28, 2020 (now U.S. Pat. No. 11,191,665, issued Dec. 7, 2021), which is a continuationin-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat. No. 10,010,568, issued Jul. 3, 2018), which seeks priority from U.S. Provisional Patent Application Ser. No. 62/260,906, filed Nov. 30, 2015.

This application is a continuation-in-part application of U.S. patent application Ser. No. 16/037,053, filed Jul. 17, 2018 (abandoned).

This application is also a continuation-in-part of U.S. patent application Ser. No. 14/752,192 filed on Jun. 26, 2015 (now U.S. Pat. No. 9,549,842, issued Jan. 24, 2017).

The entire disclosure of the prior applications are considered to be part of the disclosure of the accompanying application and are hereby incorporated by reference.

FIELD OF THE INVENTION

Compositions, systems and methods of improving the health of the microbiome of an individual's skin relate to the provision of skin contacting formulations containing beneficial bacteria and other microbe components to foster the growth and maintenance of a healthy skin microbiome.

BACKGROUND OF THE INVENTION

The skin is the human body's largest organ, colonized by a diverse milieu of microorganisms. Colonization is driven by the ecology of the skin surface, which is highly variable depending on topographical location, endogenous host factors and exogenous environmental factors. Microorganisms including bacteria, fungi, and viruses are known to colonize the skin. Human skin continuously undergoes self-renewal, so resident microbial cells are shed in the process. Most of the microbes found on the skin are harmless to healthy individuals. Some are considered to be mutualistic organisms and confer health benefits to the skin by secreting, for example, antibacterial substances, preventing pathogen colonization, and influencing host immune responses. Changes in skin ecology or microecology with an excessive proliferation of pathobionts results in a spectrum of skin diseases from mild acne, to dermatitis and psoriasis. Further, skin pathobionts may accelerate the progression of skin diseases when the skin barrier is breached. On the other hand, commensal microorganisms can cause diseases and infections if the physical barrier of the skin has been compromised due to trauma or injuries. Changes in skin ecology or microecology with an excessive proliferation of pathobionts results in a spectrum of skin diseases from mild acne, to dermatitis and psoriasis. Skin pathobionts may accelerate the progression of skin diseases when the skin barrier is breached.

The skin and gastrointestinal ("GI") tracts of humans are colonized by a diverse array of microorganisms beginning at the time of birth when an infant is exposed to the maternal microflora and other environmental microbes. From the time of initial colonization, the human microbiome remains in a state of flux where the composition of the resident microflora changes over time in response to factors intrinsic and extrinsic to the host.

Probiotics are so-called "good" microorganisms (typically bacteria) that are ingested (or contacted with a person) alive by an individual so that the introduced microorganisms can colonize the GI tract of the person. Conventional prebiotics are ingestible ingredients that selectively support the growth or survival of the "good" microorganisms which are desirably present in the GI tract. Conventional prebiotics are typically a nutrient source (e.g., fructooligosaccharide or galactooligosaccharide) that can be assimilated by one or more members of the GI microbiome, but which are not digestible by the human host.

Human skin is colonized by a diverse array of microorganisms, with such colonization beginning shortly after birth when an infant is exposed to the maternal microflora. From the time of initial colonization, the human microbiome changes over time in response to factors intrinsic and extrinsic to the host. The makeup of the human skin microbiome differs significantly from the makeup of the GI microbiome in terms of both the type and variety of microorganisms present.

Members of the GI and skin microbiomes utilize different nutrient sources due to, at least in part, the starkly contrasting environments in which the two microbiomes are found and the substrates available for use as food. Dietary requirements of microorganisms can vary significantly from one species to the next, and it is not uncommon for an agent that exhibits prebiotic activity on a particular microorganism to exhibit no prebiotic activity on a different microorganism. For example, prebiotics designed for the GI microbiota have historically been carbohydrate-based materials that serve as food for resident glycolytic driven microorganisms. The microflora present on the skin of a person, however, can include lipophilic organisms, which would not necessarily be expected to assimilate carbohydrates. Even the glycolytic microorganisms present on the skin may not utilize the same kinds of carbohydrates as GI microbes. The make-up of the GI and skin microbiomes of a human may vary significantly and there can also be significant variability in the make-up of the same microbiome between individuals. The surface of mammalian skin typically includes a wide variety of microorganisms, which may vary from species to species, individual to individual, and from location to location on an individual. Certain undesirable microorganisms, such as pathogenic bacteria, yeasts and molds, may attempt to colonize the skin and upset the balance of a healthy microbiome.

The development of molecular techniques to identify and quantify microbial organisms has revolutionized the microbial world. Genomic characterization of bacterial diversity relies on sequence analysis of the 16S ribosomal RNA gene, which is present in all bacteria and archaea. The 16S rRNA gene contains species-specific hypervariable regions, which allow taxonomic classification, and highly conserved regions, which act as a molecular clock and a binding site for PCR primers. Using current technologies, an organism does not need to be cultured to determine its type by 16S rRNA sequencing.

The global population is rapidly aging. Currently, 566 million people are .gtoreq.65 years old worldwide, with estimates of nearly 1.5 billion by 2050, particularly in developing countries. Infections constitute a third of mortality in people .gtoreq.65 years old. Moreover, lengthening life spans correlate with increased time in hospitals or long-term care facilities and exposure to drug-resistant pathogens. The risk of nosocomial infections increases with age, independent of duration spent in healthcare facilities. One theory is that as a person ages, their immune system changes and is less robust in addressing bacterial infections. By enhancing the microbiome of a person's skin as they age, it is believed that infections that would otherwise be encountered will be avoided, or at least the frequency and severity of the same will be decreased.

Acne affects hundreds of millions of people worldwide, believed to involve the bacterial colonization of affected skin and consequent inflammation. Acne leads to emotional distress and even depression. Sebum is produced by the skin's sebaceous glands, providing nutrients for a number of bacteria, including the anaerobic gram-positive bacterium *Cutibacterium acnes*, which decomposes the sebum fats to glycerine and fatty acids. This often results in an inflammation of the skin and the formation of pimples and pustules. As used herein, the terms *Propionibacterium acnes* and *Cutibacterium acnes* should be understood to refer to the same bacteria and can be used interchangeably. Topical applications of antibiotics, including erythromycin, clindamycin, metronidazole, sulfacetamide, doxycycline or minocycline, or systemic applications of antibiotics, can be used to reduce the number of *C. acnes*, but there are high relapse rates and issues due to development of antibiotic-resistant bacteria.

*C. acnes* is considered an aerotolerant anaerobe because it possesses enzymatic systems able to detoxify oxygen, allowing it to be sustained on the surface of the skin.

The genus *C. acnes* has been further subdivided into subspecies, such as *C. acnes* subsp. *defendens* and *C. acnes* subsp. *elongatum*. Unlike other Gram-positive bacteria, *C. acnes* has a unique cell wall and envelope, containing phosphatidylinositol, triacylglycerol, and many other common lipids. The cell wall of *C. acnes* consists of peptidoglycan (PNG), but of a type different from that of other Gram-positive bacteria, in that the peptide chain contains the L-acid L-diaminopelic acid and D-alanine. *C. acnes* has a strong impact of the skin's immune system.

The disease pathogenesis of atopic dermatitis is believed to be due to a combination of environmental and genetic factors resulting in compromised skin barrier function, inflammation and the appearance of erythema and papules. Up to 80-100% of patients suffering from atopic dermatitis are colonized with *S. aureus* compared to only about 5-30% of control patients. During atopic dermatitis flare-ups, the loss of microbiome diversity towards an overgrowth of *S. aureus* correlates with disease severity. *S. aureus* strains isolated from atopic dermatitis lesions have been shown to produce a variety of toxins and enzymes with aggressive cell-damaging and inflammation-inducing properties. *S. aureus* directly damages keratinocytes by adhering to cells and forming transmembrane pores through the secretion of staphylococcal toxin ultimately leading to the breakdown of cellular ATP metabolism. *S. aureus* superantigens elicit the production of IgE antibodies, which levels correlate with disease severity.

Personal care products represent a considerable proportion of the global economy, with a total estimated market valuation of over USD 500 billion in 2022 and a predicted annual growth rate of over 6%. The skin microbiome has many demonstrable applications for personal care product development as the composition and stability of an individual's skin microbiota is critically important in the maintenance of cutaneous homeostasis through pathogenic colonization resistance.

There is a need for new treatments for atopic dermatitis that can decrease the toxic and inflammatory effects induced by *S. aureus* colonization with minimal side effects. There is also a long-felt need for effective treatments to enhance the health of an individual's skin. The present invention provides a method and system for satisfying such needs.

SUMMARY OF THE INVENTION

Certain embodiments of the present invention are directed to a method and system for modulating an individual's skin microbiome. Particular aspects of the present invention are directed to methods that employ topical probiotics produced with the aim of establishing stable communities of beneficial microorganisms. The human skin is an ecological niche which harbors a rich and compositional diversity microbiome. Certain embodiments of the present invention are directed to a variety of skin-microbiome-derived compounds for therapeutic applications, ranging from antioncogenic agents relevant in skin cancer therapy to treatment strategies for antimicrobial-resistant bacterial and fungal infections as well as cosmetic formulations to enhance the appearance and health of an individual's skin and to mitigate various skin conditions such as acne and eczema and reducing skin aging.

Commensals such as *Staphylococcus epidermidis* and *Cutibacterium acnes* provide host benefit through nutritional competition with pathogens, stimulating host antimicrobial peptide secretion. Certain aspects of the present invention are directed to manipulating the mechanisms by which microorganisms interact to form a microbiota community structure using therapeutically relevant formulations. Such formulations include one or more bacterial-derived peptides and proteins capable of exerting bacteriostatic and bactericidal activity to inhibit the growth of undesired pathogenic bacteria. Preferably, in contrast to broad-spectrum antibiotics, formulations of the present invention are tailored to the clearance of specific pathogenic organisms with minimal disruption to natural flora.

For example, in certain formulations the commensal *S. lugdunensis* is employed such that the generation of lugdunin is facilitated to disrupt the transmembrane pH gradients and thus inhibit respiration. Similarly, in certain embodiments, the commensal *Staphylococcus simulans* is employed to generate lysostaphin to effect an anti-*S. aureus* bactericidal activity.

Still other embodiments include the use of the pathogen *Enterococcus faecium* to generate the bacteriocin CRL35 and/or *Bacillus subtilis* to generate subtilosin, especially in combination with other features as described herein. Several embodiments are directed to the use of phages associated with the predominant skin bacterial genera *Staphylococcus*, *Cutibacterium* and *Streptococcus* as therapeutic bacteriophages.

Thus, in certain embodiments, direct modulation of an individual's skin microbiome via phage therapy is employed to treat eczema. To circumvent inherent phage limitations, various embodiments of the present invention are directed to the modification of phage DNA to encode CRISPR-Cas9 systems to accomplish the resensitization of resistant bacteria to antibiotic treatments and/or bactericidal toxins, while also preferably removing the replicative cycle of phages. Many embodiments are directed to the inhibition of undesired microbial growth through a combination of various mechanisms, including a reduction in skin pH, generation of direct antimicrobial activities by bacterial formulations, and the promotion of commensal adherence, such as via the secretion of lipases by the skin commensals *Cutibacterium* spp. and *Staphylococcus* spp., to diminish proinflammatory cytokine induction and the beneficial degradation of triglyceride to liberate glycerol, thereby stimulating the recovery of irritated skin. Microbial fermentation of glycerol and the production of lactic acid to promote an acidic pH of an individual's skin is believed to upregulate the gene expression of essential skin barrier proteins. In certain embodiments, Sphingosine and sapienic acid are preferably included in certain formulations to provide a stable antimicrobial factor for use in cosmetic products.

Certain aspects of the present invention are directed to the disruption of biofilms on an individual's skin. Various formulations of the present invention may include, for example, *S. epidermidis* to generate the secretion of the serine protease, and Esp, to disrupt biofilm formation. Other biofilm inhibitors, such as those that inhibit the polysaccharide adhesion operon, may be employed in various formulations.

Several embodiments of the present invention employ a CRISPR system to disrupt biofilm formation by inhibiting or reducing certain virulence factors that facilitate processes such as biofilm formation. For example, in certain embodiments, *S. epidermidis*, *S. hominis* and *S. simulans*, are included in formulations to secrete inhibitors of the *S. aureus* accessory gene regulator (agr) that interferes with colonization.

Many embodiments of the present invention are directed to the reshaping of the skin microbiota community structure by employing one or more of the formulations as described herein to provide commercial skin products. For example, certain methods and formulations are directed to addressing sebum accumulation that results in *C. acnes* extracellular lipases creating proinflammatory small chain fatty acids (SCFAs). Several embodiments of the present invention are directed to the use of probiotics to accomplish *C. acnes* inhibition leading to a reduction of the severity of acne. Certain formulations that include one or more of *E. faecalis*, *Lactobacillus* sp., and *Lactobacillus plantarum* are topically applied to an individual's skin to reduce acne lesions, thereby inhibiting *C. acnes*.

Atopic dermatitis (AD) is the most common inflammatory skin disorder globally, characterized by an increased abundance of *S. aureus* and *Malassezia* spp. which secrete virulence factors (e.g., toxins). Invasive *Staphylococcus aureus* infections are common, causing high mortality, compounded by the propensity of the bacterium to develop drug resistance. *S. aureus* is a bacterium that may be commensal, colonizing, latent or disease-causing, with such states defined by the interplay between *S. aureus*, its host and other bacteria in its environment. The genomic plasticity of *S. aureus* reveals its dualism as both a commensal and an opportunistic pathogen. *Staphylococcus aureus* is one of the foremost opportunistic bacterial pathogens of humans. *S. aureus* colonizes approximately 20-30% of humans persistently on the skin, with the pathogenic nature of such bacterium shaped by other commensals. *S. aureus* infections can be acute, chronic and persistent. *S. aureus* produces a large array of virulence and immune evasion factors that hinder the human immune response. Typically, *S. aureus* does not elicit a protective immune response, meaning that recurrent infections are common throughout life. Certain embodiments of the present invention employ CRISPR systems to reduce or eliminate virulence factors of *S. aureus* to render it less pathogenic.

Certain aspects of the present invention are directed to reducing the likelihood of atopic dermatitis (AD) via the use of CRISPR systems to reduce or interfere with the virulence factors of *S. aureus* and *Malassezia* spp. In certain embodiments, formulations containing two or more of *S. epidermidis, S. hominis, Vitreoscilla filiformis, Streptococcus thermophilus* and *Lactobacillus johnsonii* are employed to reduce the populations of *S. aureus* and *Malassezia* abundance in AD patients.

Skin aging corresponds with physiological changes altering elasticity, thickness and moisture. Elderly skin microbiomes are associated with consistently reduced *Cutibacterium* spp. and *Lactobacillus* spp. across multiple bodily sites. Reduced *C. acnes* abundance leads to reduced glycerol, fatty acids and antioxidant production, thus perpetuating physiological changes associated with cutaneous aging.

Certain embodiments include the use in skin formulations of one of *Cutibacterium* spp. and *Lactobacillus* spp and *Streptococcus* spp. to achieve higher elasticity of an individual's skin, with such formulations responsible for an increased gene expression of collagen, filaggrin and lipid synthesis proteins, believed to be due mainly to the generation of spermidine levels by such bacteria. Certain embodiments of the present invention are directed to methods that involve the provision of spermidine-producing streptococci to older humans to enhance the youthful aspects of their skin.

Certain other embodiments are directed to applying *Lactobacillus* spp. to reduce photoaging through an ultraviolet protective effect to reduce collagen degradation. Certain embodiments involve the use of *S. epidermidis* to increase murine ceramide content on skin. Ceramides provide a diverse and vital range of functions through forming a major component of the lipid barrier to the regulation of keratinocyte proliferation. Certain embodiments involve the use of streptococci to produce hyaluronic acid and streptococcal lysates to increase skin ceramide production.

One focus of the present invention is to employ a method of modulating an individual's skin microbiome by administering to a region of the individual's skin a therapeutically effective amount of a bacterial formulation comprising at least one bacteria selected from the group consisting of *Lactobacillus reuteri, Lactobacillus johnsonii, Janthinobacterium, Lactobacillus crispatus, Cutibacterium acnes,* and *Nitrosomonas eutropha*. Such bacterial formulation may be in the form of a lotion, ointment or gel that is adapted to be rubbed onto a region of the individual's skin, and may include abiotic augmentations that include fatty acids. Preferably at least one bacteria comprises a heat-killed bacteria and the bacterial formulation is provided in an amount effective to treat, inhibit or reduce a skin condition selected from the group consisting of eczema, atopic dermatitis, acne, allergic inflammation, ultra-violet-induced skin damage, and skin hypersensitivity. Other embodiments include a bacterial formulation that further comprises one or more of *Staphylococcus, Bifidobacterium,* and *Streptococcus*, with still others involving administering to the individual one of a prebiotic, a metabolite, and a postbiotic.

Preferably, a cleanser composition accompanies the use of the bacterial formulation, with such cleanser including one of sodium methyl cocoyl taurate, sodium cocoyl glutamate, coco glucoside, caprylyl/capryl glucoside, sodium cocoyl Isethionate, and cetearyl alcohol; a serum composition comprising at least two of the following: indole-3-carbinol, resveratrol, niacinamide, nicotinic acid, nicotinamide mononucleotide, nicotinamide riboside, quercetin, tryptophan, diiodomethane, *Boswellia serrata*, and indirubin; and at least one barrier-restoring oil comprising at least one of sunflower oil, coconut oil, murumuru oil, sea buckthorn oil, sachi inchi oil, and babbasu oil. Certain embodiments use bacteria in the bacterial formulation that have been modified by using a clustered regularly interspaced short palindromic repeats (CRISPR) CRISPR associated protein (Cas) system or a CRISPR from *Prevotella* and *Francisella* 1 (Cpf1) system to reduce the production of a virulence factor. Yet other embodiments include at least one bacteria of *Cutibacterium acnes* or *Janthinobacterium*, and preferably at least one bacteria in the bacterial formulation produces short-chain fatty acids, such as propionate, acetate, butyrate and valerate. More preferably, at least one bacteria in the bacterial formulation does at least one of: suppress the growth of *S. aureus*; reduce the colonization of *S. aureus* on the individual's skin; and inhibit biofilm formation by *S. epidermidis*. Still other embodiments kill or retard the growth of a pathogenic bacteria within the individual, such pathogenic bacteria selected from the group consisting of *Staphylococcus aureus; Pseudomonas aeruginosa; Klebsiella; Streptococcus; Salmonella; Shigella; Mycobacterium tuberculosis; Enterococcus; E coli; Clostridium; Neisseria gonorrhoeae; Acinetobacter baumannii*; and *Campylobacter*. Other embodiments enhance the growth of a beneficial bacteria such as *C. acnes, Akkermansia, Bacteroides, Bifidobacterium, Fusobacterium, Coprococcus, Lactobacillus, Propionibacterium, Nitrosomonas eutropha, Ruminococcus, Veillonella, Prevotella*, and *Streptococcus* bacteria.

Other embodiments employ the use of at least two probiotic strains on an individual's skin in a concentration of at least 1×108 via AFU, with the two probiotic strains being either live or heat-killed and selected from the group consisting of *Cutibacterium, Staphylococcus, Corynebacterium, Micrococcus* spp., Actinobacteria, Proteobacteria, and Firmicutes. Other embodiments include administering to an individual's skin at least one probiotic strain that does not upregulate innate immune response genes selected from the group consisting of CXCL1, CXCL3, CXCL8, CXCL10. Yet others involve administering to an individual's skin at least one probiotic strain that does not upregulate innate immune response genes selected from the group consisting of IL10RA, PTGS2, F2RL1, TRIM29, TRAF4, LGALS3, CD55, TRIM8, CASP4, IFNGR1, ADA, NOD1, NOS2, and APP.

Certain methods of modulating an individual's skin microbiome are performed to address a skin condition, such as eczema, atopic dermatitis, acne, allergic inflammation, ultra-violet-induced skin damage, and skin hypersensitivity. The bacterial formulation may further include bacteria such as *Faecalibacterium prausnitzii, Bifidobacterium, Lachnospira, Veillonella, Coprococcus, Akkermansia muciniphila* and *Rothia*, as well as arabinogalactan and a UV protectant chemical. A preferred embodiment involves the use of a bacterial formulation that is administered to an individual's skin in an amount sufficient for the bacterial formulation to generate an amount of tryptophan metabolites sufficient to act as aryl hydrocarbon receptor (AHR) agonists to thereby reduce inflammation on an individual's skin.

One aspect of the present invention is directed to the use of human specific species of bacteria that are then modified to enhance one or more characteristics deemed beneficial to the skin microbiome and health of an individual, including bacteria that have been modified via a CRISPR-Cas9 and/or Cpf1 system to either repress the expression of a particular protein or lipid, or to increase the production of beneficial microbial secretions. Clustered Regularly Interspaced Short Palindromic Repeats from *Prevotella* and *Francisella* 1 or CRISPR/Cpf1 is a DNA-editing technology analogous to the CRISPR/Cas9 system. One objective is to avoid modifying an individual's human genome, but instead, to significantly affect the health of humans by employing modifications to the skin microbiome. Use of human specific strains of bacteria, whether they are commensal or pathogenic, including bacteria that are modified to alter their native pathogenicity, is one preferred aspect of many embodiments of the present invention.

Certain aspects of the present invention are directed to a method for altering the microbiome of an individual's skin by administering to a region of the skin of an individual an effective amount of a bacterial formulation. In one preferred embodiment, the individual is a newborn and the step of administering is performed within the first 6 hours of the newborn's birth. Such a bacterial formulation may be a lotion, ointment or gel adapted to be rubbed onto the newborn's skin. The bacteria included in the bacterial formulation may vary to address particular concerns or diseases. For example, the bacterial formulation may include bacteria selected from the group consisting of *Nitrosomonas eutropha* and *Propionibacterium* species. More particularly, the equilibrium of a bacterial population of the region of the skin of the individual is modified to increase the number of *Propionibacterium* bacteria and to decrease the number of *Staphylococcus* bacteria on the individual's skin in such region. In other embodiments, the bacterial formulation includes the bacteria *Staphylococcus aureus* that has been modified by employing a CRISPR-Cas or Cpf1 system to interfere with *S. aureus* virulence regulation involving the Agr quorum-sensing signaling molecule. In several embodiments, the bacterial formulation comprises a bacteria that has a tropism specific for the human species. In others, the bacterial formulation comprises at least two of the bacteria selected from the group consisting of: *Prevotella, Lactobacillus johnsonii, Bacteroides fragilis, Lactobacillus ruminis* and *L. infantis*. In certain embodiments the bacteria is an ammonia oxidizing bacteria. In other embodiments, the region of the skin to which the bacterial formulation is applied is the scalp. In various embodiments, rather than using a wild-type bacteria, the bacteria employed is one that has been modified by CRISPR-Cas or CRISPR-Cpf1 to delete a functional virulence factor from the bacteria. In particular embodiments, the method includes administering to the skin a bacteria that produces tomatidine. In others, the bacteria produces p53. Thus, in some embodiments, the method involves use of bacteria wherein a CRISPR-Cas or CRISPR-Cpf1 system is employed to insert a gene for the production of tomatidine and/or p53 into at least one of the bacteria in the bacterial formulation. In others, a CRISPR-Cas or CRISPR-Cpf1 system is employed to insert one or more genes into the bacteria comprising the bacterial formulation to facilitate the oxidizing of ammonia by the bacteria. To further enhance the ability of desired bacteria to be maintained on the skin of an individual, certain methods further comprise administering to the individual's skin a prebiotic that comprises a nutrient source for the bacteria, and preferably one that is not digestible by the individual. In particular embodiments, the method further includes administering to the skin an extract derived from a helminth selected from the group consisting of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus*, and *Trichinella spiralis*. In still others, the bacterial formulation includes at least one arabinogalactan. Yet others include at least one of the following: *L. infantis*, and *L. johnsonii*. In a particular embodiment, the bacterial formulation includes at least one bacteria modified via a CRISPR-Cas system to express a gene encoding interferon regulatory factor 4.

In particular embodiments, in view of the tropism demonstrated by *S. pyogenes* for humans, and the recognition that such bacterial species is found in both the oral and skin microbiome of humans, *S. pyogenes* is a preferred bacterial species to employ in various embodiments of the present invention.

In still other embodiments, the focus is on interspecies interactions within mixed microbial communities, with the objective being to modify competitive relationships involving nonbiocidal biosurfactants, enzymes, and metabolites produced by bacteria and other microorganisms in a manner such that selection of particular bacterial species can be employed to inhibit initial adhesion, trigger matrix degradation, encourage jamming of cell-cell communications, and induce biofilm dispersion. Nonbiocidal molecules are thus employed to modify competitive interactions within biofilms in a manner that promotes the overall health of an individual's microbiome, especially on the skin.

In certain embodiments, a bacterial formulation is applied to newborns within a critical window of time after birth, preferably within the first 24 hours of the newborn's birth, more preferably within 6 hours of their birth, even more preferably within 3 hours of birth, and most preferably within an hour after their birth. The administration can be by several methods, but preferably is a lotion, ointment or gel that is rubbed onto the newborn's skin, preferably all over his/her entire body. A spray or mist can also be applied that contains the bacterial and microbe formulations as set forth herein. While not bound by theory, the critical window to apply to the newborn's skin the referenced formulations, e.g., microbial mixtures of bacteria beneficial in triggering immune system development, is within a relatively short time period and is necessary to establish immune tolerance to a variety of commensal microbes. The way and content of microbes presented at a time in which a newborn has his/her skin colonized establishes immune tolerance to particular commensal microbes. The influx of highly activated T cells into neonatal skin is believed to occur in such critical window. So a mother of a newborn has a choice: to simply rely upon chance as to what particular microbes might be present during this critical window of the newborn's establishing immune tolerance to particular bacteria and other microbes; or to provide the newborn with a selected formulation containing predetermined microbes such that the newborn's developing immune system can properly react to the microbes in the predetermined formulation, and thus provide the newborn with the opportunity to develop a more expansive immune tolerance profile. It is believed that the mechanism that promotes tolerance is tissue specific, and thus, the skin and the gut may have different ways by which they mediate tolerance to commensal microbes. To establish a healthy status of a newborn's skin as it relates to commensal microbes on its skin, the particular type of microbes, including bacteria, brought into contact with his/her skin is achieved in a certain time period after birth (e.g. within 1 to 24 hours after birth) so that the developing immune system of the infant establishes tolerance to such microbes, thus avoiding allergies, autoimmune diseases and other related diseases, as well as chronic inflammation of the skin.

In certain embodiments of the present invention, the skin microbiome is enhanced via providing microbes able to metabolize lipids, proteins and carbohydrates, and thus, produce acid that aids in maintaining the so-called "acid mantel" of the skin. In preferred embodiments the bacteria that is modified has a very narrow host tropism, such that the bacteria are specific for the human species and thus, their modification poses little if any risk to other animals or organisms.

Other embodiments are directed to combating infections of a person's skin by the bacteria *Staphylococcus aureus*. *Staphylococcus aureus* is a commensal and pathogen of both humans and cattle. In certain embodiments the accessory gene regulator (Agr) system and the virulence regulation of *S. aureus* pathogenesis is modified to delete or to at least reduce the virulence of the bacteria. In such a way, the present invention provides a way to effectively combat *S. aureus* infections. In various embodiments of the present invention, CRISPR-Cas9 and/or Cpf1 systems are employed to render ineffective virulence factors of such bacteria involved with the establishment and propagation of infection. Several molecules have been found to interfere with *S. aureus* virulence regulation, especially those targeting the Agr quorum-sensing signaling molecule. By modification of this bacterial species using CRISPR-Cas and/or Cpf1 it is possible to achieve broad-spectrum inhibitory effects on most *S. aureus* strains and Agr subtypes.

The tropism of individual bacteria for particular host tissues (e.g., skin vs. respiratory tract vs. gastrointestinal tract) is determined by the array of available adhesion-receptor pairs. In preferred embodiments, bacteria having substantial, if not entire, human host specificity are employed. For example, *Salmonella enterica* serovar *Typhi*, known to be the bacteria responsible for typhoid fever, a life-threatening human disease, demonstrates strict human host specificity. In certain embodiments, the virulence factors of such bacteria are compromised by being modified via the CRISPR-Cas or Cpf1 system to render the modified bacteria as non-pathogenic. Similarly, the bacteria *Neisseria*, the causative agent of gonorrhea, is a disease restricted to humans, and thus similar CRISPR-Cas and/or Cpf1 systems may be employed to reduce if not eliminate the virulence factors of such bacteria. Likewise, *Helicobacter pylori* is known to be an etiologic agent of gastritis and peptic ulcer disease in humans. The iron acquisition system of *H. pylori* by the human lactoferrin receptor system is believed to play a major role in the virulence of *H. pylori* infection. The CRISPR-Cas and/or Cpf1 systems may be employed to reduce if not eliminate the virulence factors of this bacteria. Yet another bacteria demonstrating human tropism is *Haemophilus influenzae*, a Gram negative species that requires heme and has exclusive human host specificity. In certain embodiments, the CRISPR-Cas and/or Cpf1 systems may be employed to reduce if not eliminate the virulence factors of such bacteria. The distinction between throat and skin group A *Streptococcus* has become blurred and to date there have been few advances in treatment of group A *Streptococcus* skin infections. Certain aspects of the present invention include the modification of skin group A *Streptococcus* to reduce the likelihood, if not prevent, related skin diseases, including eczema, atopic dermatitis, acne, allergic inflammation, skin hypersensitivity, UV-induced skin damage, and skin cancer.

One particular aspect of certain embodiments of the present invention relates to the treatment of acne. Acne is the most common skin disease accounting for a quarter of dermatologists' patient volume. Acne is a chronic disease that can significantly impact an individual's quality of life with social, psychological and emotional impairments. Thus, in various embodiments, bacteria are selected that, once applied to an individual's skin, is able to ameliorate acne. Such bacteria include ammonia oxidizing bacteria, preferably provided to a person's skin in combination with a pharmaceutically acceptable excipient. In certain embodiments, bacteria are employed to achieve topical nitric oxide release at or near the surface of the skin and addition of urea or ammonium salts to the skin provides additional substrates that these bacteria utilize to form nitrite. While not intending to be limited thereby, such ammonia oxidizing bacteria may be selected from the group consisting of *Nitrosomonas, Nitrosococcus, Nitrosospira, Nitrosocystis, Nitrosolobus, Nitrosovibrio*, and combinations thereof. In some instances, the ammonia oxidizing bacteria is *Nitrosomonas eutropha* (*N. eutropha*). Such ammonia-oxidizing bacteria are employed to improve skin health and are able to convert ammonia to nitrite, an antimicrobial compound, and nitric oxide. Various aspects of the present invention are directed at restoring and maintaining the delicate balance of the skin microbiome.

The present invention in various embodiments is directed to a variety of consumer products including cosmetic products such as skin care products (bath preparations, skin washing and cleaning products, skin care products, eye cosmetics, lip care products, nail care products, intimate hygiene preparations, foot care), those with special effects (sunscreens, tanning agents, deodorants, anticholinergics, depilatories, shaving, fragrance), those for oral or dental hygiene and those for hair care (shampoos, conditioners, etc.)

One objective of the present invention is to achieve various health and cosmetic benefits by providing a healthy, balanced skin microbiome. Modified bacteria that are beneficial to the skin, especially those modified using CRISPR-Cas systems, are used to enhance the beneficial characteristics of skin microbiomes in a manner that purposefully exposes skin to microbes, rather than the conventional use of anti-bacterial agents to kill bacteria—including beneficial bacteria—on a person's skin. The adherence to the skin of problem flora, such as pathogenic bacteria and yeast, has been associated with numerous ailments, including skin infections, diaper rash, urinary or vaginal infections, and malodors. Use of the present invention addresses such issues in a novel and non-obvious manner.

Other embodiments are directed to prebiotic agents for use on skin. In preferred embodiments, CRISPR-Cas and/or Cpf1 modified bacteria, especially those demonstrating total or substantial tropism for humans, are employed in one or more of the above referenced products, with certain features, namely, virulence factors reduced if not eliminated. In such a manner, there is a competitive inhibition of undesired bacteria with the modified bacteria as set forth herein. In certain embodiments, the cleansing of one's skin to effectively reduce by at least about 50%, more preferably about 30%, and most preferably to reduce by at least about 25%, of native bacteria on an individual's skin portion to be addressed, is performed prior to purposefully contacting the individual's skin with one or more bacteria, and in particular, bacterial species that have been modified via employment of a CRISPR-Cas and/or Cpf1 system to reduce if not effectively compromise the virulence factors of such bacteria, and more preferably a bacteria that has a host specificity exclusive to humans.

In one particular embodiment, bacteria are modified via a CRISPR-Cas system to express a gene identified for grey hair—interferon regulatory factor 4 (IRF4). This gene is involved in regulating production and storage of melanin, the pigment that determines hair, skin and eye color. Hair greying is caused by an absence of melanin in hair. Thus, on various embodiments, bacteria are modified to express IRF4 and topical application of such bacteria to an individual's scalp provides for the prevention of hair turning grey as it otherwise would without such application of such bacteria. In still other embodiments, bacteria are modified to express levels of melanin to maintain hair color when such modified bacteria are contacted with the scalp of an individual.

Certain aspects of the present invention are directed to topically applying live probiotic lactobacilli to beneficially modulate cutaneous microbial interactions and host inflammatory responses in individuals with skin diseases and conditions, including acne symptoms. In other embodiments, postbiotic formulations derived from Lactobacilli-which may include bacterial lysates, supernatants, and/or purified supernatants or metabolites, are applied to an individual's skin.

The skin microbiome also includes various *Lactobacillus* taxa—including those known to be dominant in the human vagina. One aspect of certain embodiments of the present invention is directed to the use of bacteria on an individual's skin that many associate solely with the vaginal microbiome. For example, preferably one of *Lactobacillus crispatus, L. iners, L. gasseri* and *L. jensenii* are employed, most preferably with such bacteria being modified via use of a CRISPR system to reduce or eliminate one or more virulence factors. Other embodiments also include one or more of the following: *L. plantarum/L. pentosus* group and *L. casei/paracasei/rhamnosus* group. Various embodiments of the present invention relate to the use of particular single or combination of strains of *Lactobacillus* in skin probiotics formulations to target skin conditions, such as acne. *Streptococcus salivarius* is another beneficial bacteria that can be employed, alone or in combination with other described bacteria as described herein, as being beneficial against various skin conditions, including acne. Such bacteria can be administered to an individual's skin by way of formulations that may include microcapsules, topical creams, emulsifiers, preservatives, etc. that are selected to be compatible with the bacteria as described, both during storage and use of the formulations. Microcapsules can be used to contain one or more bacterial or probiotic or prebiotic or postbiotic materials such that they can be delivered to a person's skin without mixing or interacting until actually on the skin surface. The rubbing of such formulations on the skin can be employed to break the capsules, releasing the inner core material containing any suspended probiotics.

Early in life, the skin immune system develops abilities to recognize beneficial microorganisms from pathogenic ones so as to avoid constant immune responses and inflammation. Certain aspects of the present invention relate to seeding of desired bacteria on the skin of a newborn to trigger desired immune responses and/or the maturation of an individual's immune system.

Another aspect of the present invention is directed to the ability to edit *Cutibacterium acnes* to remove specific proinflammatory strains and thus prevent or treat acne *vulgaris* or to modulate host immune responses. Thus employing CRISPR systems as described herein, it is possible to selectively kill or reduce the growth of particular bacteria, thus providing for the desired proliferation of other bacteria on the skin surface. The use of CRISPR systems may be directed to enhancing the anti-inflammatory effects of Lactobacilli. In various embodiments of the present invention, CRISPR/Cas9 is used to selectively deplete a given bacterial community of a particular harmful strain or species, or of particular virulence factors possessed by particular strains of bacteria.

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a newborn or other individual.

CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Use of CRISPR-Cas provides a generalized and programmable strategy that can distinguish between closely related microorganisms and allows for fine control over the composition of a microbial population for use in the present invention. Thus, the RNA directed immune systems in bacteria and archaea called CRISPR-Cas systems is employed in various embodiments of the present invention to selectively and quantitatively remove individual bacterial strains based on sequence information. Thus, such genome targeting using CRISPR-Cas systems allows one to specifically remove individual microbial species and strains.

In various embodiments, it is desirable to remove—using CRISPR-Cas systems—particular pathogenic bacteria and/or simply the pathogenic portions of such bacteria—while sparing other desired commensal bacteria.

In various embodiments, one of skill in the art will appreciate that removal of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof. Because CRISPR-Cas acts before transcription occurs, it is able to be employed to target regulatory and other elements on the DNA of microbes that make up the microbiome.

In certain embodiments, *C. acnes* strains are modified in situ especially via the use of CRISPR systems, and/or are provided via in vitro genetically modified *C. acnes*. Various administration methods can be employed, including the use of *Cutibacterium acnes* phagemids and/or bacterial cells comprising these phagemids. Skin-resident bacteria actively engage host immunity through an intact skin barrier, and activate specific immune cells in a species- and strain-dependent manner. *Cutibacterium acnes* (formerly *Propionibacterium acnes*) is a gram-positive rod-shaped aerotolerant bacteria, first isolated from skin in 1897. It belongs to the order Actinomycetales, it is part of the Propionibacteriaceae family and it belongs to the genus *Cutibacterium*. This genus includes other human skin species such as *Cutibacterium avidum, Cutibacterium ranulosum* and *Cutibacterium humerusii*. *C. acnes* is one of the most prevalent and abundant bacteria on human skin and can be found both on the skin surface (stratum corneum) and in the hair follicle.

Embodiments of the present invention encompass unique combinations of probiotics, prebiotics, and other skin-beneficial ingredients. Damage to the skin epithelial barrier is a hallmark of inflammatory skin diseases, such as atopic dermatitis and psoriasis, leading to significant discomfort for individuals suffering from these indications. Epithelial barrier dysfunction can lead to translocation of environmental allergens which predispose individuals to the development of atopic and allergic disease. Additionally, epidermal barrier dysfunction (EBD) is associated with use of standard over the counter products for the treatment of acne *vulgaris*, including xerosis, pruritus, pain, and/or irritant dermatitis. EBD may also lead to an increased propensity to develop rosacea in response to environmental triggers. In certain embodiments, a *Lactobacillus* bacteria is employed to generate desired amounts of metabolites. For example, in certain embodiments, *L reuteri* and/or *L johnsonii* are employed, but most preferably, *L crispatus* is used in a beneficial bacterial composition for topical administration. Certain embodiments may incorporate live bacteria, metabolites of these bacteria, postbiotics from these bacteria, and/or heat killed bacteria.

One aspect of certain embodiments of the present invention involves the topical application of *Lactobacillus crispatus* to an individual's skin to reduce inflammation through production of tryptophan metabolites. It is believed that such tryptophan metabolites act as AHR agonists. On of skill in the art will appreciate that embodiments may incorporate live bacteria, metabolites of these bacteria, postbiotics from these bacteria, and/or heat killed bacteria.

To address the above referenced skin conditions, various embodiments of the present invention are directed to both a topical formulation and a method for using such formulation that includes skin moisturizing agents in concert with one or more live probiotic bacterial formulations and/or embodiments may incorporate live bacteria, metabolites of these bacteria, postbiotics from these bacteria, and/or heat killed bacteria. designed to reduce skin irritation, to reduce skin inflammation and to otherwise address certain skin conditions and diseases. In one particular embodiment, live bacterial cells of *Lactobacillus crispatus* are administered to the surface of an individual's skin at a dosage of at least $10^8$ CFU, preferably in a moisturizing topical formulation, so as to reduce inflammation through the localized production of tryptophan metabolites. While not bound theory, it is believed that the localized production of tryptophan metabolites by *L. crispatus* acts as AHR agonists in keratinocytes. Preferably the *L. crispatus* bacteria formulation is further combined with a source to maintain the bacteria on a person's skin for a pre-determined time. In certain embodiments, such a skin formulation includes glycogen. In still other embodiments, a prebiotic for *L. crispatus* is provided, such prebiotic which may also include glycogen, and even more preferably it further includes a stimulant for the production of ceramide by keratinocytes. The one or more skin moisturizing agents may include, for example, skin barrier integrity-enhancing ingredients, such as PEA/MEA bioactive lipids, N-acetyl cysteine, nicotinamide, luteolin, and/or madecassoside. Again, while not bound by theory, bacterial formulations of the present invention include at least one bacteria that generates metabolites that act as AHR agonists. Preferred metabolites comprise tryptophan metabolites, such as indole-3-aldehyde or indole-3-acetic acid, as well as those that may reduce inflammation and/or those that inhibit thymic stromal lymphopoietin (TSLP) in keratinocytes in an AHR dependent manner. It is believed that AhR activation may suppress upregulation of TSLP expression. In preferred embodiments, *L. crispatus* is employed under conditions such that specific metabolites are generated that act as AHR agonists, thereby resulting in the reduction of skin inflammation. In preferred embodiments the metabolites generated via the use of *L. crispatus* comprise tryptophan metabolites, including at least one of the following: indole-3-acetic acid, Indole-3-ethanol, Indole-3-pyruvate, indole-3-aldehyde. Thus, aspects of various embodiments of the present invention include the use of a live bacterial topical probiotic product that modulates AhR expression through the localized production of tryptophan-derived bacterial metabolites. Preferred topical formulations include a combination of live *L. crispatus*, prebiotic glycogen, and at least one barrier-enhancing/moisturizing compound.

In certain embodiments the invention is directed to a combination of materials that ultimately are administered to an individual so as to enhance and improve the appearance, health and function (e.g., as a barrier to undesired elements) of the individual's skin surface. Thus, in some embodiments, a particular probiotic bacteria formulation (as described in some detail herein) is combined with select peptides and human milk oligosaccharides (HMOs), also known as human milk glycans, e.g. such as can be found in high concentrations in human breast milk, to facilitate the generation of beneficial metabolites by the probiotic formulations. In one embodiment, collagen peptides are combined with hyaluronic acid and a probiotic strain, including at least one of a *Lactobacillus* bacteria that utilizes HMO.

In still other embodiments, bacteria are selected for application to an individual's skin are employed in view of being able to administer the same to target a particular circadian rhythm. While one focus of the present disclosure relates to barrier repair, still other embodiments are directed to topical lactobacilli and circadian rhythms thereof. The microbiome undergoes diurnal variation in composition and function, and this in turn drives oscillations in host gene expression and functions. Thus, some embodiments of the present invention are directed to affecting host-microbiome interactions by the appreciation of an individual's microbiome chronobiology so as to provide a novel therapeutic approach to treating adverse skin diseases and conditions.

Certain aspects of the present invention are focused on conditions and/or diseases induced by circadian clock disruption that can be mediated by adjusting an individual's microbiome composition and function. Thus, the timing of application of microbiota-based therapeutics, such as pre-, pro-, and post-biotics, is employed to advance the efficacies of treatments as described herein. An individual's microbial circadian rhythms due to its diurnal variation is taken into account when administering the type of bacterial formulations to a person's skin to arrive at preferred therapeutic responses. This timing of microbiota-based therapeutics provides a unique method for addressing skin conditions and diseases in a fashion previously unappreciated by those of skill in the art, thus permitting the correction of previously unaddressed dysregulation of an individual's circadian rhythm associated with aging or chronic illnesses, paying attention to such modifications in terms of the diurnally shifting microbiome.

In certain preferred embodiments, *L. crispatus* is employed and administered to an individual's skin surface (especially outside the vagina) to address certain skin conditions and diseases as described herein. Preferably, *L. crispatus* is combined with a prebiotic, preferably glycogen, in an amount sufficient to sustain the *L. crispatus* for at least one hour after application to an individual's skin in a manner that treats a skin condition/disease, such as acne.

In various embodiments, the timing of bacterial and prebiotic and probiotic applications form aspects of the patentable inventions set forth herein. For example, contacting one's skin with a cleanser, such as an alcohol, to first remove or kill certain bacteria; followed by a prebiotic; followed by a probiotic; and then a further different probiotic bacteria that thrives in the environment generated by the first probiotic, is involved in several of the particular embodiments of the present invention.

As discussed herein, aryl hydrocarbon receptor (AHR) is a ligand-activated receptor expressed in many cell types, including intestinal epithelial cells. Such agonists include metabolites of tryptophan such as kynurenine (KYN) and/or kynurenic acid (KYNA). Moreover, bacterial metabolites such as SCFAs modulate AHR activity, sometimes not directly as ligands, but nevertheless in a manner to stabilize and facilitate AHR actions. AHR is believed to act as a mediator in the communication between the host and a microbiome of the host, e.g., its gut microbiota. AHR is believed to be activated by microbial-specific metabolites of dietary tryptophan.

In certain embodiments, removing or selectively killing certain bacteria on an individual's skin, followed by purposeful contact of such skin with a pre-selected bacterial composition, is one aspect of the present invention.

A number of inflammatory diseases have manifestations in the skin and/or mucosa, including psoriasis (Ps), atopic dermatitis (AD), contact dermatitis, hidradenitis suppurativa (HS), pyoderma gangrenosum (PG), Sweet's syndrome, mutations in the PSTPIP-1 gene (PAPA syndrome, PAPSH syndrome and PASH syndrome), Bechet's disease, bullous pemphigold, mucous membrane pemphigold, pemphis *vulgaris*, cutaneous Crohn's disease, Sjögren syndrome, systemic lupus erythematosus, prurigo nodularis (PN), *Pityriasis lichenoides* chronica, palmoplantar pustulosis (PPP), pyoderma gangrenosum (PG) and erythoderma. Many of these diseases are associated with rheumatoid arthritis and inflammatory bowel diseases, suggesting a common underlying pathophysiology.

Aryl hydrocarbon receptor (AhR) agonists have been used clinically to treat auto-inflammatory diseases including ulcerative colitis, multiple sclerosis, atopic dermatitis and psoriasis. AhR agonists include, for example, compounds such as indigo and indigo derivatives including, indirubin, meisoindigo, natura-alpha (glycosylated isoindigotin); clinical-stage drugs such as tapinarof, linomide (roquinimex) and laquinimod; regulatory approved drugs such as itraconazole, ketoconazole, omeprazole, and leflunomide; naturally occurring compounds such as FICZ (5,11-dihydro-indolo[3,2-b]carbazole-6-carboxaldehyde, 6-Formylindolo[3,2-b] carbazole) and indole derivatives; and polyaromatic hydrocarbons such as 2,3,7,8-tetrachlorodibenzo-p-dioxin (TCDD), coal tar, refined coal tar, and components of tobacco combustion. While there has been some use of AhR agonists for the treatment of psoriasis and atopic dermatitis, AhR agonists have not been used clinically to treat auto-inflammatory diseases that manifest in the skin.

Certain embodiments of the present invention include the use of particular bacterial compositions that include *Prevotella* to treat certain skin conditions or diseases, including psoriasis and atopic dermatitis. Preferably, certain strains of *Prevotella* are employed, alone or in combination with *L. crispatus* bacteria, and preferably those bacteria that have been modified using CRISPR systems to remove one or more virulence factors. Other embodiments include methods of decreasing inflammation in an individual suffering from a skin condition or disease. Administering to an individual a bacterial composition described herein, is done to decrease the level of inflammation by the individual.

Another aspect of certain embodiments of the present invention is directed to the treatment, reduction and/or prevention of the skin condition acne *vulgaris*. *C. acnes* is the most abundant bacteria in the pilosebaceous follicle both in healthy patients and in patients with acne. There are no differences in terms of bacterial load and thus, the functionality of *C. acnes*, rather than just its presence in acne lesions, is important. Certain aspects of the present invention are directed to the modification of the functionality of *C. acnes*, e.g. via employment of CRISPR systems to affect virulence factors of *C. acnes*, thus enabling *C. acnes* to remain present on the skin, but devoid of undesired functional aspects thereof. As such, certain embodiments of the present invention are directed to the modification of *C. acnes* to remove or reduce the influence of one or more virulence factors of *C. acnes*. Preferably, such modifications are achieved using a CRISPR system as herein described. Moreover, the purposeful administration of such modified *C. acnes* to an individual's skin is intended to competitively compete with and/or inhibit other bacteria on an individual's skin, including any *C. acnes* that may remain after a pre-cleansing of an individual's skin to attempt to reduce the population of un-modified bacteria.

*C. acnes* is the most abundant skin commensal of the human skin microbiome and a major component of healthy skin. This exposes a common misconception that an individual's microbiome consists of "good bugs and bad bugs" and that all one needs to do is to kill the bad bugs. This is incorrect. Instead, various embodiments of the present invention relate to modifying bacteria that may commonly be deemed to be undesirable or "bad," and modifying the same so that the beneficial aspects of such bacteria can be retained while the undesired aspects of such bacteria are reduced or eliminated. Various embodiments involve the reduction or elimination of virulence factors of otherwise pathogenic bacteria. Competitive advantages can be provided to certain modified bacteria that permits them to outcompete other bacteria on a person's skin so as to provide desired benefits of certain bacteria, including the provision and generation of desired metabolites for the skin and/or for other desired populations of bacteria. Thus, one aspect of the present invention relates to preserving the health benefits of *C. acnes* to healthy skin, while reducing the harmful and undesired aspects of *C. acnes* in its propagation of acne *vulgaris*. One particular virulence factor to be targeted in certain embodiments of the present invention is the virulence factor denoted the tight adherence (tad) locus. *C. acnes* is known to outcompete many other bacterial species, which may be due to its genome stability or to defense strategies that disallow genetic changes. *C. acnes* clade II strains contain full CRISPR/Cas type I-E systems with spacers matching phages. In comparison, *C. acnes* clade I has lost big parts of such systems over time, indicating that they represent a more recent evolutionary lineage compared to clade II strains. Phages within the skin modulate skin microbiome composition by infecting either a narrow range of strains or broadly within a population. It is believed that a healthy skin microbiome harbors more phages than an unhealthy one and *C. acnes* harbors multiple temperate and lytic phages. Thus, various embodiments of the present invention include the modification of either *C. acnes* or bacteriophages thereof to provide a more healthy skin bacterial population.

A link exists between the presence of intestinal dysbiosis and the imbalance of skin homeostasis, with the intestinal microbiota playing a role in the pathogenesis of several inflammatory skin diseases. While the human intestine houses 70% of the body's immune cells, the skin is also rich in immune cells and is densely colonized by bacteria and there is a bidirectionality between the intestinal microbiota and skin homeostasis. Thus, while the intestinal microbiota has a major influence one's immune system, the skin microbiota is important in maintaining an adequate immune homeostasis of an individual's skin.

The severity of acne is at least partially due to an inflammatory response related to the presence of *C. acnes*, as well as an excess of sebum, hormonal influences, immune responses influenced by the intestinal microbiota, and/or an individual's genetic predisposition. The present inventors contend that the presence of *C. acnes* with virulence factors in acne lesions is one reason for the different frequency of appearance of different phylotypes in acne lesions. *C. acnes* has a constant core region and a variable region in its DNA sequence, and thus the variable region is believed to dictate the observed variability with respect to its commensal and pathogenic phenotypes and its consequential influence on the development of acne. Among the important virulence factors of *C. acnes* are five Christie-Atkins-Munch-Petersen (CAMP) factors identified in the genome of all *C. acnes*. These are secreted toxins that cause the formation of pores in the membranes and are potentially cytotoxic to keratinocytes and macrophages, causing inflammation of the skin. Porphyrins are metabolites that generate reactive oxygen species (ROS) and can lead to inflammation in keratinocytes. *C. acnes* phylotypes related to acne produce more porphyrins. The generation of ROS activates inflammatory processes, such as lipid peroxidation of sebum lipids. Because virulent strains of *C. acnes* that are associated with acne produce porphyrins, it is believed that Vitamin B12 supplementation may be counterproductive in acne patients as porphyrins are involved with Vitamin B12. In various embodiments of the present invention, an individual does not take Vitamin B12 supplementation in order to reduce the incidence of acne *vulgaris*.

There are two variants of hyaluronate lyase found in *C. acnes*: HYL-IB/II and HYL-IA. Hyaluronate lyase is an enzyme capable of degrading hyaluronic acid and other glycosaminoglycans from the extracellular matrix of skin cells, contributing to inflammation in acne lesions. HYL-IA performs an incomplete degradation of hyaluronic acid, while HYL-IB/II causes a complete degradation thereof. Various embodiments of the present invention involve the reduction or elimination of hyaluronate lyase in *C. acnes*, preferably HYL-IA.

Another virulence factor of *C. acnes* includes lipases. Lipases are enzymes that metabolize lipids of the sebum, generating FFAs. It has been shown that *C. acnes* encodes 12 lipases, including glycerol-ester hydrolase A (GehA) and B (GehB), which are present in strains of *C. acnes*. *C. acnes* lipases are important in the context of acne because they are involved in the production of FFAs that promotes inflammation. Various embodiments of the present invention involve the reduction or elimination of lipases, including one or more of glycerol-ester hydrolase A (GehA) and B (GehB).

Other virulence factors of *C. acnes* associated with acne are the enzymes neuraminidase, PUFA isomerase, gliycosidase, sortase F, and RoxP, heat-shock proteins and dermatan-sulfate-binding adhesins. Various embodiments of the present invention involve the reduction or elimination of these virulence factors, preferably employing CRISPR systems to do so.

Strains that belong to phylotype II of *C. acnes* are most associated with healthy skin while phylotype I strains are most associated with acne lesions. The latter usually present deletions in regions of CRISPR/Cas sequences, which implies a greater capacity to acquire virulence factors through horizontal transmission.

The ability to form biofilms, i.e. a structured colony of bacterial cells embedded in a polymer matrix that is manufactured by the bacteria and adhered to a surface, is a particularly important virulence factor of *C. acnes*. Biofilms formed by *C. acnes* are significantly higher in acne lesions than in the skin of healthy controls. Formation of biofilms by *C. acnes* is at least partially due to the presence of genes involved in such formation, such as glycosyltransferases and uridine diphosphate N-acetylglucosamine 2-epimerase. Thus, in certain embodiments the present invention is directed to the reduction or elimination of these genes, preferably employing CRISPR systems to do so. As the presence of biofilms is associated with a greater resistance to antibiotics due to the presence of an exopolysaccharide matrix that prevents or hinders the interaction of an antibiotic to its molecular target, the reduction or elimination of biofilms forms one aspect of the present invention as it relates to the treatment of *Acnes valgaris*.

Certain embodiments are directed to treating an individual suffering from acne valgaris, by using a clustered regularly interspaced short palindromic repeats (CRISPR) CRISPR associated protein (Cas) to selectively kill or retard the growth of a pathogenic bacteria within the individual, the pathogenic bacteria selected from the group consisting of *Staphylococcus aureus; Pseudomonas aeruginosa; Klebsiella; Streptococcus; Salmonella; Shigella; Mycobacterium tuberculosis; Enterococcus; E coli; Clostridium; Neisseria gonorrhoeae; Acinetobacter baumannii*; and *Campylobacter*, and thereafter enhance the growth of a beneficial bacteria in the individual selected from the group consisting of *C. acnes, Akkermansia, Bacteroides, Bifidobacterium, Fusobacterium, Coprococcus, Lactobacillus, Propionibacterium, Ruminococcus, Veillonella, Prevotella*, and *Streptococcus* bacteria. Still other embodiment are directed to treating acne valgaris by administering to the skin of an individual at least two probiotic strains in a concentration of at least $1 \times 10^8$ via AFU, with the at least two probiotic strains being either live or heat-killed and selected from the group consisting of *Cutibacterium, Staphylococcus, Corynebacterium, Micrococcus* spp., Actinobacteria, Proteobacteria, and Firmicutes. Other embodiments are directed to treating acne valgaris by administering at least one probiotic strain to an individual's skin that does not upregulate innate immune response genes selected from the group consisting of CXCL1, CXCL3, CXCL8, CXCL10, wherein the strains are either live or heat-killed. Yet other embodiments are directed to treating acne valgaris by administering to an individual's skin at least one probiotic strain that does not upregulate innate immune response genes selected from the group consisting of IL10RA, PTGS2, F2RL1, TRIM29, TRAF4, LGALS3, CD55, TRIM8, CASP4, IFNGR1, ADA, NOD1, NOS2, and APP.

It should be understood that still other embodiments of the present invention include the employment of a variety of postbiotic formulations of lactobacilli, e.g. metabolites or lysates, and thus, is not limited to the use of live bacteria formulations or methods. Some embodiments involve the use of strains that are heat-killed. Indeed, in preferred compositions and formulations, in addition to the bacterial aspects and metabolite inclusions of described products, there are additional ingredients, such as skin moisturizing agents as described herein and in references incorporated herein by reference, with several compositions including heat killed bacteria.

Still other embodiments are directed to compositions, systems and methods of improving the health of the microbiome of an individual's skin and treating an individual suffering from acne valgaris by administering topically a composition that includes live bacteria selected from the group consisting of *L. reuteri, L johnsonii, L crispatus, C. acnes*, and *Nitrosomonas eutropha*, that have been modified by using a using a clustered regularly interspaced short palindromic repeats (CRISPR) CRISPR associated protein (Cas) system or a CRISPR from *Prevotella* and *Francisella* 1 (Cpf1) system to reduce the production of a virulence factor of the bacteria.

One aspect of various embodiments of the present invention relates to the use of postbiotics, as it is appreciated that probiotics are not necessarily related to their viability, given that dead cells can confer biological responses equal or superior to their live counterparts. Thus, compounds/molecules derived from inactivated probiotics can be obtained either from metabolites generated during microbial growth or from intact (i.e., inanimate) dead strains after cell disruption and fragmentation. An abundant and diverse community of bacteria, viruses, eukaryotes, such as fungi and arthropods, make up the human skin microbiota. The diversity and abundance thereof varies considerably between individuals and between different sites on the skin, due to different genetics, diet, lifestyle, gender, age, ethnicity, and habitat. Use of dead cells, such as heat treated bacteria, may often provide the benefits of such diverse community without undesired growth of living cells on a person's skin. In addition to bacteria, fungi, especially *Malassezia, Rhodotorula, Debaromyces, Cryptococcus*, and *Candida*, act as fungal skin commensals. Different areas of an individual's skin include fungal microbes, such as Arthrodermataceae, *Aspergillus, Rhodotorula, Cryptococcus, Chrysosporium, Candida, Penicillium, Leptosphaerulina, Phoma, Saccharomyces, Ustilago*, and *Epicoccum*. The skin virome can also contribute to the health and disease status of the host through the suppressive actions of bacteriophages, such as Siphoviridae, Podoviridae, and Myoviridae, and particularly phage species, *Acinetobacter* phage Presley and *Pseudomonas* phage O4, present on healthy skin. One objective of various embodiments of the present invention is directed to the goal of maintaining the careful balance of the skin microbiome relationship such that the commensal skin microbiota can act to inhibit the spread of opportunistic parasites, which can breach the skin barrier and cause a shift from commensalism to pathogenicity, thereby developing skin conditions such as acne, atopic dermatitis and psoriasis.

The microbiome also changes with age of an individual, with *Corynebacterium, Chryseobacterium*, and *Veillonella* being present in older age groups, while younger age groups have populations of *Alistipes, Prevotella, Porphyromonas, Sphingobacterium, Lactobacillus Aerococcus*, Oscillospira, and *Ruminococcus*. In addition to the selective modification of an individual's skin microbiome using live bacteria, etc., aspects of the present invention are directed to the employment of postbiotics, such as bacteriocins, short-chain fatty acids (SCFA), organic acids, and tryptophan, many the by-products of microbial metabolism, to confer anti-inflammatory, antimicrobial, antioxidant, and immunomodulatory effects. In various embodiments of the present invention, postbiotics offer several advantages over probiotics, such as a longer shelf life, stability over a wide temperature and pH range, no ability to transfer antibiotic resistances, and the use in immunosuppressed individuals. Postbiotics eliminate the need to maintain viable cells and thus, they can be readily incorporated into formulations, such as in cosmetics.

With respect to various embodiments that relate to skin cosmetic products, the following may be included: water, surfactants that have amphiphilic substances with the capability to reduce the surface between liquids with different polarities due to the presence of both hydrophobic and hydrophilic moieties in their chemical structure; preservative and barrier agents that reduce water loss; enhancers, such as denatured alcohol, glycols, and esters, which improve the penetration of active ingredients through lipid fluidization, lipid extraction, and lipid ordering mechanisms; and humectants that improve the hydration of the skin surface through the attraction of water from lower layers and posterior fixation in the stratum corneum via formation of hydrogen bounds.

Certain embodiments of the present invention are directed to the appreciation that the skin microbiome changes across one's lifespan, reflected in the dynamic shifts of the skin microbiome's diverse, inter-connected community of microorganisms with age. The precise community composition for any individual person is determined by local skin physiology, genetics, microbe-host interactions, and microbe-microbe interactions. Hormone fluctuations and immune system maturation also drive age-dependent changes in skin physiology that support different microbial community structures over time. While there is no single definition of a balanced skin microbiome, at a microenvironment level, balance is dictated by the skin niche along with complex host immune-microbe and microbe-microbe interactions. Distinct skin changes, such as a decline in collagen synthesis, extracellular matrix fragmentation, and a reduction in skin cell regeneration occurs as we age, with such changes manifesting themselves as skin wrinkles. Such aging related changes also shape microbiome composition, as the skin barrier loses its ability to retain water, resulting in a compensatory increase in natural moisturizing factor production, which is associated with greater abundance of numerous taxa, such as *Corynebacterium, Micrococcus, Streptococcus, Anaerococcus*, and a reduction in *Cutibacterium*. After menopause, females see a loss of *Cutibacterium* and an increase in *Corynebacterium, Streptococcus, Acinetobacter*, and *Corynebacterium*. Males, in contrast, maintain greater *Cutibacterium* abundance as they age.

Certain aspects of the present invention relate to supplementing the skin microbiome with topical probiotics derived from *Lactobacillus*, the topical application of anti-microbial peptides; bacteriophages that strategically infect *C. acnes*, and the use of oral antibiotics to modulate the gut microbiome and indirectly alter the skin microbiome. Another aspect relates to the generation of free fatty acids on the surface of the skin to create a low-pH environment (pH 4-6), deemed essential for barrier homeostasis as acidic skin pH is crucial for the activity of epidermal enzymes required for lipid processing and regulating cohesion proteins to preserve the stratum corneum and maintaining hydration levels. Low skin pH conserves the commensal skin microflora and thus acts a first-line defense against pathogens through direct competition.

Thus, one aspect of the present invention relates to the modification of a person's microbiota on their skin in a manner believed to enhance the overall health of the skin, thus preventing diseases that may otherwise infect such person's skin. The diversity of the skin formulations as set forth herein include compositions that include at least the following (and particularly such species modified via CRISPR systems to reduce their respective virulence factors and to enhance their abilities to out compete other bacteria on a person's skin): Proteobacteria, of the *Janthinobacterium, Serratia, Halomonas, Stenotrophomonas, Delftia*, and *Comamonas* genera; Actinobacteria, including species of the genera *Corynebacterium, Kocuria, Propionibacterium, Microbacterium*, and *Micrococcus*; Firmicutes, such as *Staphylococcus* or *Clostridium* species; and Bacteroidetes, including Sphingobacterium or *Chryseobacterium* species. In other embodiments, a common core skin microbiome is derived from healthy human subjects, and then such bacteria are enhanced via CRISPR-Cas systems to remove virulence factors, prior to administering the modified bacteria to a person's skin for the purpose of improving the skin microbiome thereof.

The general *Pseudomonas* and *Janthinobacterium* (both pseudomonads; gram-negative bacilli, aerobic, non-spore forming, motile by means of one or more flagella) are not typically thought of as skin microbes based on culture assays. Pseudomonads (and other Gram-negative bacilli) have historically been labeled as secondary invaders of wounds, most commonly referring to the colonization of burns by *Pseudomonas aeruginosa*. Pseudomonads are found in soil, water, and decomposing organic materials where there is a moist environment. Modification of such bacteria so that it is less virulent and more readily reduced in number due to CRISPR-Cas enhanced antibiotic sensitivities, forms one embodiment of the present invention, and one that can be employed to treat wound infections to competitively inhibit non-modified strains from infecting a wound.

Aspects of various embodiments of the present invention relate to a method to topically administer a composition of probiotic strains of bacteria, post-biotic metabolites, or other skin-specific compounds to modulate, restore, and/or support a 'healthy' or normal skin microbiome and skin barrier microenvironment, defined as populational normal skin barrier function, tight junction maintenance, skin hydration, normal filaggrin, NMF, and PCA levels, low/no colonization of pathogenic bacteria, fungi and other microorganisms, colonization of beneficial bacteria, and normal levels of inflammation and immune activity; otherwise characterized as a microenvironment that does not exhibit clinical representations or symptoms of disruption, including manifestations of atopic dermatitis, psoriasis, ichthyosis, acne, vitiligo, *Tinea versicolor*, and seborrheic dermatitis. Particular embodiments are directed to compositions of at least one probiotic strain that reflects the genomic diversity found in healthy skin microbiomes that are resistant to pathogen colonization.

Other compositions of at least one probiotic strain are selected to regulate skin microbiome ecology by utilizing sebum without producing proinflammatory metabolites or byproducts. Certain formulations produce lipases that break down sebum lipids into fatty acids which acidify the surface of the skin. In certain embodiments, compositions include at least one probiotic strain with broad anti-inflammatory activity, preferably those strains which have no proinflammatory response on the skin, and that are protective to tight junction proteins and the skin barrier. Compositions may consist of single strains or multi-strain ecologies that do not upregulate innate immune response genes such as CXCL1, CXCL3, CXCL8, CXCL10, in addition to other innate immune response genes like IL10RA, PTGS2, F2RL1, TRIM29, TRAF4, LGALS3 at 1:10,000 dilution, and CD55, TRIM8, CASP4, IFNGR1, ADA, NOD1, NOS2, APP, in addition to single strain or multi-strain compositions that down-regulate these pathways. Other compositions of single strains or multi strain ecologies do not upregulate cytokine genes, including the epithelial alarmin TSLP, and CCL20, VEGFA, IL18, and IL23.

Other compositions are directed to a single strain or multi-strains that down-regulate these pathways. Still other compositions include at least one probiotic strains which regulate filaggrin protein expression and/or degradation and therefore regulate skin moisture. Yet others are present in combination with medium chain triglycerides and/or fatty acids to inhibit fungal growth and biofilm formation, specifically of the genus *Malassezia*. Various formulations include postbiotic metabolites, for example individual fatty acids, produced from sebum metabolism by *Cutibacterium* which are applied to skin in order to regulate inflammatory activity of a native skin microbiome. Other embodiments provide postbiotic metabolites, for example individual fatty acids, produced from sebum metabolism by *Cutibacterium* which are applied to skin in order to regulate skin pH to inhibit pathogens.

In addition, and as discussed herein, the application of postbiotic metabolites, for example individual fatty acids, produced from sebum metabolism by *Cutibacterium*, are applied to skin in order to regulate skin moisture, hydration, and barrier properties. Still other formulations include compounds found in cellular debris and are purified to modulate the skin microbiome, including nutrients available on the skin purified from cellular debris rich in proteins and lipids resulting from desquamation, or sloughing, of the cornified layer of the epidermis through a process of terminal differentiation.

Certain embodiments include formulations designed to cleave sebum triglycerides and free glycerol, specifically via the administration of *C. acnes* adapted to the nutrient conditions of the human pilosebaceous unit C to secrete an extracellular lipase that cleaves sebum triglycerides, thus freeing glycerol as a growth substrate and free fatty acids that further acidify the skin, and prevent colonization by more pathogenic microbes. In certain embodiments, compositions include at least one probiotic strain from healthy skin that are capable of inducing the anti-inflammatory cytokine IL-10 in the skin. Yet others include either live, heat killed, or post-biotic skin applications of coagulase-negative *Staphylococcus* (CoNS) species, largely comprised of *S. epidermidis, S. capitis, S. caprae, S. hominis, S. lugdunensis*, and *S. haemolyticus*, designed to reduce abundance of *S. aureus*.

Certain embodiments are directed to compositions that repair and/or enhance the skin microbiome to achieve or return skin to a normal/optimal state, etc.; and will include the use of compositions that include live bacteria products (LBPs), heat-killed bacteria, post-biotics, and/or abiotic augmentations (i.e. fatty acids).

Other aspects of various embodiments of the present invention are directed to addressing the issue of skin aging, especially directed to where there are changes in the ceramides content of skin. Ceramides are the main component of the stratum corneum of the epidermis layer of human skin. Ceramides are a family of waxy lipid molecules and a ceramide is composed of sphingosine and a fatty acid. Together with cholesterol and saturated fatty acids, ceramide creates a water-impermeable, protective organ to prevent excessive water loss due to evaporation as well as a barrier against the entry of microorganisms. As a bioactive lipid, ceramide has been implicated in a variety of physiological functions including apoptosis, cell growth arrest, differentiation, cell senescence, cell migration and adhesion. With aging, there is a decline in ceramide and cholesterol in the stratum corneum of humans.

Aspects of the present invention relate to compositions of probiotics that reduce the appearance of skin fine lines and wrinkles, increases hydration, increase ceramide production, increase collagen production, reduce inflammation, improve wound healing, improve skin barrier function, improve skin elasticity, improve stratum corneum flexibility, and reduce and slow down processes associated with skin aging. Such compositions may include metabolites derived from the skin microbiome of healthy individuals and may further include one or more prebiotic compounds that support the growth and fermentation of skin bacteria producing such metabolite(s); bacteria. Certain embodiments are directed to compositions of probiotics and postbiotics that increase the production of ceramide and/or cholesterol in the stratum corneum of humans.

Various embodiments of the present invention are directed to a method of reducing the likelihood of a skin condition that causes skin inflammation in an individual human being by administering to a region of an individual's skin a therapeutically effective amount of a bacterial formulation that includes at least one bacteria selected from the group consisting of *L. reuteri, L. johnsonii, L. crispatus, Cutibacterium acnes*, and *Nitrosomonas eutropha*. Preferably the bacterial formulation is in the form of a lotion, ointment or gel adapted to be rubbed onto a region of the individual's skin, and more preferably includes abiotic augmentations that include fatty acids.

In certain embodiments, to achieve desired bioactive properties, some probiotics are not necessarily related to their viability, and thus, dead cells can confer biological responses equal or superior to their live counterparts. As such, certain embodiments include the use of heat-killed bacteria in place of or in concert with live bacteria. Such postbiotics, which are typically compounds/molecules derived from inactivated probiotics, include preparations of inanimate microorganisms and/or their components that confers a health benefit on the host. Postbiotics can be obtained either from metabolites generated during microbial growth or from intact (i.e., inanimate) dead strains after cell disruption and fragmentation. Examples of agents that possess bioactive properties of postbiotics responsible for the beneficial effects on host health include bacteriocins, lipoteichoic acids, surface layer proteins, peptides, polysaccharides, and organic acids.

In other embodiments, a bacterial formulation further comprises *Janthinobacterium*, and such formulation is present in an amount effective to treat, inhibit or reduce a skin condition from the group consisting of eczema, atopic dermatitis, acne, allergic inflammation, ultra-violet-induced skin damage, and skin hypersensitivity. Preferred methods further employ administration of a prebiotic, a metabolite, and/or a postbiotic.

In various embodiments, at least some bacteria in the bacterial formulation have been modified by using a using a clustered regularly interspaced short palindromic repeats (CRISPR) CRISPR associated protein (Cas) system or a CRISPR from *Prevotella* and *Francisella* 1 (Cpf1) system to reduce the production of a virulence factor by at least one of the live bacteria that may be in the bacterial formulation.

Certain embodiments include primarily *C. acnes* together with bacteria that produce short-chain fatty acids, such as propionate, acetate, butyrate and valerate. Preferred bacterial formulations are configured to one of the following: suppress the growth of *S. aureus*; reduce the colonization of *S. aureus* on the individual's skin; and inhibit biofilm formation by *S. epidermidis*.

Still other embodiments include the selective killing or retarding the growth of a pathogenic bacteria within the individual, with such pathogenic bacteria selected from the group consisting of *Staphylococcus aureus; Pseudomonas aeruginosa; Klebsiella; Streptococcus; Salmonella; Shigella; Mycobacterium tuberculosis; Enterococcus; E coli; Clostridium; Neisseria gonorrhoeae; Acinetobacter baumannii*; and *Campylobacter*. Yet other embodiments are directed to enhancing the growth of a beneficial bacteria, such as *C. acnes, Akkermansia, Bacteroides, Bifidobacterium, Fusobacterium, Coprococcus, Lactobacillus, Propionibacterium, Ruminococcus, Veillonella, Prevotella*, and *Streptococcus* bacteria.

Preferably, methods involve administering at least two probiotic strains to an individual's skin in a concentration of at least $1\times10^8$ via AFU, with the probiotic strains being either live or heat-killed and selected from the group consisting of *Cutibacterium, Staphylococcus, Corynebacterium, Micrococcus* spp., Actinobacteria, Proteobacteria, and Firmicutes. In certain embodiments, a probiotic strain is administered on the skin that does not upregulate innate immune response genes selected from the group consisting of CXCL1, CXCL3, CXCL8, CXCL10. In others, a probiotic strain is administered that does not upregulate innate immune response genes selected from the group consisting of IL10RA, PTGS2, F2RL1, TRIM29, TRAF4, LGALS3, CD55, TRIM8, CASP4, IFNGR1, ADA, NOD1, NOS2, and APP.

As one of skill in the art will appreciate, the methods of the present invention include different combinations of strains being applied to a person's skin, such as a therapeutically effective amount of a bacterial formulation comprising *L crispatus*, and at least two bacteria selected from the group consisting of *L. reuteri, L. johnsonii, Cutibacterium acnes, Janthinobacterium* and *Nitrosomonas eutropha*, together with abiotic augmentations of fatty acids, and wherein heat-killed bacteria are employed to address skin conditions such as eczema, atopic dermatitis, acne, allergic inflammation, ultra-violet-induced skin damage, and skin hypersensitivity. In certain embodiments, the bacterial formulation includes bacteria from the group of *Faecalibacterium prausnitzii, Bifidobacterium, Lachnospira, Veillonella, Coprococcus, Akkermansia muciniphila* and *Rothia*. Still further embodiments include more than just a bacterial formulation, and include the administration to a person's skin an extract derived from a helminth from the group of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus*, and *Trichinella spiralis*. In preferred embodiments, the methods involve the use of a bacterial formulation that generates an amount of tryptophan metabolites sufficient to act as aryl hydrocarbon receptor (AHR) agonists to thereby reduce inflammation on the individual's skin.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications.

BRIEF DESCRIPTION OF THE DRAWINGS

FIG. 1 is a picture of *Faecalibacterium prausnitzii*.
FIG. 2 is a picture of *Akkermansia muciniphila*.
FIG. 3 is a picture of *Roseburia*.
FIG. 4 is a picture of *Clostridium*.
FIG. 5 is a picture of *Veillonella*.
FIG. 6 is a picture of *Prevotella*.
FIG. 7 is a picture of *Propionibacterium*.
FIG. 8 is a picture of *Pseudomonas aeruginosa*.
FIG. 9 is a picture of *Klebsiella*.
FIG. 10 is a picture of *Shigella*.
FIG. 11 is a picture of *Acinetobacter baumannii*.
FIG. 13 is a picture of *L. crispatus*.
FIG. 14 is a picture of *Lactobacillus reteri*.
FIG. 15 is a picture of *Lactobacillus johnsonii
*
FIG. 16 is a picture of *Nitrosomonas eutropha*.
FIG. 17 is a picture of *Cutibacterium acnes*.

DETAILED DESCRIPTION OF PREFERRED EMBODIMENTS OF THE INVENTION

Figure 12:
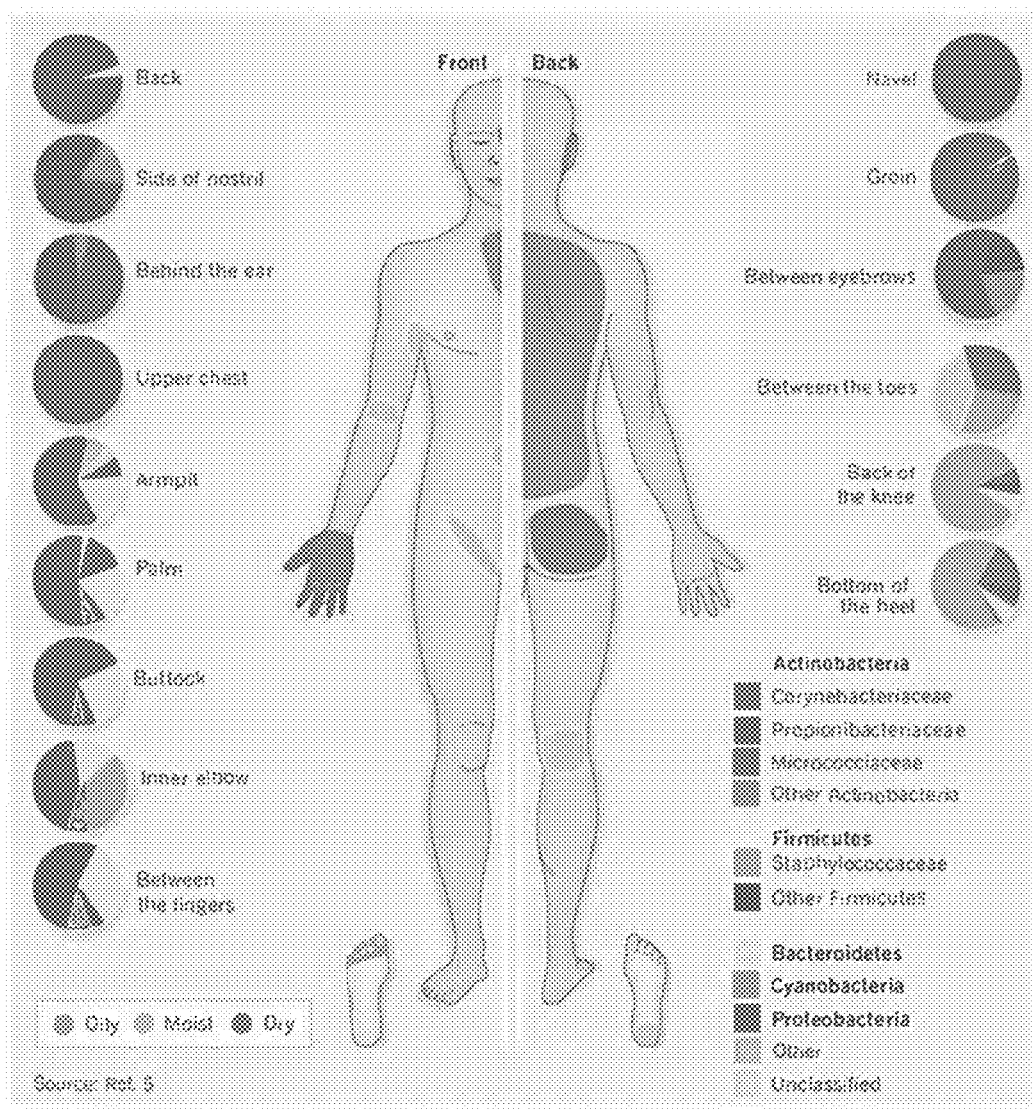
FIG. 12 shows where various bacteria reside on the human skin, which varies by region of the body and that depends upon whether the skin site is oily, moist or dry.

The present invention stands in contrast to accepted methods of dealing with skin and bacteria issues (which largely solely involve killing bacteria, etc.—such as described in Kimberly Clark's U.S. Pat. No. 8,110,215 to Koenig, et al.) In contrast, various embodiments of the present invention are directed to modification of various bacteria on a person's skin so as to reduce the pathogenicity thereof and to rely upon competitive inhibition of such modified bacteria on the skin to reduce the presence of pathogenic bacteria on an individual's skin.

As set forth above, in particular embodiments of the present invention, contacting the skin of a newborn is performed to address the proper triggering of the newborn's immune system development. Thus, certain aspects of the present invention are directed to a method for altering the microbiome of an individual's skin by administering to a region of the skin of a newborn within the first 6 hours of the newborn's birth a particular bacterial formulation. Such a bacterial formulation may be a lotion, ointment or gel adapted to be rubbed onto the newborn's skin. The bacteria included in the bacterial formulation may vary to address particular concerns or diseases. For example, the bacterial formulation may include bacteria selected from the group consisting of *Nitrosomonas eutropha* and *Propionibacterium*. More particularly, the equilibrium of a bacterial population of the region of the skin of the individual is modified to increase the number of *Propionibacterium* bacteria and to decrease the number of *Staphylococcus* bacteria on the individual's skin in such region. In other embodiments, the bacterial formulation includes the bacteria *Staphylococcus aureus* that has been modified by employing a CRISPR-Cas or Cpf1 system to interfere with *S. aureus* virulence regulation involving the Agr quorum-sensing signaling molecule. In several embodiments, the bacterial formulation comprises a bacteria that has a tropism specific for the human species. In others, the bacterial formulation comprises at least two of the bacteria selected from the group consisting of: *Prevotella; Lactobacillus johnsonii; Bacteroi-*

*des fragilis, Lactobacillus ruminus* and *L. infantis*. In certain embodiments the bacteria is an ammonia oxidizing bacteria. In other embodiments, the region of the skin to which the bacterial formulation is applied is the scalp. In various embodiments, rather than using a wild-type bacteria, the bacteria employed is one that has been modified by CRISPR-Cas or CRISPR-Cpf1 to delete a functional virulence factor from the bacteria. In particular embodiments, the method includes administering to the skin a bacteria that produces tomatidine. Some embodiments involve the application of an effective amount of a tomatidine containing formulation to an individual's skin as tomatidine is a steroidal alkaloid from solanaceous plants that possesses potent antibacterial activity against *S. aureus*. In others, the bacteria produces p53. Thus, in some embodiments, the method involves use of bacteria wherein a CRISPR-Cas or CRISPR-Cpf1 system is employed to insert a gene for the production of tomatidine and/or p53 into at least one of the bacteria in the bacterial formulation. In others, a CRISPR-Cas or CRISPR-Cpf1 system is employed to insert one or more genes into the bacteria comprising the bacterial formulation to facilitate the oxidizing of ammonia by the bacteria. To further enhance the ability of desired bacteria to be maintained on the skin of an individual, certain methods further comprise administering to the individual's skin a prebiotic that comprises a nutrient source for the bacteria that is assimilated by the bacteria, and preferably one that is not digestible by the individual. In particular embodiments, the method further includes administering to the skin an extract derived from a helminth selected from the group consisting of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus*, and *Trichinella spiralis*. In still others, the bacterial formulation includes at least one arabinogalactan. Yet others include at least one of the following: *L. infantis*, and *L. johnsonii*. In a particular embodiment, the bacterial formulation includes at least one bacteria modified via a CRISPR-Cas system to express a gene encoding interferon regulatory factor 4.

As for lotions of the present invention, in preferred embodiments, there is an objective to limit if not preclude the use of phthalates, which are extremely toxic and are believed to also be human carcinogens. Thus, in preferred embodiments of the present invention, such lotions do not employ such toxic agents, and in particular agents toxic to bacterial species for which the inventors suggest be used, e.g. those modified to reduce pathogenicity, virulence factors, etc, so as to establish a population of such modified bacteria on a person's skin, and in such a manner, reduce the incidence of skin infections and diseases. Thus, lotions, creams, gels, etc. that include such toxic agents, including but not limited to phthalates, are not employed, but rather, lotions that provide an environment for the bacteria as set forth herein to survive and to thus be available to provide benefits to the skin of individuals to which they are applied, are particularly preferred.

Healthy, normal skin exhibits a slightly acidic pH in the range of 4.2-5.6, which aids in the prevention of pathogenic bacterial colonization, regulation of enzyme activity, and maintenance of a moisture-rich environment; however, after the age of 70, the pH of skin rises significantly, stimulating protease activity. Thus, one objective of several embodiments of the present invention is directed to lowering the pH of the skin of an individual, especially those at about the age of 70, so as to encourage a skin environment conducive to the proliferation of one or more bacteria that have been modified to promote skin health and to reduce the ability of undesired bacteria from colonizing the skin of the person. Probiotic metabolism frequently produces acidic molecules, lowering the pH of the surrounding environments seen with Lactobacilli *crispatus* producing free fatty acids (FFAs) and conjugated linoleic acid (CLA) during the fermentation process. Thus, the use of probiotics is employed to restore the normal skin pH and consequently return protease activity levels closer to those seen in young, healthy skin.

The main microbes that reside on human skin can be divided into four phyla: Firmicutes, Actinobacteria, Proteobacteria, and Bacteroidetes. *Staphylococcus* spp. and *Corynebacterium* spp. are the dominant bacteria at the genus level.

Significantly fewer *Corynebacterium* spp. have been observed in cachexia patients compared to healthy subjects. These results suggest that the presence of cancer and cachexia alters human skin bacterial communities. Understanding the changes in microbiota during cancer cachexia may lead to new insights into the syndrome.

Competitive inhibition is relied upon in various embodiments to advance the repopulation of skin with beneficial microbes. In one embodiment, repopulating an individual's skin with beneficial bacteria, preferably in balanced percentages and having preferred species provided, can be used in conjunction with an antimicrobial composition. Preferably, an antimicrobial is first administered to suppress or eradicate the resident populations of bacteria on a person's skin, including any abnormal organisms or pathogenic bacteria, then the normal flora is repopulated by the administration of at least one of the modified bacteria as described herein, including those modified using CRISPR-Cas and/or Cpf1 systems to delete certain portions of genes or to add certain genes to facilitate the colonization of a person's skin with beneficial bacteria that maintain the general health of a person's skin.

It is preferred that the antimicrobial treatment is complete before the administration of modified bacteria that are desirable to maintain skin health, including modified bacteria of the following: Firmicutes (mainly *Streptococcus* and *Staphylococcus*) and Actinobacteria (mainly *Corynebacterium* and *Propionibacterium*). By employing such modified bacteria, one is able to establish and maintain the reduction if not preclusion of various skin diseases, including skin cancer. One objective of the present invention is to provide a method and system that, by using health promoting strains from the microbiome in topical probiotics, it is possible to treat and to further reduce the risk of skin cancer.

Repair of tissue wounds is a fundamental process to re-establish tissue integrity and regular function. Infection is a major factor that hinders wound healing. Multicellular organisms have evolved an arsenal of host-defense molecules, including antimicrobial peptides (AMPs), aimed at controlling microbial proliferation and at modulating the host's immune response to a variety of biological or physical insults. Certain embodiments of the present invention are directed to the use of AMPs as endogenous mediators of wound healing. Thus, one aspect of several embodiments of the present invention is directed to genetically manipulating bacterial species native to the skin. *Staphylococcus epidermidis*, which is found in abundance on human skin, can cause immune tolerance in some—but in others, inflammation and activation of T cells against the bacteria. The present inventors submit that the immune system may set up tolerance to commensal bacteria only early in life, during a time where there is an influx of regulatory T cells unique to the skin, e.g. during the first week after birth. This colonization of the skin by regulatory T cells—immune cells that dampen the responses of effector T cells—is believed to be required for tolerance to *S. epidermidis*. There is an abrupt wave of regulatory T cell infiltration into neonatal skin that occurs at a defined period and this window dictates the achievement of commensal-specific tolerance.

One aspect of the present invention is directed to the introduction of tolerance to commensal bacteria during the time the developmental window is still open, thus providing the individual with life-long protection from a variety of diseases. Still other embodiments, however, are directed to introducing tolerance following the closing of the developmental window, e.g. after the first week after birth, so that individuals can purposefully be induced to have commensal-specific tolerance as an adult. Understanding which microbes cause infection and which are tolerated and the critical time frames where the immune status is set is one aspect of the present invention.

Skin bacterial communities are influenced by ethnicity, lifestyle and/or geographic location. Skin bacterial communities that are particularly employed in the modifications as set forth herein include: Firmicutes, Proteobacteria and Actinobacteria); Firmicutes (mainly *Streptococcus* and *Staphylococcus*) and Actinobacteria (mainly *Corynebacterium* and *Propionibacterium*), while still other preferred bacteria include *L. acidophilus* NCFM, *L. salivarius* Ls-33, *Bifidobacterium lactis* 420, *L. acidophilus* La-14 and *Propionibacterium jensenii* P 63.

In various embodiments, cosmetics are provided that provide for a medium favorable for maintaining a desired physico-chemical balance of the skin without favoring the development of pathogenic microorganisms. To achieve this objective, certain oligosaccharides that are metabolized by several beneficial strains of the skin microflora, such as *Micrococcus kristinae, Micrococcus sedentarius, Staphylococcus capitis, Corynebacterium* xerosis and *Lactobacillus pentosus*, are employed in formulations, in conjunction with one or more of the modified bacteria as described herein.

Pathogenic strains such as *Staphylococcus aureus, Gardnerella vaginalis* and *Propionibacterium acnes* do not typically metabolize, or very slightly metabolize, these oligosaccharides. In certain embodiments, these sugar sources are provided in amounts and in association with beneficial bacteria, whether they be those modified as described herein, or those that are naturally non-pathogenic in nature, so as to achieve the colonization of the skin in a fashion to provide the health benefits sought. In particular embodiments, oligosaccharides are employed in formulations for the skin that include one or more of *Lactobacillus pentosus, Micrococcus kristinae, Gardnerella vaginalis, Propionibacterium avidum* and *Propionibacterium granulosum*. As stated herein above, it is often beneficial to further acidify the culture medium, and this can be achieved, for example, by employing Lactobacilli to produce in particular lactic acid to achieve pH reducing effects.

In certain embodiments, the present invention is directed to cosmetic compositions having at least one oligosaccharide chosen from the group consisting of gluco-oligosaccharides, fructo-oligosaccharides, and galacto-oligosaccharides and mixtures thereof. In addition to the oligosaccharide constituent, the cosmetic compositions of particular embodiments of the invention may contain other ingredients, but caution is warranted as one objective is to avoid incorporating ingredients whose properties would interfere with the development of the beneficial skin microflora and the preservation of acidic conditions. Thus, it is advisable to avoid incorporating bactericidal ingredients in proportions which would annihilate the endogenous microflora, or ingredients which confer a pronounced basic character on the composition. For example, in preferred embodiments, reduction if not elimination of ionic surface-active agents, such as sodium lauryl sulfate, is advisable, as well as other well-known agents having bactericidal properties. Instead, use of a non-ionic surface-active agent such as an alkyl glucoside or a dialkyl ester may be employed in various embodiments. Preferably, cosmetic compositions of the invention contain an acidic buffer which adjusts the pH of the composition to about pH 4 to 7 range, preferably about 5 to 6.5 pH. At such range, especially on the lower side, mutualistic flora such as Staphylococci, Micrococci, *Corynebacterium* and Propionibacteria preferably grow but not transient bacteria such as Gram negative bacteria like *Escherichia* and *Pseudomonas* or Gram positive ones such as *Staphylococcus aureus* or *Candida albicans*.

One aspect of the present invention relates to cosmetic products that include skin probiotics having viable organisms purposefully included, especially those genetically designed (as by CRISPR systems) so as to confer health benefits to the skin without the dangers of bacterial infections and inflammation. Indeed, certain other aspects of various embodiments are directed to the reduction of body odor by use of a probiotic skin formulation that can be provided to consumers as a lotion, spray, roll-on etc. Thus, stimulating the growth of certain bacteria and microbes, while deterring the growth of others, to arrive at an acceptable odor prevention formulation, is one of the general objectives of various embodiments.

Certain other embodiments are directed to the rebalancing of the skin microbiota using antimicrobials with selective action. For example, in certain embodiments a balance of species and characteristics is sought to provide skin formulations that maintain a well-balanced bacterial flora, and especially one that includes one or more of the modified bacteria as described herein. Thus, one particular aspect of various embodiments is directed to the provision of embodiments targeted to reduce undesired body odor (and in various embodiments, actively provides microbes that generate desired odors and reduces the effects of malodors by other bacteria) which can be gender specific.

Thus, in certain embodiments, a system and method is provided that offers the interactions between bacteria and precursors of thiols—an organosulfur compound responsible for some of the more pungent qualities of onion, garlic and human sweat. In human adults, smell associated with sweat originates from apocrine glands located in the armpit, and the odor results from the degradation of the excretion of these glands by bacteria in the armpit.

Particular embodiments are directed to anti-deodorants used specifically for under a person's arm. In various formulations of the present invention, the use of bacteria able to generate lactic acid to serve as a moisturizing factor, still others that produce hyaluronic acid to improve skin hydration and elasticity, and that include sphingomyelinase to generate ceramide to enhance skin barrier function, are preferred compositions. As one of skill in the art will appreciate, while various embodiments of the present invention are directed to cosmetics, others are admittedly directed to formulations having claims for effects that include skin protection, and modification of cellular structure or function and thus, may be considered a drug under the FD&C Act. One aspect of the present invention is directed to restoring homeostasis to treat certain skin diseases by remedying the dysbiosis in the skin habitat by establishing a desired colony of various diverse bacteria, especially those modified as described herein to establish and maintain a healthy skin condition on an individual's skin.

The antiperspirant market is currently dominated by topically applied products based on aluminum or zirconium salts which are intended to prevent, or at least control, localized perspiration at the skin surface, particularly on the underarm. Deodorants are formulations that are designed either to mask malodor or to prevent or hinder its formation. The latter method usually comprises reducing and/or controlling the re-growth of the local micro-organism populations, or targeting preferentially those bacteria such as a sub-class of Coryne bacteria which contribute disproportionately to axillary odor generation, or interrupting the pathways by which malodors are formed from secretions. Aluminum or zirconium salts provide deodorancy benefits even at a level below the commonly accepted threshold for significant antiperspirancy to be observed.

A principal disadvantage of many antiperspirants is that they contain one or more commonly employed ingredients which are perceptibly unfriendly to human skin in those areas of the body to which the formulations are normally applied. Such ingredients are perceived to exhibit an adverse effect, in particular an irritant effect, on a user's skin following application of the antiperspirant salt-containing formulation. In one embodiment of the present invention, bacteria species are employed that have been modified via CRISPR-Cas systems to reduced malodor without the employment of aluminum or zirconium salts. Such modified bacteria suppress malodor and counteract or suppress sweat malodor. Even more preferred bacteria have been modified to express compounds of a pleasant and desirable scent. Such bacteria can thus provide amounts of a perfume scent that is pleasant to a person and that can at least partially mask the unpleasant body odor smells produced by a person. Splicing in such "perfume" genes into bacteria using the CRISPR-Cas system is one way to accomplish this objective. Use of such bacteria on a person's skin, and in particular under armpits where the particular type of bacteria is selected to grow and out-complete other microbes in such a moister environment (as compared to elbows, etc.) can be used to enhance the desired smells of one's body while limiting the amount of traditional antiperspirants and deodorants conventionally employed. Still other embodiments include the use of bacteria that utilize as their food source the very bacteria that produce malodors. In such a fashion the desired bacteria feed off of the products produced by undesired bacteria on a person's skin, and in particular under an individual's arm, so that undesired body odor is reduced and without the use of traditional chemicals and compounds as previously discussed.

To further comply with written description and enablement requirements, the following patents and patent publications are also incorporated herein by this reference in their entireties: are the following: U.S. Pat. No. 8,815,538 to Lanzalaco, et al.; 20150374607 to Lanzalaco, et al.; 20150361436 to Hitchcock et al.; 20150353901 to Liu et al.; U.S. Pat. No. 5,518,733 to Lamothe, et al.; 20150259728 to Cutliffe et al. U.S. Pat. No. 8,685,389 to Baur; 20140065209 to Putaala et al.; U.S. Pat. No. 8,481,299 to Gueniche; WO 2011029701 to Banowski; 20150071957 to Kelly; 20150202136 to Lanzalaco; 20150017227 to Kim; U.S. Pat. No. 7,820,420 to Whitlock; 20150202136 to Lanzalaco et al.; U.S. Pat. No. 5,518,733 to Lamothe, et al.; U.S. Pat. No. 8,815,538 to Lanzalaco et. al; U.S. Pat. No. 8,951,775 to Castiel; WO 2006/07922; 9,234,204 to Qvit-Raz et al.; U.S. Pat. No. 8,758,764 to Masignani, et al.; U.S. Pat. No. 9,028,841 to Henn et al.; 20160008412 to Putaala et al., 20150064138 to Lu; 20150017227 to Kim; United States Patent Application No. 20160314281 to Apte; 20160151427 to Whitlock et al.; 20140044677 to Raz et al.; 20160168594 to Zhang et al. U.S. Pat. Nos. 7,267,975; 9,288,981; United States Patent Application No. 20160122806; 9234204 to Noga Qvit-Raz; US20120301452; 20160271189 to Cutcliffe; US Pat. Applic. No. 2008242543; 20160040216 to Wilder; and United States Patent Application No. 20160089315 to Kleinberg, et al. and 20070148136 to Whitlock et al.; 20200190494 to Hou, et. al.; and 2020/0199555 to Zhang; U.S. Pat. No. 9,585,920; al., 20190059314 to Aharoni; 20200009268 to Scholz and 20200009185 to Shin; US Pat. Publication No. 20190388471 to June; 20190000815 to Melin; 20180258100 to Gregory; 20170027914 to Qi; 20170079947 to Richards; 20140296139 to Cohen et al.; 20160175327 to Adams et. al.; 20100081681, 20130310416, and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr, et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S. 2002/0009520, U.S. 2003/0206995, U.S. 2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et al; and WO2015069682A2 to Asesvelt, et. al.; 20160199424 to Berry et al.; 20130326645 to Cost et al.; 2012/0276149 to Littman; U.S. Pat. No. 9,314,489 to Kelly et al.; U.S. Pat. Publication No. 2016/0024510 to Bikard et al.; U.S. Pat. Publication No. 2018/0015131 to Gajewski et al.; U.S. Pat. Publication No. 2018/0371405 to Barrangous et al. and U.S. Pat. Publication No. 2018/0140698 to Clube et al.; 20160199424 to Berry et al.; and 20130326645 to Cost et al.; 20190315642 to Parsley; 20170246269 to Hajishenfallis; 201302236488 to Dashper; 20030083287 to Burgess; 20170042860 to Kashyap; 20150045546 to Siksnys; U.S. Pat. No. 10,730,826 and 20200148642 to Konradi et. al.; 202110321756 to McLaughlin, et. al.; 20210308028 to Yang et. al.; U.S. Pat. No. 11,083,760 to Han; 20180110795 to Frias-Lopez; 202110169954 to Balani et. al.; U.S. Pat. No. 4,720,486 to Spilburg; and 20070207955 to Tanihara; U.S. Pat. No. 11,473,093 to Levenau, et. al.; 20220339208 to Abel, et. al.; 20220331375 to Kovarik; 20210361560 to Krueger, et. al.; WO2019067621 to Bardales, et. al.; 20220331374 to Richter, et. al.; 20220339208 to Abel, et. al.; 20220023259 to Davidson et. al.; 20180235987 to Von Maltzahn, et. al. and WO 2022/187274 to Ratti; U.S. Pat. No. 11,364,214 and 2022/0000760 to Raochova.

Skin is composed of a variety of niches, including regions with a broad range of pH, temperature, moisture, and sebum content. Furthermore, skin structures such as hair follicles, sebaceous, eccrine, and apocrine glands comprise subhabitats that may be associated with their own unique microbiota. Microorganisms that colonize the skin include *Staphylococcus epidermidis* and other coagulase negative staphylococci. Other microorganisms that are generally regarded as skin colonizers include coryneforms of the phylum Actinobacteria (the genera *Corynebacterium, Propionibacterium* and *Brevibacterium*) and the genus *Micrococcus*. Modification of such bacteria via CRISPR-Cas and/or Cpf1 systems to enhance positive and beneficial aspects of such bacteria is one aspect of various embodiments of the present invention.

One aspect of certain embodiments is directed to the topical administration of probiotic bacteria, and/or soluble metabolites of probiotic bacteria and/or a cell lysates of probiotic bacteria that can improve Tight Junction (TJ) function in the epithelium. The probiotic bacteria is preferably provided in the form of a soluble metabolite with a formulation in a cream, lotion, spray, solution, gel, ointment, bioadhesive or suspension, or strip, especially one having encapsulated formulations inside. The formulations described herein are markedly different from natural counterparts due to their modification, e.g. via CRISPR-Cas systems as described herein. While some embodiments are directed to a product, others are directed to a method, and thus, the later are not all limited to the products described herein.

Thus, in one embodiment the invention relates to a cosmetic method for treating a non allergic irritant contact dermatitis of an individual in need thereof by administering to an individual an active agent comprising an effective amount of at least one a probiotic microorganism selected from the genus *Lactobacillus* sp. and/or *Bifidobacterium* sp., preferably *Lactobacillus johnsonii* to limit skin irritation, and in particular, a skin infection caused by methicillin-sensitive *Staphylococcus aureus*. Administration is preferably by topical application of a pharmaceutical composition comprising at least about 1.5% by weight of the bacterium.

The skin is a natural barrier to the penetration of foreign substances. As the skin barrier is compromised, the skin is subject to inflammatory events from percutaneous absorption of irritants through the stratum corneum. Skin barrier function can be compromised by environmental irritants, mechanical abrasion, continuous tissue load pressure, exposure to body fluids and waste such as proteases, ureases and lipases, and especially those that cause an alkaline pH, and exposure to chemicals. Personal care products are an integral part of people's routines and habits, and thus, one aspect of the present invention is to provide skin probiotics to contribute to the promotion of human health.

*Staphylococcus epidermidis* and *Staphylococcus aureus* make up about 5% of skin bacteria, with the diverse culture on the skin also including bacteria primarily from four phyla: Actinobacteria, Firmicutes, Proteobacteria, and Bacteroidetes. It is known that females generally have more *Staphylococcus* living in their skin microbiomes (usually *Staphylococcus epidermidis*) and that men have more *Corynebacterium* living in their skin microbiomes.

Properly adjusted, the skin microflora can aid in immunity development and maintenance. In certain embodiments, CRISPR-Cas or Cpf1 systems are employed to modify *Pseudomonas aeruginosa*, typically a mutualistic bacterium but one that can turn into a pathogen and cause disease. Using the referenced CRISPR systems, virulence factors are compromised or excised in a manner that makes such bacterium much safer to employ, and reducing substantially its pathogenic capabilities, such that population of a person's skin with such modified bacteria causes conditions of competitive inhibition of other pathogenic wild type bacteria of the same species. The use of such modified bacteria is therefore useful in preventing wild type strains form gaining entry into the blood system where it is known to cause infections in bone, joint, gastrointestinal, and respiratory systems, as well as dermatitis. Moreover, while virulence factors are excised or reduced by modification, other aspects of the bacteria re maintained, such as its production of antimicrobial substances such as pseudomonic acid, such that infections caused by staphylococcal and streptococcal are reduced, as well as the growth of fungus species such as *Candida krusei, Candida albicans, Torulopsis glabrata, Saccharomyces cerevisiae* and *Aspergillus fumigates*, and importantly, the use of such modified bacteria can inhibit the growth of *Helicobacter pylori*. Other bacteria that may be modified to reduce if not eliminate various compounds from being produced by bacteria that ordinarily are known to generate undesired orders include Propionibacteria, which can turn amino acids into propionic acid, *Staphylococcus epidermidis*, which breaks human sweat into isovaleric acid (3-methyl butanoic acid), and *Bacillus subtilis*, which creates malodorous compounds that lead to foot odor.

In certain embodiments, one aspect of the present invention is directed to the treatment of acne by using probiotic treatments that include effective amounts of *Staphylococcus epidermidis* and/or *Lactobacillus plantarum* to inhibit *P. acnes* growth, which are believed to produce succinic acid, shown to inhibit *P. acnes* growth. CRISPR-Cas and/or Cpf1 systems are used to modify such bacteria in a manner that reduces the occurrence of acne, such as by altering the expression of genes so that the amount of succinic acid on a person's skin is increased.

Still other aspects of certain embodiments are directed to treating individuals with atopic dermatitis, a disease that is associated with low bacterial diversity due to colonization by *S. aureus*, with such treatment including the purposeful application of a formulation that contains effective amounts of *S. epidermidis* to inhibit *S. aureus* growth. Preferably the skin bacteria population should demonstrate high levels of *Bacteroides* and low levels of Firmicutes. Thus, application of probiotics to a person's skin to achieve such a desired ratio of bacterial species is one aspect of various embodiments of the present invention, with preferred embodiments including the use of CRISPR-Cas systems to modify selected bacteria in a manner that enhances their abilities to reside on a person's skin.

Yet another aspect of certain embodiments is directed to addressing the population of Psoriasis *vulgaris* on a person's skin, which is typically found on drier skin sites such as elbows and knees. Dry areas of the skin tend to have high microbial diversity and fewer populations than sebaceous sites. Use of beneficial bacteria, especially those modified via the CRISPR-Cas and Cpf1 systems to enhance certain characteristics of friendly beneficial bacteria, such as the amount of lipids produced, so as to remedy dry skin conditions, is one aspect of the present invention. Thus, in certain embodiments, taking resident species of bacteria from a person's skin in a dry area and modifying such bacteria so as to increase the amount of lipids produced by such bacteria, and preferably enhancing particular other characteristics of such bacteria so as to competitively inhibit other undesired bacteria from occupying those skin areas, is one method for enhancing the health of the person's dry skin areas.

In the context of various embodiments, the use of antibiotic soaps should be avoided so as to permit the beneficial bacteria as described herein to generate positive conditions for beneficial bacteria growth and maintenance. Thus, to reduce the opportunity for more organisms to develop a resistance to some of the substances, such as Triclosan, and the removal of skin lipids alcohols and detergents by detergents and soaps, such substances should be avoided when employing the beneficial bacteria formulations described herein, unless such use is performed prior to application thereof in a manner to reduce the number of undesired bacteria first, followed preferably by a removal of such antibacterial substances so that the desired bacteria can be administered in a fashion that they prosper on the skin.

Damaged skin has also been found to be more frequently colonized by *Staphylococcus hominis, Staphylococcus aureus*, Enterococci and *Candida*. Thus, by topical application of effective amounts of the beneficial bacteria as described herein, especially those modified via the CRISPR systems, it is possible to combat these undesired bacteria and promote the health of an individual's skin microbiome.

Yet other aspects of the present invention relate to the skin on a person's head, and in particular, relates to the maintenance of hair growth on the human scalp. Sulfation of minoxidil to generate minoxidil sulfate is required to achieve the hair growth effect but minoxidil sulfate is unstable, and thus cannot be administered as is. Sulfotransferase enzyme can be used to sulfonate minoxidil to its therapeutic form. In one embodiment of the invention, sulfotransferase enzyme genes are provided via a CRISPR-Cas system such that modified bacteria are able to produce such enzyme in a manner that converts minoxidil to its therapeutic form.

Psoriasis is a chronic, genetically based, immune-mediated inflammatory disorder of the skin, present in about 2% of the world's population. The causes of psoriasis are poorly understood. The disease appears to result from a combination of genetic and environmental factors. Certain skin bacteria, namely *Staphylococcus aureus* and *Streptococcus pyogenes*, play a role in the induction and maintenance of psoriasis. Modification of the microbiome of an individual, including not only the gut, but the skin microbiome, and especially employing a lotion that includes a probiotic modified (via CRISPR-Cas systems) bacteria, as described herein, is one effective way in which to treat Psoriasis and reduce its negative effects.

One objective of the present invention is to provide a method and system to achieve a balanced microbial community in order to reduce or alleviate certain disorders. Personal care products related to microbial communities on the skin is one focus of various embodiments. Such products include, in various embodiments, particular microorganisms that colonize the skin that include *Staphylococcus epidermidis* and other coagulase negative staphylococci, as well as species of *Corynebacterium* and *Propionibacterium*, all of which are preferably modified using the CRISPR-Cas or Cpf1 systems to delete certain virulence factors and to include beneficial traits, such as lipid production to facilitate moisturizing characteristics of particular formulations.

Sebaceous sites, such as the forehead, have the lowest diversity, and *Propionibacterium* species are the most dominant organisms at such sites. On the other hand, moist areas (e.g., armpits, navel, groin) constitute higher diversity of microbiota, with *Staphylococcus* and *Corynebacterium* species as the predominant members. Moreover, skin sites with greater bacterial diversity (e.g., forearm, hand, buttock) can harbor diversity as high as or higher than that of the gut microbiome. Acidic conditions resulting from sebum degradation discourages pathogens from invading and establishing in the skin. Personal hygiene is another environmental factor that has a direct effect on the skin's microbial flora.

Soaps, makeup, and skincare products (e.g., moisturizers) alter skin conditions that in turn may influence the types of microbes residing on the skin. Among the host factors are age, sex, and anatomic sites. Skin microbiota differ among various age groups, with significantly different bacterial communities between the youngest and the oldest groups. A newborn acquires resident bacteria on the skin soon after birth, and their composition is affected by birth delivery methods. Hormonal changes during puberty stimulate the growth of lipophilic (or lipid-loving) bacteria due to sebum production. Physiological changes and anatomic differences also contribute to microbial community variance between genders.

Certain skin diseases develop when altered lipid composition and organization occurs. An example is acne, an inflammatory malady that affects 80% of adolescents in the U.S. The change of lipid composition during puberty encourages lipophilic organisms, such as *Propionibacterium acnes*, to proliferate. As these bacteria derive energy from metabolizing fatty acids in the sebum, a variety of enzymes are secreted that injure the tissue lining of sebaceous glands.

*S. aureus* is one of the most commonly cited skin pathogens, and it is responsible for several cutaneous infections such as impetigo, furuncles, subcutaneous abscesses, ulcers, and other more serious systemic infections when penetrating into the blood stream (e.g., toxic shock syndrome). Various embodiments of the present invention involve the modification of *S. aureus* to reduce its virulence factors and to otherwise enhance its beneficial characteristics, especially in terms of the amount of moisturizing compounds produced by such bacteria after being modified via a CRISPR-Cas system to include genes for desired emollients, such as lipids.

Atopic dermatitis is a chronic and intensely inflammatory skin disorder that has more than doubled in industrialized countries in the past three decades without a clear cause. Atopic dermatitis patients frequently acquire cutaneous infections with *S. aureus* as the main colonizing organism. Disease severity and bacterial diversity are related, with atopic dermatitis being most severe when community diversity is low, and as the modified microbiota as described herein increase in number, a level of diversity similar to those of healthy skin may be attained.

*Staphylococcus* species have been implicated in both impaired wound healing and leg ulcers. Thus, in certain other embodiments, modification of such bacteria via CRISPR-Cas systems to reduce its virulence factors, and the subsequent use of competitive inhibition to reduce the population of non-modified bacteria of the same species, provides a way to address the issues long experienced by such bacteria impairing wound healing and causing leg ulcers.

Neonatal skin reveals an abrupt wave of highly activated Treg cells accumulating in the tissue during the first weeks of life. Selective inhibition of Treg cell migration into skin, and during this period completely abrogates commensal-specific tolerance. One aspect of the present invention is directed to appreciating that there is a specific window of time that is required for establishing a healthy host-commensal relationship on the skin. Certain embodiments of the present invention are directed to providing beneficial bacteria, namely particular bacteria modified via CRISPR-Cas systems so as to generate desirable immune functionality of a newborn by exposing such newborn to particular species of bacteria and other microbes that trigger normal development of the newborn's immune system.

*S. epidermidis* is a prevalent commensal bacterial species on human skin. Skin bacterial antigens are recognized by the adaptive immune system across an intact skin barrier. Skin commensal bacteria influence cutaneous immunity without causing tissue inflammation. Because a host-commensal relationship is formed immediately after birth, one aspect of the present invention relates to the appreciation that the mechanisms required for establishing tolerance are preferentially active during this period of time, such that administration of the various different and beneficial microbes to an infant's skin in the first 24 hours of life may be critical in the infant from developing an entire host of immune related diseases in later life.

Treg cells generated in neonatal life have the potential to promote self-tolerance and tolerance to commensal antigens. The phenomenon of a wave of Treg cells into neonatal tissue is unique to skin. Skin-barrier function influences more than local immunity and skin colonization results in commensal-specific T cells that are found both locally and systemically, and thus, maintaining a healthy microbe-host immune dialog in skin is important for both systemic and tissue-specific immune homeostasis. Altering the composition of skin commensal microbiota in the neonatal period can limit the opportunity to establish tolerance to a wide array of microbial antigens, resulting in chronic tissue inflammation. There are a variety of chronic inflammatory diseases of the skin that form abnormal anticommensal immune responses. The composition of the cutaneous microbiome in neonatal life has formative effects on the adaptive immune response to commensals, and understanding and manipulating the microbe is one aspect of the present invention with the objective being to establish modifications to an individual's skin microbiome to achieve enduring health implications.

The skin microbiota is dependent on the body site and the colonization of bacteria is dependent on the physiology of the skin site. Specific bacteria are associated with moist, dry and sebaceous microenvironments, with bacterial diversity lowest in such sebaceous sites. *Propionibacterium* spp. a lipophilic bacteria, is the dominant organisms in such sebaceous areas.

Certain bacteriophages are suitable for incorporating into certain antiperspirant and deodorant compositions, and are effective and specific in fighting against bacteria causing odor without irritating the skin or damaging the germs in the flora of the skin which have a positive effect. According to the invention, cosmetic and/or pharmaceutical compositions suitable to deodorizing the body contain, in a cosmetic or dermatologically acceptable carrier, at least one deodorant or antiperspirant active substance and at least one representative from the group of bacteriophages which are effective against at least one of the following: *Staphylococcus aureus* and/or *Staphylococcus hominis* and/or *Corynebacterium tuberculostearicum* and/or *Anaerococcus octavius* and/or *Staphylococcus lugdunensis* and/or *Finegoldia magna* and/or *Corynebacterium amycolatum* and/or *Corynebacterium afermentans* and/or *Staphylococcus epidermidis* and/or *Staphylococcus capitis* and/or *Staphylococcus haemolyticus* and/or *Propionibacterium avidum* and/or *Corynebacterium kroppenstedtii* and/or *Peptoniphilus* spec. Each of such bacteria can be modified using CRISPR-Cas systems to reduce the production of malodorous components and to provide microbes that out compete wild type bacteria of the same species.

One particular aspect of the present invention is directed to decreasing body odor by inhibiting *Staphylococcus hominis* that is involved in body odor formation. Thus, certain embodiments are directed to a deodorant composition or antiperspirant composition for the reduction of the body odor, involving applying to a person's skin a bacterial formulation that includes bacteria that generate lactic acid in combination with physiologically acceptable salts, with sodium salt most preferred. Even more preferred embodiments involve the modification of *Staphylococcus hominis* to reduce if not eliminate virulence factors of the species, and employing such modified bacteria to competitively inhibit non-modified strains, thus providing a way for an individual to reduce body odor (e.g. by at least 20%, more preferably at least about 50% and most preferably 80%) by inoculation of certain portions of their body, namely their armpits, with the modified bacteria. The sweaty odor of humans is comprised of acids, thiols and steroids. Sulfur compounds in a person's mouth are similar to the thiols present in armpit malodors. Thus, reducing the expression of thiols in particular bacteria by CRIPSR-Cas and/or Cpf1 systems is implicated in various embodiments of the present invention.

*Propionibacterium*, and *P. acnes* in particular, are dominant organisms in normal skin. One aspect of the present invention is directed to the perhaps the anti-intuitive fact that maintenance of a robust population and colony of such bacteria on an individual's skin plays a protective role that preserves and maintains normal skin health. Various illness of individuals occurs when *P. acnes* is displaced by more aggressive organisms. Thus, one aspect of the present invention is directed to CRISPR-Cas modified bacteria that have particular advantages in competitive competition with wild type strains, such as being provided with certain genes that render their colonization of the skin slightly more preferred than wild type strains.

In some embodiments, genetic modifications are made in a *Cutibacterium acnes* porphyrins gene, a CAMP-factor (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-β-N-acetylglucosaminidase, Dermatan sulphate adhesin (DsA1, DsA2), Proline-Threonine Repeats (PTRs) or in any virulence factors included on the acne associated genomic loci 1, 2, 3 (plasmid), 4 such as a tight adhesion locus (tad), Streptolysin S-associated genes (sag), nonribosomal peptide synthetases (NRPS) as described in Tomida et al., which is hereby incorporated by reference.

In one embodiment, the bacterial origin of replication is functional in *Propionibacterium* and *Cutibacterium* more specifically in *Propionibacterium freudenreichii* and *Cutibacterium acnes* and is selected from the group consisting of pLME108, pLME106, p545, pRG01, pZGX01, pPG01, pYS1, FRJS12-3, FRJS25-1, pIMPLE-HL096PA1, A_15_1_R1.

In a particular embodiment, the phage origin of replication is from *Propionibacterium* phages: BW-like phages such as Doucette, B22, E6, G4, BV-like phages such as Anatole, E1, B3, BX-like phages such as PFR1 and PFR2, filamentous B5 phage, BU-like phages (*Cutibacterium acnes* phages).

In one embodiment, the targeted bacteria are *Cutibacterium acnes* more specifically the acne related *Cutibacterium acnes* from the phylogroup IA1 or RT4, RT5, RT8, RT9, RT10 or Clonal Complex (CC) CC1, CC3, CC4, more specifically the ST1, ST3, ST4.

Certain embodiments of the present invention encompass the treatment of diseases and metabolic disorders caused by bacteria. The diseases or disorders caused by bacteria may be selected from the group consisting of skin chronic inflammation such as acne (acne *vulgaris*), progressive macular hypomelanosis, abdominal cramps, acute epiglottitis, arthritis, bacteraemia, bloody diarrhea, botulism, Brucellosis, brain abscess, cardiomyopathy, chancroid venereal disease, Chlamydia, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myocarditis, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough, Nonalcoholic Fatty Liver Disease (NAFLD), Nonalcoholic steatohepatitis (NASH).

*Staphylococcus epidermidis* is with *Cutibacterium acnes* one of the two most prevalent and abundant commensal bacteria on the human skin. As such it has been shown to prevent colonization by pathogenic bacteria like its close relative *Staphylococcus aureus*, prevent skin cancer or also modulate the human immune system. However, it is also a growing concern due to its opportunistic pathogenic characteristic and its growing resistance to antibiotics. These pathogenic traits of *S. epidermis* might be encoded on specific virulence genes or cluster and some of these might spread across strains by horizontal gene transfer.

The loss of *Propionibacterium* presence on a person's skin is indicative of psoriatic disease and thus, one objective in various embodiments is to limit or reduce numbers of over-represented organisms typically found in disease states on the skin and to increase populations of commonly occurring resident microbes that are diminished in disease. Such a probiotic approach is effective in addressing long unsolved skin conditions.

Commensal microorganisms that comprise the human microbiota are not simply passengers in the host, but actually drive certain host functions. One aspect of the present invention is to introduce beneficial bacteria to the skin, where such bacteria may not typically have a real opportunity to survive and prosper. Thus, in several embodiments, two or more bacteria are employed with each providing aspects of an environment such that another bacteria can survive. For example, one bacteria may provide an acid producing ability that another bacteria needs to prosper. Both bacteria can then depend on each other for survival—and if either is absent, then the other is eliminated. So, for example, in certain embodiments, formulations and methods of administration of skin microbes are designed to that certain bacteria possess an antibiotic sensitivity that is only not expressed when the another bacteria is present—such that if both are not there, then they each will die. This type of synergism is preplanned and calculated to provide at least two different types of bacteria, in some embodiments at least three types of bacteria, and in other embodiments at least four bacteria species modified so that they are co-dependent upon each other for a critical factor in each other's survival, such that they all need to be present on the skin at the same time to co-survive. In such a manner, coordination of selection of bacterial species can be used to foster the desired diversity of bacteria that has been appreciated as being beneficial to the overall health of a skin microbiome.

In certain embodiments, CRISPR-Cas systems are employed to modify the adhesion characteristics of particular bacteria, namely adhesions, which are molecular parts of their capsules, fimbriae, and cell walls that attach to a host surface. In certain embodiments, modifications may be made to enhance the adherence of certain desired bacteria to particular tissues so as to competitively inhibit the attachment of other undesired bacteria to such tissues.

Pathogenic bacteria display various levels of host specificity or tropism. While many bacteria can infect a wide range of hosts, certain bacteria have strict host selectivity for humans as obligate human pathogens. Various aspects of the present invention are directed to the employment of host specific bacteria that are modified via the CRISPR-Cas and/or Cpf1 systems in a manner that does not pose a threat to various other species, thus reducing the threats that might otherwise be presented if large-scale modifications of bacteria are modified by CRISPR systems.

Certain bacteria are highly adapted to the human environment and display strict host selectivity for humans, including *Haemophilus influenzae, Helicobacter pylori, Neisseria gonorrhoeae, Neisseria meningitidis, Mycobacterium leprae, Salmonella Typhi, Streptococcus pneumoniae, Streptococcus pyogenes, Vibrio cholerae* and *Treponema pallidum*. One aspect of the present invention relates to the modification of human-specific pathogens to reduce virulence factors of such bacteria using one of a CRISPR-Cas or Cpf1 system. Other embodiments include the enhancement of selective bacteria with respect to their ability to grow and colonize the human skin by competitively inhibit other undesired species. By rendering such human-specific bacteria, many considered to be pathogenic, less harmful to humans, one aspect is directed to employing such modified bacteria to outcompete and thus competitively inhibit the colonization of non-modified bacteria on a person's skin.

*N. gonorrhoeae* and *N. meningitidis* are two human pathogens within the genus *Neisseria. N. gonorrhoeae* is the causative agent of gonorrhea (pelvic inflammation), a sexually transmitted disease. *N. meningitidis* causes invasive infections, such as septicemia and meningitis. Both pathogens have strict host tropism for humans. Like many other human-specific pathogens, the narrow host specificity of these pathogenic bacteria renders them suitable for modification to make them less pathogenic, and at least to reduce the population of wild type more virulent strains. In one embodiment, CRISPR-Cas systems are used to excise particular virulence factors of particular bacteria, such as *Neisseria*, preferably affecting one or more surface-exposed proteins associated with the human specificity of pathogenic *Neisseria*.

The present inventor contends that *S. aureus* colonization is a cause of various diseases, and thus its reduction or near elimination results in an amelioration of the clinical symptoms. *Staphylococcus aureus* is responsible for a variety of diseases ranging from minor skin infections to life-threatening systemic infections, including endocarditis and sepsis, and is a major cause of community- and hospital-acquired septicemia. Atopic dermatitis (AD) is a disease of skin microbiota dysbiosis with *S. aureus*, interventions that reduce *S. aureus* colonization on the skin of AD patients is one objective of the present invention. There is an existing problem with respect to antibiotic resistance of *S. aureus*. Microbiologists are now facing a challenge to design strategies decreasing *S. aureus* skin load. *S. aureus* causes the majority of bacterial skin infections, including some historically caused by streptococcal species. Bacterial skin infections can be classified as primary or secondary and as an initial episode or a recurrence. Primary infections manifest in normal, intact skin. Examples include impetigo, cellulitis, folliculitis, or furunculosis. Secondary infections manifest in conditions with an impaired skin barrier. Common examples include atopic dermatitis, bites, burns, and wounds. In atopic dermatitis, S. aureus colonization is common and secondary S. aureus infections are a major concern. Patients with atopic dermatitis are at risk for secondary infections due to impaired physical barrier function, colonization with pathogenic bacteria, and alterations to the skin microbiome. An additional risk for infection relates to deficiencies in the antimicrobial defenses of the skin.

In one embodiment, S. aureus is modified via CRISPR systems to render such bacteria antibiotic sensitivity and such sensitive culture is then purposefully employed to populate the skin of an individual, thus competitively inhibiting the residence of other S. aureus on the person's skin. Removal of bacteria, including S. aureus, prior to such re-population step is preferably employed so as to facilitate the re-establishment of the modified S. aureus as a bacterial species, despite the appreciation that such species is not a typically desired bacteria on a person's skin.

Worsening atopic dermatitis and smaller bacterial diversity are strongly associated. Thus, one aspect of certain embodiments relates to increasing the diversity of bacteria on a person's skin via the application of formulations that include beneficial bacteria in amounts and with particular diversity of species so as to promote the health of a person's skin in a manner to reduce the likelihood of atopic dermatitis. The application of such formulations is preferably conducted without the use of emollients containing antioxidant and antibacterial components that may reduce microbiome diversity in atopic skin. As about one third of deaths in adults in the elderly are due to infectious disease, it is believed that the present invention provides an avenue to reduce the number of such deaths and to otherwise address the significant health issues related to skin ailments, including but not limited to atopic dermatitis. One theory is that as a person ages, their immune system changes and is less robust in addressing bacterial infections. By enhancing the microbiome of a person's skin as they age, it is believed that infections that would otherwise be encountered will be avoided, or at least the frequency and severity of the same will be decreased.

Staphylococcus aureus is a Gram-positive, commensal bacterium known to asymptomatically colonize the human skin, nares, and gastrointestinal tract. Colonized individuals are at increased risk for developing S. aureus infections, which range from mild skin and soft tissue infections to more severe diseases, such as endocarditis, bacteremia, sepsis, bacteremia, pneumonia and osteomyelitis. Staphylococcus aureus is one of the most important bacterial pathogens in hospital- and community-acquired infections. Different virulence factors are required for S. aureus to infect different body sites. Various aspects of the present invention are directed to modifying bacteria using the CRISPR-Cas and Cpf1 systems to reduce various virulence factors, including those involved in S. aureus infections, and by doing so, protecting individuals from one or more of the diseases related to such bacterium.

Probiotics are believed to play a part in protecting skin against photoaging. Supplementation of a person's skin with particular bacteria, and preferably a diverse set of bacteria, even more preferably bacteria that have been modified by using a CRISPR-Cas or Cpf1 system to reduce various virulence factors of such bacteria, and/or to incorporate UV protectant chemicals and proteins generated by the modified bacteria, is employed to significantly enhance skin hydration, reduce epidermal thickening and transepidermal water loss, and to further protect the skin form harmful UV radiation. Supplementation of a person's skin with an effective amount of a Bifidobacterium strain, preferably modified via CRISPR-Cas system to enhance UV protection, is one aspect of various embodiments.

Yet another aspect of the invention is directed to a method via which a bacterial containing lotion, gel or cream is administered topically to provide a person with a diverse number and type of bacteria, especially those modified via CRISPR systems as described herein, and in such a manner, reduce the likelihood of skin infections.

Certain aspects of the present invention relate to a composition including ammonia oxidizing bacteria to increase production of nitric oxide and/or nitric oxide precursors in close proximity to a person's skin. More specifically, applying a composition of an ammonia oxidizing bacteria to skin during or after bathing to metabolize urea and other components of perspiration into nitrite and ultimately into Nitric Oxide (NO) results in a natural source of NO. One aspect of the present invention causes topical nitric oxide release at or near the surface of the skin where it can diffuse into the skin and have local as well as systemic effects. This naturally produced nitric oxide can then participate in the normal metabolic pathways by which nitric oxide is utilized by the body. Adding urea or ammonium salts to the skin provides additional substrates that these bacteria utilize to form nitrite. As used herein, the phrase near the surface is defined as adjacent to or in close proximity to, but need not be in contact with the surface.

Prior to the advent of frequent bathing in hot water and soap substances, the skin on a human would develop a natural community of microorganisms adapted to the skin environment. An abundant component of human perspiration is urea. In soil, natural bacteria act upon urea and hydrolyze it to ammonia, which is then oxidized to nitrite, followed by rapid oxidation, by still other bacteria, to nitrate. In soil, all nitrogen containing compounds are ultimately degraded to nitrate. It is nitrate that most plants absorb as their nitrogen source. Under conditions of infrequent bathing, skin bacteria that can metabolize urea into nitrite—thrive and proliferate. The resulting nitrite on the skin when dampened by additional perspiration at the normal sweat pH of 4.5 would release Nitric Oxide (NO). Nitric Oxide is a small molecule that diffuses rapidly through the skin into the capillaries of the skin. Vasodilatation of these capillaries occur, as well as diffusion of NO into the blood where it can be transported to other regions of the body. Dilatation of the capillaries at the skin surface enhances blood flow to, and hence heat loss from the skin during periods of exercise.

In certain embodiments, an ammonia oxidizing bacteria may be used and preferably may have the following characteristics: ability to rapidly metabolize ammonia and urea to nitrite and other NO precursors; non pathogenic; non allergenic; non-producer of odoriferous compounds; non-producer of malodorous compounds; ability to survive and grow in human sweat; ability to survive and grow under conditions of high salt concentration; and ability to survive and grow under conditions of low water activity. Natural bacteria can be used as well as bacteria whose characteristics have been altered through genetic engineering techniques, preferably via CRISPR systems as set forth herein. While some skin bacteria species double every 20 minutes, ammonia-oxidizing bacteria, preferred in various embodiments of the present invention, are much slower growing, doubling only every 10 hours. *Nitrosomonas eutropha*, an ammonia-oxidizing bacteria is one preferred species to employ on a person's skin to enhance the health of the skin and to avoid chemical use typically deemed required to thwart body odor.

Compositions of the present invention may take the form of a gel, a cream, a lotion, an ointment, a solution, a solid "stick," etc., that can be rubbed or sprayed onto the skin. Certain embodiments include water, live cultured ammonia-oxidizing bacteria, disodium phosphate, and magnesium chloride. Preferably, such compositions include selected bacteria that have been modified via CRISPR-Cas or Cpf1 systems to specifically target disease states and are used to reduce the effects thereof. For example, particular compositions include live *Lactobacillus*, employing various strains that can also be found in edible compositions, such as probiotic yogurts and nutritional supplements. In preferred embodiments, there is an absence of sodium lauryl sulfate, a potent detergent, which is preferably avoided as it can remove your healthy bacteria. Other embodiments employ *Bifidobacterium longum* and *Lactobacillus plantarum*, both of which are modified via the CRISPR systems as described herein. It is believed that such *Lactobacillus* species reduce symptoms of eczema, especially when modified to encourage its growth and maintenance on the skin, where normally it is not found in abundance.

In still other embodiments, CRISPR systems are used to modify the genera *Propionibacterium, Corynebacterium* and *Staphylococcus*, and in particular *S. epidermidis*, which are among the most common groups on a person's skin, with such modifications making such species more amenable to growth on the skin, thus providing for competitive inhibition of non-modified bacteria on the skin. As one of skill in the art will appreciate, a suitable topical composition comprising a population of the above bacteria can be, in various embodiments, a cream, lotion, emulsion, gel, ointment, liquid or spray. In one embodiment, the topical composition is formulated to provide at least about 10.sup.2 bacteria per cm.sup.2. In another aspect, a method of treatment is provided, wherein a composition as described herein is topically applied to the skin and in certain embodiments, topically applying includes topically applying to a mucosal surface (nasal, vaginal, rectal, oral surfaces) of a person. A suitable lotion may also include amounts of sugars that the various *Lactobacillus* microorganisms may assimilate to survive and thrive. These sugars and life bacteria-supporting compounds are known to those in the art and as otherwise referenced in various incorporated writings. In still other embodiments, pulverized compositions of helminth collections and bacteria preferably obtained from Amish-soils, may be employed in various administrative modes, including but not limited to lotions, creams, and other topical applications.

With respect to the employment of extracts of helminths (intestinal worms), which have been almost completely eliminated in Western countries over the last 50 years, and while cognizant that some helminths previously caused a significant burden of disease, there are many helminths that are benign. The loss of all helminths, both pathogenic and benign, from the ecosystem of the human body profoundly increases the propensity for chronic inflammation-associated disease. The present inventors contend that exposure to helminths may be critical for the elimination of allergic disease, and for the prevention of autoimmune diseases and some neuropsychiatric disorders. Helminth derived products, such as extracts, rather than use of the helminths themselves, is therefore an aspect of certain embodiments of the present invention as individuals can achieve the benefits of helminthic therapy without the detriments of live helminths, especially when employing the surface or excretory/secretory products of helminths to address inflammatory conditions and diseases.

Under the FD&C Act, a product's category is based primarily on intended use. For example, the term "cosmetics" is defined in section 201(i) of the FD&C Act in part as "articles intended to be rubbed, poured, sprinkled, or sprayed on, introduced into, or otherwise applied to the human body or any part thereof for cleansing, beautifying, promoting attractiveness or altering appearance". Thus, various embodiments of the present invention are directed to cosmetic compositions that include microorganisms or fractions thereof that enhance the health of a person's skin. Still other embodiments are directed to a shampoo and a conditioner having a sufficient amount of bacteria therein to beneficially affect the scalp of the user. Yet other embodiments are directed towards personal care products, including those that may help to prevent disorders or restore health of the skin, such as, but not limited to, particular cuticle formulations that are beneficial to the health of a person's nail beds on their hands and feet.

One aspect of the present invention is to determine a person's particular microbiome composition, compare it generally to the characteristics of the general population in the general area where such individual resides, and then address any differences in such microbe populations differences on the particular person by providing particular microbe components, whether that be actual microbes themselves or the provision of nutrients for particular microbes to out-compete other microbes, such that a population of microbes more like those of the general population is achieved.

One basis from which several embodiments of the present invention relate include an appreciation that the general population of microbes in a human population in a particular area, for example in a city, will have certain general characteristics. Individuals that possess microbe populations on their skin that vary significantly from such general population of microbes are often suffering from maladies that are directly related to the imbalance of microbe populations on their skin. As such, one aspect of the present invention is to address such imbalance by providing methods and compositions that bring the particular microbe population of a particular individual back into the relative balance of microbe population as exists in the particular city within which such individual lives.

There are noted differences of microbe populations on an individual's skin dependent on race, gender, age and living environment, particularly the location of the person, e.g. whether they are in the tropics, northern climes, etc. These factors are taken into account when addressing the alteration of a particular person's microbiome so that modifications made to the individual's microbiome are adjusted to achieve roughly the same microbe population as would be predicted from more general criteria of a hypothetical person having similar race, gender and age characteristics in a particular locale. In a way, such conformance with respect to the microbiome in a community is a beneficial trait for such community, as well as for the individuals residing therein. There has not been, prior to the present invention, a method or system that addresses the imbalances that exist periodically in a community's overall microbiome so that issues arising from individuals who present personal microbiomes that present significantly different microbe populations on their skin can be addressed by, for example, reducing the type and number of bacteria on such person's skin, followed by purposeful exposure of such person's skin to a predetermined population of bacteria as described herein. By such exposing of such person to microbes and microbe enhanced compositions, one is able to achieve a more uniform overall microbiome of an entire community and enjoy the health benefits derived therefrom.

Various factors affect the microbial flora of the skin and they can be generally categorized into host and environmental factors. Sebaceous sites such as the forehead have the lowest diversity, and *Propionibacterium* species are the dominant organisms. On the other hand, moist areas (e.g., armpits, navel, groin) constitute higher diversity of microbiota, with *Staphylococcus* and *Corynebacterium* species as the predominant members. Skin sites with greater bacterial diversity (e.g., forearm, hand, buttock) can harbor diversity as high as or higher than that of the gut microbiome. The acidic condition resulting from sebum degradation discourages pathogens from invading and establishing in the skin. Personal hygiene is another environmental factor that has a direct effect on the skin's microbial flora. Soaps, makeup, and skincare products (e.g., moisturizers) alter skin conditions that in turn may influence the types of microbes residing on the skin. Host factors, such as age, sex, and anatomic sites demonstrate that skin microbiota differ among various age groups. For example, acne, an inflammatory malady that affects 80% of adolescents, relates to a change of lipid composition during puberty that encourages the proliferation of lipophilic organisms, such as *Propionibacterium acnes*. As these bacteria derive energy from metabolizing fatty acids in the sebum, a variety of enzymes are secreted that injure the tissue lining of sebaceous glands. In conjunction with activated immune responses, this results in a skin condition termed acne *vulgaris*. In contrast, younger children have a higher abundance of *Staphylococcus (S.) aureus*, which are later replaced by lipophilic and other bacteria. Conversely, certain skin disorders, such as atopic dermatitis (or eczema), are more prevalent among children but often resolve by adolescence and adulthood. *S. aureus* is one of many skin pathogens responsible for several cutaneous infections such as impetigo, furuncles, subcutaneous abscesses, ulcers, and toxic shock syndrome. Burn victims whose epidermis have been destroyed are exposed to various assaults, with Gram positive bacteria (e.g., *S. aureus*) being main colonizers after a burn. A shift then occurs and Gram negative opportunistic organisms predominate, some with virulent properties that can cause life threatening infections. Thus, in certain embodiments of the present invention, a particular formulation is provided that includes a diverse range of bacteria that have been preferably modified via the CRISPR systems as described herein so as to establish a particular population of diverse bacteria that enhance the healing environment of a burn victim's skin.

The many layers and structures of the skin serve as elaborate hosts to microbes, including a diversity of commensal and pathogenic bacteria that contribute to both human health and disease. In several embodiments, a formulation includes a diverse population of bacterial species based on a collection of various racial skin types and for particular ethnic populations, such as an enhanced proportion of *Enhydrobacter* for Chinese ancestry. Other formulations include bacterial formulations with Actinobacteria, Proteobacteria, Firmicutes, Bacteroidetes, in 40/30/20/10 ratios. Firmicutes (mainly *Streptococcus* and *Staphylococcus*), *Enhydrobacter, Gordonia*, and Actinobacteria (mainly *Corynebacterium* and *Propionibacterium*) are preferably employed, again modified via CRISPR-Cas and Cpf1 systems to reduce the virulence factors normally encountered in such bacteria. In various embodiments, CRISPR-Cas systems are employed to modify the following species belonging to the genera *Corynebacterium, Staphylococcus, Streptococcus*, and *Anaerococcus*.

During the birthing process and subsequent exposure to the post-natal environment, the skin is colonized by a wide array of microbes. Knowledge of the skin microbiota has historically been limited to culture-dependent assays, although it is estimated that less than 1% of bacterial species can be cultivated. Recent findings reveal a low level of interpersonal consensus and an extremely dynamic microbiota that fluctuates greatly in a short span of time. So changing a person's bacterial skin composition is not something that should be viewed as somehow detrimentally affecting their health as such populations are seen to vary greatly in any event under natural conditions. Thus, one aspect of the present invention relates to the modification of a person's microbiota on their skin in a manner believed to enhance the overall health of the skin, thus preventing diseases that may otherwise infect such person's skin. The diversity of the skin formulations as set forth herein include compositions that include at least the following (and particularly such species modified via CRISPR systems to reduce their respective virulence factors and to enhance their abilities to out compete other bacteria on a person's skin): Proteobacteria, of the *Janthinobacterium, Serratia, Halomonas, Stenotrophomonas, Delftia*, and *Comamonas* genera; Actinobacteria, including species of the genera *Corynebacterium, Kocuria, Propionibacterium, Microbacterium*, and *Micrococcus*; Firmicutes, such as *Staphylococcus* or *Clostridium* species; and Bacteroidetes, including Sphingobacterium or *Chryseobacterium* species. In other embodiments, a common core skin microbiome is derived from healthy human subjects, and then such bacteria are enhanced via CRISPR-Cas systems to remove virulence factors, prior to administering the modified bacteria to a person's skin for the purpose of improving the skin microbiome thereof.

The general *Pseudomonas* and *Janthinobacterium* (both pseudomonads; gram-negative bacilli, aerobic, non-spore forming, motile by means of one or more flagella) are not typically thought of as skin microbes based on culture assays. Pseudomonads (and other Gram-negative bacilli) have historically been labeled as secondary invaders of wounds, most commonly referring to the colonization of burns by *Pseudomonas aeruginosa*. Pseudomonads are found in soil, water, and decomposing organic materials where there is a moist environment. Modification of such bacteria so that it is less virulent and more readily reduced in number due to CRISPR-Cas enhanced antibiotic sensitivities, forms one embodiment of the present invention, and one that can be employed to treat wound infections to competitively inhibit non-modified strains from infecting a wound.

Because skin cells turn over every 4 weeks, differentiating from stem cells deep within the epidermis and hair follicles, they eventually slough off from the upper layer as cornified (enucleated, dead) cells. The skin microbiome is vastly different from the gut microbiome, which consists primarily of members of Firmicutes and Bacteroidetes divisions. The skin is also different from the gut in that there is a low level of interpersonal variation of skin microbiomes, which is not the case in gut studies. Regardless, there is a low level of deep evolutionary lineage diversity, with only six of the more than 70 described bacterial divisions associated with the skin, and approximately the same number for the gut, which compares to a vast array of bacteria in soil.

Many physiological functions are performed by skin microbiota. Proteobacteria, which dominates the skin microbiota, may be modified via CRISPR-Cas and Cpf1 to achieve desired populations that lack virulence characteristics of wild type strains.

Still other embodiments relate to the adjustment of the microbiome via air conditioning units, HVAC, etc units that propagate beneficial populations into a living environment of individuals. Certain figures from the parent specification provide details as to how such microbes can be disseminated into a living space for humans, which affects both respiratory and skin microbiomes of individuals so exposed.

FDA acceptable limits for total (not pathogenic) microorganisms in cosmetics are very low and are anticipated to be revised to permit the employment of various embodiments of the present invention after a recognition that such products are safe and beneficial and address various disease states. In preferred embodiments, bacteria that produce various products are preferred, such as lactic acid, which serves as a moisturizing factor, hyaluronic acid which improves skin hydration and elasticity, and sphingomyelinase which generates ceramide for skin barrier function. Whether such products are considered a drug or a cosmetic under the FD&C Act, is something the present inventors believe is besides the point: the skin microbiome health is dependent upon the administration of one or more of the compositions as set forth herein and these will increase the benefits sought by numerous individuals.

Yet other embodiments include a topical lotion that comprises a mixture of *Lactobacillus johnsonii*, and *Bifidobacterium longum* bacteria. Such use of probiotic bacteriotherapy is employed in treating skin diseases including eczema, atopic dermatitis, acne, and allergic inflammation or in skin hypersensitivity, UV-induced skin damage, wound protection, and as a cosmetic product. A topically applied composition that comprises a population of pre-selected bacteria comprising various non-pathogenic bacteria and CRISPR-Cas modified pathogenic bacteria is employed to establish a resident population on a person's skin in order to enhance the overall health of the person's skin.

In one such embodiment, a formulation comprises a mixture of various amounts of the following: *Bifidobacterium longum, B. infantis* BCRC 14602; *Prevotella; Ruminococcus, Bifidobacterium infantis, Lactobacillus acidophilus, Bacteroides fragilis, B. longum* bv *Infantis* isolate UCD272; *B. infantis* BCRC; *B. longum* bv *Infantis*, AY151398; and *Lactobacillus ruminus*. Other embodiments include compositions directed to the treatment of sensitive skin, using, as active agent, a combination of a *Lactobacillus paracasei* or *casei* microorganism and a *Bifidobacterium longum* or *Bifidobacterium lactis* microorganism.

Certain microorganisms are known to have a beneficial action on the skin membrane by maintaining a slightly acidic environment. Thus, in certain embodiments, such an acidic environment is first established on the skin and then one maintains beneficial endogenous flora on the skin such that the microflora participates in maintaining a desired physiochemical balance of the skin while not favoring the development of pathogenic microorganisms on the skin surface. The benefits of the skin condition are selected from the group consisting of improving skin appearance, improving skin feel, increasing the thickness of one or more layers of the skin, increasing the elasticity of the skin, increasing the resiliency of the skin, increasing the firmness of the skin, reducing an oily appearance of the skin, reducing a shiny appearance of the skin, reducing a dull appearance of the skin, increasing a hydration status of the skin, increasing a moisturization status of the skin, reducing an appearance of fine lines, reducing an appearance of wrinkles, improving skin texture, improving skin smoothness, improving skin exfoliation, improving skin desquamation, plumping the skin, improving skin barrier properties, improving skin tone, reducing an appearance of redness, reducing an appearance of skin blotches, improving the brightness of the skin, improving the radiancy of the skin, improving the translucency of the skin.

A subject of the invention is also the topical use of an effective amount of at least one probiotic microorganism according to the invention, especially of the *Lactobacillus* and/or *Bifidobacterium* sp. Genus, and in particular of the *Lactobacillus paracasei* ST11 strain, to reduce the likelihood of seborrhoeic dermatosis associated with oily skin or skin with an oily tendency. Microorganisms suitable for this aspect of the invention include an ascomycetes, such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus*, Oenococcus and *Lactobacillus*, and mixtures thereof.

As ascomycetes is particularly suitable for particular embodiments of the present invention, one may desire the use of *Yarrowia lipolytica* and *Kluyveromyces lactis*, as well as *Saccharomyces cerevisiae, Torulaspora, Schizosaccharomyces pombe, Candida* and *Pichia*, all of the same preferably modified via CRISPR-Cas or Cpf1 systems to reduce virulence factors associated with the same. Specific examples of probiotic microorganisms also suitable for the invention include: *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp *bulgaricus, lactis*), *Lactobacillus fermentum, Lactobacillus helveticus, Lactobacillus gallinarum, Lactobacillus gasseri, Lactobacillus johnsonii* (CNCM I-1225), *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus (faecalis, faecium), Lactococcus lactis* (subsp *lactis* or *cremoris*), *Leuconostoc mesenteroides* subsp *dextranicum, Pediococcus acidilactici, Sporolactobacillus inulinus, Streptococcus salivarius* subsp. *thermophilus, Streptococcus thermophilus, Staphylococccus carnosus, Staphylococcus xylosus, Saccharomyces(cerevisiae* or else *boulardii*, *Bacillus (cereus* var *toyo* or *subtilis), Bacillus coagulans, Bacillus licheniformis, Escherichia coli* strain nissle, *Propionibacterium freudenreichii*, and mixtures thereof. In other embodiments, probiotic microorganisms for use in the invention are derived from the group of lactic acid bacteria, such as, in particular, *Lactobacillus* and/or *Bifidobacterium*. In particular, various embodiments use lactic acid bacteria such as *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium*

*infantis, Bifidobacterium adolescentis, Bifidobacterium pseudocatenulatum*, and mixtures thereof. Most preferably for particular embodiments, CRISPR modified bacteria of the following are employed: *Lactobacillus johnsonii, Lactobacillus paracasei, Bifidobacterium adolescentis* and *Bifidobacterium longum*, respectively deposited according to the Treaty of Budapest with the Institut Pasteur (28 rue du Docteur Roux, F-75024 Paris cedex 15) on 30 Jun. 1992, 12 Jan. 1999, 15 Apr. 1999 and 15 Apr. 1999 under the following designations: CNCM 1-1225, CNCM 1-2116, CNCM 1-2168 and CNCM I-2170, and the *Bifidobacterium lactis* (Bb 12) (ATCC27536) or *Bifidobacterium longum* (BB536) genus. The *Bifidobacterium lactis* (ATCC27536) strain can be obtained from Hansen (Chr. Hansen A/S, 10-12 Boege Alle, P.O. Box 407, DK-2970 Hoersholm, Denmark); *Lactobacillus paracasei* ST11 strain deposited according to the Treaty of Budapest with the Institut Pasteur (28 rue du Docteur Roux, F-75024 Paris cedex 15) on 12 Jan. 1999 under the designation CNCM I-2116, and/or a fraction thereof and/or a metabolite thereof.

According to one variant embodiment, the invention relates to the use, in addition to a first probiotic microorganism, as defined above, especially of the *Lactobacillus* and/or *Bifidobacterium* sp. genus, of at least an effective amount of at least a second microorganism, distinct from said first microorganism. Such a second microorganism may be an ascomycetes, such as *Saccharomyces, Yarrowia, Kluyveromyces, Torulaspora, Schizosaccharomyces pombe, Debaromyces, Candida, Pichia, Aspergillus* and *Penicillium*, bacteria of the *Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus, Lactobacillus* or *Bifidobacterium* genus, and mixtures thereof.

In other embodiments, CRISPR-Cas and or Cpf1 systems are used to modify at least one of *Enterobacter aerogenes, Acinetobacter baumannii*, and *Klebsiella pneumoniae*, which are three gram negative bacteria commonly found on the skin, and which utilize fatty acids in a manner that affects bacterial phenotype. The modifications to such bacteria include those effective in enhancing the beneficial traits of such bacteria for a person's skin and the reduction of respective virulence factors of the bacteria. In such a manner, one aspect of the present invention is to maintain a microbiome in a healthy, balanced state and/or returning a microbiome to a balanced state by providing certain desirable microorganisms with sufficient nutrients to thrive, and thereby outcompete and/or kill the undesirable bacteria. It has been found that *Corynebacterium jeikeium* ("*C. jeikeium*"), *Staphylococcus epidermidis* ("*S. epidermidis*"), and *Propionibacterium acnes* ("*P. acnes*"), present on both the face and forearms of humans, can be used to address dry skin conditions and diseases on such tissues. Modifications of virulence factors of pathogenic bacteria associated with such conditions, as well as combining such modified bacteria with other commensal microorganisms, is one aspect of the present invention. Such bacteria include: Alpha proteobacteria, Beta proteobacteria, Gamma proteobacteria, Propionibacteria, Corynebacteria, Actinobacteria, Clostridiales, Lactobacillales, *Staphylococcus, Bacillus, Micrococcus, Streptococcus*, Bacteroidales, Flavobacteriales, *Enterococcus*, and *Pseudomonas*.

One particular aspect of the present invention is directed to a method and system for reducing the likelihood that one will acquire multiple sclerosis (MS). To avoid such disease, the avoidance of a skin contacting soluble toxin is achieved by establishing a population of beneficial bacteria, as described herein, on a person's skin, such that *Clostridium perfringens*, a gram positive, spore forming anaerobe, which produces the toxin required for the initiation of MS, is avoided. Certain aspects of the present invention are directed to a system and method to protect a person from getting MS and/or to treat a person that has multiple sclerosis by interfering with epsilon toxin (ETX) of *Clostridium perfringens* type B or type D by interfering with the ETX interacting receptor, and in particular, by employing CRISPR-Cas and/or Cpf1 systems to modify bacteria in a manner to reduce the ability of *Clostridium perfringens* to produce effective toxins that can trigger MS. Use of CRISPR-Cas systems to provide inhibitors of such toxin, such as the inclusion of genes that express antibodies thereto, is one embodiment of the present invention. Competitive inhibition of *Clostridium perfringens* by using an effective amount of a probiotic supplement which contains a bacterial strain that outcompetes such non-modified species, is one way to provide a treatment regimen, and one of skill in the art will appreciate the many desirable strains by which to accomplish this objective, including but not limited to the following: *Lactobacillus acidophilus, L. bulgaricus, L. casie, L. fermentum, L. plantarum, Rhodopseudomonas palustris, Saccharomyces cerevisiae*, and *Streptococcus thermophiles*. To render such competitive inhibition effective, it is suggested that in preferred embodiments, a course of antibiotics is taken first to reduce the numbers of *C. perfringens*, preferably employing one or more of penicillin, ampicillin, amoxicillin, metronidazole, erythromycin, and tylosin, prior to inoculation (for some skin application, rubbing of a lotion or gel on one's skin) of the person's microbiome with one or more of the probiotic bacteria listed herein, and in particular, those bacteria modified by the CRISPR-Cas and/or Cpf1 systems described herein.

Various embodiments of the present invention are directed to a method for reducing the likelihood of the onset of a disease by administering to a subject a therapeutically effective amount of a composition comprising a probiotic microorganism, rather than attempting to alter the eurcaryotic genome of the individual. It is believed that by merely modifying a person's microbiome, whether it be their gut, oral or skin microbiome, it is possible to treat, if not protect such individuals from a vast array of previously devastating diseases of man. For example, *Helicobacter* species have been associated with enhanced carcinogenesis including liver cancer, colon cancer, and mammary carcinoma. Probiotic formulations containing lactic acid bacteria have been shown to reduce the incidence of chemically mediated hepatocellular carcinoma and colon cancer. Bacteria that have been modified using a CRISPR-Cas system to purposefully excise or interfere with virulence factors of particular pathogenic bacteria, and the employment of such modified bacteria to adjust the population of a person's microbiome, is an effective way to treat a vast number of historically difficult diseases.

Certain aspects of the present invention are directed to modifying a person's intestinal, oral or skin microbiota using specific combinations of prebiotics, pro-biotics and/or antibiotics to establish a defined microbiota that can treat and/or reduce the likelihood that individuals will experience various diseases. For example, various embodiments of the present invention are directed to averting or reducing the likelihood of cancer by employing bacteria modified to address p53 deficiency. In such a manner, rather than treating human cells and the consequent issues surrounding genetic manipulation of human cells for treatments of cancer, the present invention provides a method and system that employs the microbiome of a person, whether than be oral, gut or skin, or a combination thereof, to treat cancer by increasing the level of p53 to take advantage of the role of such protein in the progression of various cancers. Provision of modified bacteria as described herein to pre-treat a person prior to a cancer treatment, such as radiation, can also be used to lessen the otherwise detrimental effects of the radiation treatment. Moreover, after such treatments, provision of such modified bacteria to restore the person's microbiomes, whether they be oral, skin or intestinal, is one aspect of the present invention. Use of modified skin bacteria to treat melanoma is one aspect of the present invention, thus providing a way to treat skin cancer by providing essential compounds to reduce the spread and health of cancer cells while at the same time, enhancing the growth and propagation of beneficial bacteria, especially those modified as described herein via a CRISPR system.

The balance between health and disease is imperiled by infections. When immunity is lowered, the human body is less able to eradicate cancer cells, which would otherwise be kept in check. In certain embodiments, a mushroom component is also employed to achieve desired health effects. For example, in various embodiments, the mushroom mycelium is used to protect against viruses that cause disease in humans, such as those mushrooms derived or obtained from *Antrodia, Fomes, Fomitopsis, Ganoderma, Inonotus, Schizophyllum, Phellinus, Piptoporus, Trametes* and other taxa in the Polyporaceae. Ethyl alcohol/water extraction techniques are employed on living mycelium to obtain antiviral compounds and that are effective to reduce viruses that cause inflammation and immune deactivation which are contributory to oncogenesis. Such extracts reduce the pathogenicity of viruses and by doing so, reduce cancer risk and also significantly enhance the benefits of other anticancer drugs to increase the quality of life of cancer patients. Used in combination with the various other aspects of the present invention, including the beneficial modified bacterial species as described herein, a person's overall health is improved by reducing the chances of infection, inflammation and cancer, by improving and adjusting the microbiome of individuals and by having certain mushroom derived compounds administered, (some of which can be inserted into the genome of bacteria via the CRISPR-Cas system) such that beneficial compounds are administered to individuals to prevent and treat various diseases, such as but not limited to, cancer.

In particular embodiments, a method of the present invention involves a method of improving the health of a person's skin microbiome by identifying a skin region to be treated in terms of age, ethnicity, region of the body and age of the person and then applying a skin commensal prebiotic agent adapted to address the skin region; wherein the prebiotic comprises at least one microbe that has been modified by a CRISPR-Cas or Cpf1 system to add or delete a gene that enhances the health of a person's skin.

Other embodiments include a method of improving the health of a person's skin microbiome, comprising: providing a first type of bacteria to a person's skin that produces an agent that another second bacterial species requires for growth; after applying said first bacteria to the skin of a person, then applying the second bacteria to the person's skin, wherein both the first and the second bacteria comprise at least one microbe that has been modified by a CRISPR-Cas or Cpf1 system to add or delete a gene that enhances the health of a person's skin. In still others, the virulence factor of the first bacteria is modified via CRISPR-Cas to impede the interaction of bacterial adhesions and keratinocyte receptors. One can modify the expression of at least one gene by employing a CRISPR-Cas system to decrease the pathogenesis of a skin infection. Moreover, one can employ a second bacteria whose growth on a person's skin is enhanced by at least 2-fold when in the presence of the first bacteria, wherein the second bacteria is modified via CRISPR-Cas to have an essential growth required component deleted from its genome, and wherein the first bacteria has been modified via CRIPSR-Cas to add the same essential growth component that the second bacteria requires for growth.

Existing antibiotic therapies non-specifically kill the majority of skin-residing bacteria, disrupting the homeostasis of skin resident microflora. For example, benzoyl peroxide (BPO) is one of the most frequently used topical medications. BPO strongly suppresses the growth of *S. epidermidis*. *S. epidermidis* contributes to the skin resident microflora-based defense of the skin epithelium. The imbalance of microflora is believed by the present inventor to contribute to the pathogenesis of skin inflammatory diseases, such as atopic dermatitis, rosacea and acne *vulgaris* etc. Thus, in various embodiments, such antibiotic therapies are not employed but instead, beneficial bacteria are administered to a person's skin in a manner that beneficial results are achieved (e.g. reduction in malodors, generation of desired odors by bacterial production of scents, etc.) CRISPR-Cas systems are preferably employed to modify species of bacteria already found on an individual's skin such that the disturbance of the "normal" population of a particular person is not disturbed in a fashion that could lead to disease or discomfort.

Various embodiments include providing two or more bacteria species that are normally found on a person's skin, and modifying the same to remove virulence factors via CRISPR; including in such bacteria beneficial genes for the production of emollients, lipids, scents, etc. and using competitive inhibition to foster the growth of bacteria purposefully exposed to the skin surface so that pathogenic bacteria are not permitted to establish and grow. In certain embodiment, CRISPR is employed to insert a gene for the production of tomatidine in a bacteria such that, especially, in the gut microbiome, but preferably also in the oral and skin microbiome, tomatidine is expressed. Tomatidine has the effect of increasing and enhancing muscle performance and in maintaining the weight, especially muscle mass, of an individual.

*Staphylococcus aureus* is the most pathogenic species of the *Staphylococcus* genus, responsible for food poisoning, suppurative localized infections and physical septicemia (graft, cardiac prostheses). Ogston (1881) coined the genus *Staphylococcus* to describe grapelike clusters of bacteria (staphylogrape, Gr.) recovered in pus from surgical abscesses. The species proves to be an opportunistic pathogen in certain locations or under certain circumstances and is found in the commensal flora (in 15% to 30% of healthy individuals in the nasal fossae). *S. aureus* has pathogenic capacities, in particular an invasive capacity, a capacity to multiply and to spread in the organism, and also a toxic capacity. *S. aureus* has a great capacity for developing antibiotic-resistant mutants. In one embodiment, modified *Staphylococcus epidermidis* is used to produce enhanced amounts of anti-microbial peptides that inhibit *S. aureus* biofilm formation, with preferred embodiments employing CRISPR-Cas systems to achieve such modifications.

In various embodiments, due to the inclusion of bacteria-hostile formulations in over-the-counter lotions and related products, the use of conventional lotions is not suggested for employment in conjunction with the administration of many embodiments of the present invention. Lotions presently available are believed to be counterproductive to the fostering the beneficial growth of beneficial bacteria on a person's skin. E.g. salicylic acid is bacteriostatic that limits the growth of bacteria by interfering with bacterial protein production by down regulating fitness and virulence factor production of bacteria. As it is known that gram positive and gram negative bacteria prefer slightly basic conditions pH 7.5 and warm temperatures 37 degrees Celsius (98.6 degrees Fahrenheit), the establishment and maintenance of slightly acidic conditions on one's skin is a preferred objective and is achieved by the fostering of certain bacteria that produce lactic acid on a person's skin.

All gram negative bacteria are disease producing. As such, one aspect of the present invention is directed to reducing the number of gram negative bacteria on a person's skin by adjusting the overall local pH of the skin tissue region by providing bacterial species that are selected to synergistically grow together and establish a desired pH level that discourages the growth of gram negative bacteria on the skin. Caution is called for, however, as the pH should not get too low, as fungi, yeast, and molds prefer acid conditions (pH 5.5-6) at room temperature to multiply. In this regard, the pH is preferably maintained, either by bacterial species producing lactic acid at amounts sufficient to achieve such levels, or by other pH adjustment methods, in order to hinder the growth and progression of pyogenic cocci, spherical bacteria that cause various suppurative (pus-producing) infections. Included are the Gram-positive cocci *Staphylococcus aureus, Streptococcus pyogenes* and *Streptococcus pneumoniae*, and the Gram-negative cocci, *Neisseria gonorrhoeae* and *N. meningitidis*. In terms of their phylogeny, physiology and genetics, these genera of bacteria are unrelated to one another. They share a common ecology, however, as parasites of humans. The Gram-positive cocci are the leading pathogens of humans. It is estimated that they produce at least a third of all the bacterial infections of humans, including strep throat, pneumonia, otitis media, meningitis, food poisoning, various skin diseases and severe types of septic shock. The Gram-negative cocci, notably the neisseriae, cause gonorrhea and meningococcal meningitis. Again, the reduction of virulence factors of such bacteria via CRISPR-Cas or Cpf1 systems reduces the incidence of infections caused by such bacteria and leads to methods and systems for establishing and maintaining a healthy skin microbiome, free of disease.

In yet other embodiments, bacteria are modified to express certain compounds that deter mosquitoes from alighting on an individual's skin. In certain embodiments bacteria are modified to produce amounts of DEET, with such bacteria being contacted to an individual's skin. In still other embodiments other known insect repellents such as eucalyptol, linalool, and thujone, are expressed by such bacteria to deter insects. In still other embodiments, bacteria are modified to express a protein member of the ionotropic receptor family, IR40a, which is a DEET receptor. In addition, other repellent proteins structurally related to DEET may be employed to repel insects, such as mosquitoes and flies.

One aspect of various embodiments is directed to the expression of particular phytochemicals by CRISPR-Cas modified bacteria to ameliorate a human disease. Phytochemicals exert their antibacterial activity through different mechanisms of action, such as damage to the bacterial membrane and suppression of virulence factors, including inhibition of the activity of enzymes and toxins, and bacterial biofilm formation. These antibacterial effects of phytochemicals may be due to the presence of one or more of alkaloids, sulfur-containing phytochemicals, terpenoids, and polyphenols and also may involve a synergistic effect when used in combination with conventional antibiotics, thus modifying antibiotic resistance.

Still other aspects of the present invention are directed specifically to the skin of an individual's scalp, and more particularly with the treatment of dandruff. Dandruff is an unpleasant scalp disorder common to human populations. Dandruff is a common scalp disorder that has occurred for centuries and has a prevalence of nearly 50% in the worldwide population. The formation of dandruff has been studied for decades, but no coincident view has been widely accepted. The scalp is covered with pilosebaceous units and sweat glands. Human sebum is a complex mixture of triglycerides, squalene, cholesterol esters, wax esters and cholesterols that are secreted from the scalp. The secretion of sebum is controlled by sebaceous gland activity and the sebum secretion rate increases throughout a person's teenage years, reaches the highest in the 15- to 35-year-olds and appears to decline in older adults. Throughout the active period of sebum secretion, the secretion rate is higher in males than in females.

Sebum quantity and water content are negatively correlated with the formation of dandruff. Moreover, a significant relationship exists between two reciprocally inhibited bacteria, *Propionibacterium* and *Staphylococcus*, on the scalp of individuals. Thus, one aspect of the present invention relates to the adjustment of the balance of certain bacteria on an individual's scalp, and specifically, the enhancement of *Propionibacterium* and suppression of *Staphylococcus*, to leads to a reduction in dandruff. The host physiological conditions affect the microbial flora living on the scalp by affecting the scalp microenvironment. Sebum is an important food source for the growth of scalp bacteria and as saturated fatty acids in sebum are consumed, unsaturated fatty acids are left on the skin. *Staphylococcus* populations on a person's scalp indicate a significant positive correlation with dandruff, while *Propionibacterium* and *Labrys* show a significant negative correlation with dandruff. Dandruff is therefore associated with the balance of these two genera. *Propionibacterium* is affected by various conditions, including sebum and water content and tends to exist on the side scalp region on the scalps of men. *Staphylococcus* is present at a higher ratio on the top region of the scalp and is negatively associated with the water content. *Propionibacterium* can secrete bacteriocins to suppress the growth of *Staphylococcus*, whereas *Staphylococcus* can mediate the fermentation of glycerol and inhibit the overgrowth of *Propionibacterium*. Compared with a normal scalp, the dandruff region had decreased *Propionibacterium* and increased *Staphylococcus*. Thus, the balance between *Propionibacterium* and *Staphylococcus* is important to the severity of dandruff. Scalp sebum acts as a food source for *Propionibacterium*, and a high water content provides a suitable environment for *Propionibacterium* growth. Adjusting the equilibrium of the bacteria, particularly by increasing the *Propionibacterium* and decreasing the *Staphylococcus* on the scalp, lessens the severity of dandruff. Regulating the physiological conditions is therefore important to inhibit the development of dandruff.

Other aspects are directed to adjusting the type and amount of bacteria on a person's body, and in particular in the underarm region, so that malodor issues can be addressed. In one embodiment, a deodorant composition includes a mixture of bacteria selected to reduce axillary odor, and specifically involve the promotion of the growth of

*Staphylococcus epidermidis* bacteria, and the inhibition of the growth of *Corynebacterium striatum* bacteria.

Further embodiments of the invention are directed to the employment of fungi agents in treating skin conditions. One of the least studied biochemical-chemical systems in nature is the relationship existing between microorganisms and their plant hosts. Two endophytic fungi, *Muscodor albus* from *Cinnamomum zeylanicum* and *M. roseus* produce a mixture of volatile antimicrobials that effectively inhibit and kill a wide spectrum of fungi and bacteria. In certain embodiments of the present invention, the above fungi and/or the genes providing for their anti-bacterial characteristics, are employed as part of a skin microbiome agent such that particularly undesired bacteria that might otherwise thrive on an individual's skin, will be killed or reduced in population.

As depicted in FIG. 13, *L. crispatus* can be employed in various bacterial formulations to enhance the health of an individual's skin. Preferably, *L. crispatus* is included with amounts of other ingredients, including at least one of probiotics, prebiotics, and other skin-beneficial ingredients. In certain embodiments, at least one, but often at least two of *L. reuteri* and/or *L. johnsonii* and *L. crispatus* are used in a beneficial bacterial composition for topical administration, with the objective being to generate desired amounts of metabolites sufficient to reduce inflammation, especially through the production of tryptophan metabolites, believed to act as AHR agonists. In one embodiment, live bacterial cells of *Lactobacillus crispatus* are administered to the surface of an individual's skin at a dosage of at least $10^8$ CFU to reduce inflammation through the localized production of tryptophan metabolites. Preferably the skin formulation also includes glycogen and a stimulant for the production of ceramide. The metabolites produced by the *L. crispatus* applied to the kin include indole-3-acetic acid, IAld, Indole-3-Ethanol, Indole-3-pyruvate, and indole-3-aldehyde. Thus, the localized production of tryptophan-derived bacterial metabolites reduces the amount of inflammation the individual would otherwise experience. Preferred topical formulations include a combination of live *L. crispatus*, prebiotic glycogen, and at least one barrier-enhancing/moisturizing compound. In certain embodiments *L. crispatus* is combined with Human milk human milk glycans to facilitate the generation of beneficial tryptophan metabolites.

In still other embodiments, bacteria are selected for application to an individual's skin in accordance with an individual's microbiome chronobiology, thereby providing a novel therapeutic approach to treating adverse skin diseases and conditions. Certain aspects of the present invention are therefore focused on conditions and/or diseases induced by circadian clock disruption that can be mediated by adjusting an individual's microbiome composition and function. Thus, the timing of application of microbiota-based therapeutics, such as pre-, pro-, and post-biotics, is employed to advance the efficacies of treatments as described herein. An individual's microbial circadian rhythms, due to its diurnal variation, is taken into account when administering the type of bacterial formulations to a person's skin to arrive at preferred therapeutic responses. This timing of microbiota-based therapeutics provides a unique method for addressing skin conditions and diseases in a fashion previously unappreciated by those of skill in the art, thus permitting the correction of previously unaddressed dysregulation of an individual's circadian rhythm associated with aging or chronic illnesses, paying attention to such modifications in terms of the diurnally shifting microbiome. Thus, in one embodiment, a skin formulation containing *L. crispatus* is applied to an individual's skin (e.g. face tissue) at night so that it remains thereon during the sleeping pattern of the individual. The benefits to the individual's skin due to such a "night mask" includes the reduction of inflammation that would otherwise be observed on the skin. For example, as an acne treatment, application of a *L. crispatus* formulation as described herein during sleep, especially when combined with a glycogen in an amount sufficient to sustain the *L. crispatus* for at least one hour after application to an individual's skin, results in a noticeable reduction in the inflammation that would otherwise occur due to the acne.

In various other and related embodiments, bacterial formulations as described herein are employed to reduce or prevent the progression of at least one of scarring (e.g., scar relating to sunburn, bed sore, wound, inflammatory lesion, or burn), crack, fissure, heloma, sebum secretion, skin thickening, wrinkle, sun spot, skin tag, keloid scar, dark patch, stretch mark, spider vein, varicose vein, age spot, cellulitis, or pore appearance in an individual. Still other embodiments focus on the amount and/or a frequency of administration that is sufficient to reduce or prevent the progression of blotchiness or discoloration (e.g., vitiligo or post-inflammatory hyperpigmentation) associated with skin of an individual. Others relate to the amount and/or a frequency of administration sufficient to promote firmness, elasticity, radiance, tone evenness, visual smoothness, hydration, or tactile smoothness associated with skin, such as to reduce or prevent the progression of a wrinkles, fine lines, or deep furrows. Formulations can be prepared to include, in combination, a moisturizer, sunscreen, wrinkle cream, retinoid, alpha-hydroxy acid, antioxidant, tretinoin, glycosaminoglycan (GAG), lactic acid, malic acid, citric acid, tartaric acid, hydroquinone, kojic acid, L-ascorbic acid, licorice extract, N-acetylglucosamine, niacinamide, soy, dermal filler, hyaluronic acid or calcium hydroxylapatite, botulinum toxin, laser resurfacing procedure, ultrasound therapy, chemical peel, glycolic acid peel, trichloroacetic acid, salicylic acid. Some formulations are administered in conjunction with nitrite, nitrate, and/or NO.

Thus, one of skill in the art will appreciate that using the bacterial formulations set forth herein, one can practice a method for reducing the likelihood of a skin condition that causes skin inflammation, by providing a bacterial formulation that includes at least one of a live bacteria selected from the group consisting of *L. reuteri, L. johnsonii* and *L. crispatus*, preferably where the bacterial formulation includes at least one prebiotic having glycogen as a component thereof. The skin condition may be, for example, eczema, atopic dermatitis, acne, allergic inflammation, and skin hypersensitivity. The formulation may also be administered to an individual's skin as a probiotic bacteriotherapy to treat ultra-violet-induced skin damage.

The bacterial formulation is administered to an individual's skin in an amount sufficient for the bacterial formulation to generate an amount of tryptophan metabolites so as to act as an aryl hydrocarbon receptor (AHR) agonist, thereby reducing inflammation on the individual's skin. The bacterial formulation preferably includes *L. crispatus* and at least one of a probiotic, prebiotic, and a skin moisturizer and also preferably includes live bacterial cells at a dosage of at least $10^8$ CFU. Certain embodiments include in the bacterial formulation a stimulant for the production of ceramide. The bacterial formulation is designed to generate tryptophan metabolites, such as indole-3-acetic acid, IAld, Indole-3-Ethanol, Indole-3-pyruvate, and indole-3-aldehyde. In certain embodiments, the bacterial formulation is applied to an individual's skin at night so that it remains thereon during the sleeping pattern of the individual. Moreover, certain embodiments include glycogen in an amount sufficient to sustain the bacteria, preferably *L. crispatus*, for at least one hour after application to an individual's skin. In most cases there is a localized production of tryptophan-derived bacterial metabolites by the bacterial formulation that reduces the amount of inflammation the individual would otherwise experience. Formulations may include, e.g. a combination of live *L. crispatus*, prebiotic glycogen, and at least one barrier-enhancing/moisturizing compound. Some bacterial formulations include human milk human milk glycans in an amount sufficient for the bacteria to generate tryptophan metabolites. In yet other embodiments, the methods involve the employment of a bacterial formulation that also includes a therapeutically effective amount of a bacterial formulation comprising *Nitrosomonas eutropha*, preferably provided in the form of a lotion, ointment or gel adapted to be rubbed onto a region of an individual's skin. One may further administer to the individual's skin a prebiotic that includes a nutrient source for the bacteria in the bacterial formulation that is assimilated by the bacteria. Certain bacterial formulations also include *Propionibacterium* bacteria, with others including arabinogalactan, or a glycan unit selected from the group consisting of a glucose, a galactose, an arabinose, a mannose, a fructose, a xylose, a fucose, and a rhamnose. Still other methods involve administering to the skin an extract derived from a helminth selected from the group consisting of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus*, and *Trichinella spiralis*. A particular method for reducing the likelihood of a skin condition that causes skin inflammation in an individual human being is directed to the administration of a therapeutically effective amount of a bacterial formulation comprising at least one of a live bacteria selected from the group consisting of *L. reuteri, L. johnsonii* and *L. crispatus*, and *Nitrosomonas eutropha*. wherein at least some bacteria in the bacterial formulation have been modified by using a using a clustered regularly interspaced short palindromic repeats (CRISPR) CRISPR associated protein (Cas) system or a CRISPR from *Prevotella* and *Francisella* 1 (Cpf1) system to enhance the generation of a tryptophan metabolite.

*C. acnes* strains are capable of producing several virulence factors that increase inflammatory capability. This pathogenic property is believed to be related to infectious mechanisms, such as an ability to form biofilms and the expression of putative virulence factors capable of triggering host immune responses or enabling *C. acnes* to adapt to its environment.

Thus, virulence factors potentially involved in the pathogenicity of this bacterium are involved in bacterial attachment to target cells, polysaccharide-based biofilm synthesis, molecular structures mediating inflammation, and the enzymatic degradation of host tissues. It produces several proteins or glycoproteins considered to be active virulence factors, enabling the bacterium to adapt to the lipophilic environment of the pilosebaceous unit of the skin, as well as various organs it colonizes. *C. acnes* is also involved in the maintenance of healthy skin but can act as an opportunistic pathogen in various inflammatory conditions, including acne.

*C. acnes* is the most abundant bacterium in the skin microbiota, and its load does not seem to differ between healthy skin and skin affected by acne. One aspect of the present invention is directed to the belief that inflammatory acne is triggered by an imbalance in the skin microbiota associated with the selection of specific types of *C. acnes*. *C. acnes* induces a significant production of reactive oxygen species (ROS) by keratinocytes, mediated by the cytoplasmic NADPH oxidase. The various phylotypes of *C. acnes* have different inflammatory potentials and express different putative virulence factors. *C. acnes* is an opportunistic pathogen of low pathogenicity is mediated by several molecular mechanisms, including the production of biofilms and the expression of virulence factors triggering immune responses in the host. Virulence factor genes have been identified in the *C. acnes* genome, with some involved in cell adhesion, whereas others mediate inflammation, tissue invasion/degradation in the host, and the synthesis of capsule polysaccharides. These putative virulence factor genes encode sialidases, neuraminidases, endoglycoceramidases, adhesins, thermal shock proteins, CAMP factors, lipases/esterases, and lipases. Other genes of *C. acnes* encode virulence factors, such as adhesin dermatan-sulfate (DsA1 and DsA2), CAMP factors, polyunsaturated fatty acid isomerase, HtaA iron acquisition protein and GehA lipase, and heat shock proteins.

Christie-Atkins-Munch-Petersen (CAMP) factors are toxin proteins that form pores in host membranes, leading to host tissue damage. *C. acnes* has at least five CAMP factor genes, CAMP1 to CAMP5. Certain aspects of the present invention are directed to the interaction of *C. acnes* with the skin microbiota has with respect to its influence on its pathogenicity. In certain embodiments the use of *C. acnes* strains is as a probiotic option to treat skin disorders.

CAMP1 can trigger an innate immune response when *C. acnes* comes in close contact with human (immunocompetent) cells, but such CAMP factors, due to their pore-forming activity, are believed to be involved in accessing nutrients within the sebaceous follicle microenvironment, without causing excessive damage to intact keratinocytes.

One aspect of certain embodiments of the present invention is directed to enhancing the production by *C. acnes* to produce short-chain fatty acids as metabolites, including propionate, acetate, butyrate and valerate. Such SCFA production by *C. acnes* suppresses the growth of *S. aureus* and therefore prevents the colonization of *S. aureus* on the skin. Such production of SFCAs produced by *C. acnes* also inhibits biofilm formation by *S. epidermidis*. Thus, there while there are both health-beneficial as well as -detrimental roles of *C. acnes*-produced SFCAs, it is believed that a particular balance of the amount and the type of SFCAs produced is determinative of such benefits and detriments. In one particular embodiment of the present invention, *C. acnes* is modified via a CRISPR system to produce predominantly butyrate to achieve beneficial skin conditions.

In still other embodiments, CRISPR systems are employed to modify *C. acnes* to produce increased levels of porphyrins so as to affect other members of the skin microbiome.

*C. acnes* in some embodiments is therefore employed to limit colonization by more potent pathogens and to positively maintain redox homeostasis on the skin. Despite its past reputation as being a skin pathogen, *C. acnes* in certain aspects of the present invention is a beneficial skin bacterium that fulfills important roles for skin homeostasis and protection.

In certain embodiments, the present invention is directed to the use of *Janthinobacterium*, and particularly a modified strain that, via a CRISPR system, is modified to reduce or eliminate the presence of at least one virulence factor of the wild type strains, e.g. vioABCDE violacein, flok formation, and strong biofilm, and type VI secretion system (T6SS). In one embodiment, a method is provided for treating a skin disorder in a subject in need thereof, that comprises topically administering a formulation comprising an effective amount of probiotic bacteria, a metabolite of probiotic bacteria, and/or a cell lysate of probiotic bacteria, wherein the probiotic bacteria are human-derived *Janthinobacterium lividum*; and the disorder is associated with the presence of a topical pathogenic microorganism. *Janthinobacterium* sp. contain genes as virulence factors.

Certain embodiments of the present invention are directed to a method to topically administer a composition of probiotic strains of bacteria, post-biotic metabolites, or other skin-specific compounds to modulate, restore, and/or support a healthy or normal skin microbiome and skin barrier microenvironment, defined as populational normal skin barrier function, tight junction maintenance, skin hydration defined as filaggrin production and degradation into sufficient levels of natural moisturizing factor (NMF) (defined as >1.50 mmol/g protein), Pyrrolidone Carboxylic Acid (PCA) (defined as >1 mmol/g protein), urocanic acid (UCA) (defined as >0.2 mmol/g protein), and histidine (HIS) (defined as >0.08 mmol/g protein), low or no colonization of pathogenic bacteria, fungi, and other microorganisms (defined as but not limited to *Malassezia* spp, *P. acnes, S. aureus, Klebsiella pneumoniae, Mycobacterium tuberculosis, Streptococcus pyogenes*), colonization of beneficial bacteria, and non-visible normal levels of inflammation and immune activity that cannot be visually identified as inflamed, scaly, boils, or damaged skin. Overall, the described optimal skin microenvironment otherwise characterized as a microenvironment that does not exhibit clinical representations or symptoms of disruption, including manifestations of atopic dermatitis, psoriasis, ichthyosis, acne, vitiligo, *Tinea versicolor*, and seborrheic dermatitis.

Various embodiments are directed to compositions of at least two probiotic strains and/or post-biotics administered in the concentration of at least 1×108 via AFU counting as either live or heat-killed combinations representative of genomic diversity found in healthy skin microbiomes that are resistant to pathogen colonization, including bacteria selected from the group consisting of *Cutibacterium, Staphylococcus, Corynebacterium*, and *Micrococcus* spp. and other Actinobacteria, Proteobacteria, and Firmicutes. The presence of multiple diverse strains is believed to suppress expression of virulence factors and modulate metabolism on a population-level and thus, various embodiments are directed to achieving strain diversity in such compositions so as to provide and enable the suppression of *S. epidermidis*' potential transition to pathogenicity.

Certain acne-associated strains produce higher levels of porphyrins which can be regulated by the availability of vitamin B12. Certain *S. epidermidis* strains produce varying amounts of metabolites of the riboflavin biosynthesis pathway that mediate mucosa-associated invariant T (MAIT) cell activation. Thus, certain aspects of the present invention are directed to modifying strains of such bacteria, preferably via CRISPR systems, to affect the regulation of porphyrin production and/or to regulate MAIT cell activation. Still other embodiments are directed selecting or generating strains of *C. acnes* that produce cutimycin, an antimicrobial that reduces the presence of *S. epidermidis*, in order to alter the ratio of *Cutibacterium:Staphylococcus* in order to treat skin cancer and conditions affecting the aging of skin.

Certain embodiments are directed to providing compositions of at least two probiotic strains and/or post-biotics administered in the concentration of at least 1×108 via AFU counting as either live or heat-killed to regulate an individual's skin microbiome ecology by utilizing sebum without producing proinflammatory metabolites or byproducts. Other embodiments focus on compositions of at least one probiotic strain that produces lipases that break down sebum lipids into fatty acids and thus, acidify the surface of the skin. Still other embodiments are directed to compositions where at least two probiotic strains and/or post biotics are provided that possess broad anti-inflammatory activity, preferably employing strains, preferably modified via CRISPR systems, to have reduced proinflammatory responses on an individual's skin. Certain compositions of various embodiments include at least one probiotic strain that is protective to tight junction proteins, thus preserving desired attributes of an individual's skin barrier. While certain embodiments involve the use of diverse strains, some other embodiments are focused on the employment of compositions consisting of single strains that do not upregulate innate immune response genes, such as CXCL1, CXCL3, CXCL8, CXCL10. In other embodiments such strains do not upregulate other innate immune response genes, including the following: IL10RA, PTGS2, F2RL1, TRIM29, TRAF4, LGALS3, CD55, TRIM8, CASP4, IFNGR1, ADA, NOD1, NOS2, APP, e.g. at 1:10,000 dilutions. Still other embodiments are directed to compositions including one or more strains that down-regulate the above referenced pathways.

Alternative embodiments of the present invention are directed to the provision and use of compositions of single strains or multi strain ecologies administered as live or heat-killed post-biotic applications in at least AFU defined concentrations of 1×108 cells that do not upregulate cytokine genes including the epithelial alarmin TSLP, and CCL20, VEGFA, IL18, and IL23A, with still other embodiments directed to the down-regulation of these pathways. Certain compositions include at least one probiotic strain that regulates filaggrin protein expression and/or degradation in a manner such that an individual's skin moisture is modified and thus, associated methods permit the regulation of an individual's skin moisture via the provision of a composition of selected strains where filaggrin expression is altered as compared to wild type strains. Loss of filaggrin results in dry skin and skin inflammation with type 3 immune responses. Thus, certain embodiments are directed to increasing the production of filaggrin to avoid the development of dry skin. Included within the group of compositions of the present invention are those that include at least one probiotic strain in combination with medium chain triglycerides and/or fatty acids in order to inhibit fungal growth and/or biofilm formation, specifically of the genus *Malassezia*.

In certain embodiments, in addition to the provision of beneficial strains as described herein, compositions and formulations include postbiotic metabolites, preferably fatty acids produced from sebum metabolism by *Cutibacterium*. Such compositions are topically applied to skin in order to regulate inflammatory activities of other bacteria found on an individual's skin, to regulate skin pH to inhibit pathogens, and/or to regulate skin moisture, hydration, and barrier properties. Certain embodiments include not only the strains as described herein, but also formulations that include compounds, lipids, proteins, and nutrients found in cellular debris and that are purified. Preferred embodiments include compounds that are able to cleave sebum triglycerides so as to free glycerol, such as strains that secrete an extracellular lipase that cleaves sebum triglycerides, thus freeing glycerol. The acidification of an individual's employing the strains and compound formulations as described herein are employed to reduce or prevent the colonization by pathogenic microbes. Other embodiments are directed to the use of at least one probiotic strain, preferably modified using a CRISPR system, to induce the anti-inflammatory cytokine IL-10 on an individual's skin. As one of skill in the art will appreciate, various compositions of the present invention may contain one of live, heat killed, or post-biotic skin applications of coagulase-negative *Staphylococcus* (CoNS) species, e.g. *S. epidermidis, S. capitis, S. caprae, S. hominis, S. lugdunensis*, and *S. haemolyticus*, that are able to reduce the abundance of *S. aureus* on an individual's skin.

Certain embodiments are directed to the modification of *C. acnes* to increase the production of propionic acid, which is believed to assist in the maintenance of the acidic pH of healthy skin. Thus, provision of modified *C. acnes*, either via selective propagation or CRISPR technology, that has increased production of propionic acid (as compared to wild type strains) is employed to inhibit the colonization of an individual's skin by pathogenic microbes.

Certain embodiments of the present invention are directed to administering a composition topically to an individual's skin that includes live or heat-killed coagulase-negative *Staphylococcus* (CoNS) species at the AFU determined concentration of at least $1 \times 10^8$ cells, which are gram-positive, facultative anaerobes, and that is able to inhibit certain pathogenic bacteria, such as *S. aureus* strains that are coagulase positive, or capable of coagulating blood. Preferably the CoNS species comprise *S. epidermidis, S. capitis, S. caprae, S. hominis, S. lugdunensis*, and *S. haemolyticus*. Preferably, the species of CoNS employed is able to directly kill *S. aureus* strains on an individual's skin by secreting antimicrobial peptides, such as lantibiotics, phenol-soluble modulins (PSM), with even more preferred embodiments employing CoNS strains that have been modified via CRISPR systems to increase its selective killing capabilities and/or in combination with specific abiotic compounds such as monolaurin or lauric acid to further reduce the prevalence of the target organism.

In various embodiments, compositions are formulated to achieve optimal barrier protection in either or both a preventative and/or rescue (e.g. restorative) perspective, with preferred embodiments including a dual formulation of a cleanser and a serum. Preferably the cleanser will include a blend of at least two barrier-safe surfactants that gently cleanse the skin. Barrier- and microbiome-safe surfactants are defined as either doing no significant harm to the barrier when administered for a normal time-course of cleansing, and/or being shown to have minimal and rescue-able degradation across the same time-course and showing no long-term negative effects on microbiome composition. In addition, preferred blends of surfactants are included in a formulation that has a concentration so as to achieve desired cleaning performance without damaging the barrier. This is in contrast to a variety of typical surfactants that either cause significant disruption of the barrier during a normal time-course of treatment and/or cause damage that is incapable for being fully restored in a succinct time and/or delivered at a high enough concentration to achieve either of the first two points. In certain embodiments, in addition to the surfactant blend, the composition includes rescue compounds that provide real-time protection of the skin barrier from surfactant damage.

By way of example, certain cleanser compositions include at least two barrier- and microbiome-safe surfactants at a concentration between 5-20% of the formulation, such cleanser compositions including but not limited to: one or more of sodium methyl cocoyl taurate, sodium cocoyl glutamate, coco glucoside, caprylylicapryl glucoside, sodium cocoyl Isethionate, cetearyl alcohol. Still other cleanser compositions include at least two barrier-protective compound at a concentration of at least 1% of the formulation, such cleanser compositions including but not limited to: one or more of indole-3-carbinol, resveratrol, niacinamide, nicotinic acid, nicotinamide mononucleotide, nicotinamide riboside, quercetin, tryptophan, diiodomethane, *Lactobacillus crispatus* (live, heat killed, or postbiotic), *Boswellia serrata*, indirubin, and *Lactobacillus acidophilus* SD-NCFM-US (live, heat killed, or postbiotic).

In preferred embodiments, a rescue serum includes a unique composition of barrier-restoring compounds and also, in addition, a barrier-restoring oil component that is non-comedogenic, so as to provide a multi-modal mechanism of action able to restore the natural, healthy, resilient state of the skin barrier. In certain embodiments, the serum composition includes at least two barrier-restoring compounds at a concentration of at least 2% of the formulation, including but not limited to: indole-3-carbinol, resveratrol, niacinamide, nicotinic acid, nicotinamide mononucleotide, nicotinamide riboside, quercetin, tryptophan, diiodomethane, *Lactobacillus crispatus* (live, heat killed, or postbiotic), *Boswellia serrata*, indirubin, and *Lactobacillus acidophilus* SD-NCFM-US (live, heat killed, or postbiotic). In other embodiments, the serum composition includes at least one barrier-restoring oils of at least 5%, including but not limited to: sunflower oil, coconut oil, murumuru oil, sea buckthorn oil, sachi inchi oil, and babbasu oil.

Certain embodiments are directed to the use of skin barrier compositions. In particular embodiments, a formulation includes a probiotic, heat-killed bacteria, and/or post-biotic metabolite, in conjunction with a topically applied vitamin (such as niacinamide) or botanical extract or constituent (such as resveratrol) to support barrier function through anti-inflammatory pathways in conjunction with tight junction upregulation to normalize Transepithelial Electrical Resistance (TEER) and/or Transepidermal Water Loss (TEWL) readings as measured via a Nevisense device. TEWL is a measure of the amount of water that evaporates through the skin. TEER is a measure of the electrical resistance of a tissue or membrane, such as the skin. Both TEWL and TEER are important parameters in skin research as they reflect the integrity and barrier function of the skin. A Nevisense device is a medical instrument used for the early detection of melanoma by using Electrical Impedance Spectroscopy (EIS) technology to measure the electrical properties of skin lesions and analyze the data to determine the likelihood of the lesion being a melanoma.

Other embodiments are directed to purposefully interfering with cell-to-cell communications (e.g. quorum sensing) of *S. aureus*, with preferred embodiments targeting the accessory gene regulator (agr) system that is believed to be necessary for *S. aureus* skin infection. Thus, embodiments of the present invention are directed to providing commensal bacteria in a topical application containing at least two of the following actives that are able to kill or inhibit the growth and virulence of certain pathogenic bacteria; comprised of live bacteria at the concentration of at least $1 \times 10^8$ cells (AFU), or heat-killed bacteria at the concentration of at least $1 \times 10^8$ cells (AFU), or post-biotic compounds, or abiotic antimicrobial compounds such as monolaurin.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

It has been observed by the present inventors that producing Haiku resembles the generation of a patent claim. There is requisite structure, a need to communicate substance and an ethereal quality of understanding. As one of skill in the art of both biology and haiku will appreciate with respect to skin:

Within it we are
Without it we cannot be
Guardian for life.

The foregoing has outlined rather broadly various pertinent and important features of various embodiments of the present invention. Such description is, however, not to be considered as limiting the invention in any way. The invention is capable of other embodiments and of being practiced and carried out in various ways which will become obvious to those skilled in the art who read this specification. Also, it is to be understood that the phraseology and terminology employed herein are for the purpose of description and should not be regarded as limiting of the invention in any fashion. It is important, therefore, that the claims be regarded as including any such equivalent construction insofar as they do not depart from the spirit and scope of the present invention.

What is claimed is:

1. A method of modulating an individual's skin microbiome, comprising: administering to a region of an individual's skin who has a skin condition a therapeutically effective amount of a bacterial formulation comprising at least one bacteria selected from the group consisting of *Lactobacillus reuteri, Lactobacillus johnsonii, Janthinobacterium, Lactobacillus crispatus, Cutibacterium acnes*, and *Nitrosomonas eutropha*, said bacterial formulation comprising a lotion, ointment or gel adapted to be rubbed onto a region of the individual's skin, and abiotic augmentations comprising fatty acids, wherein said at least one bacteria comprises a heat-killed bacteria and wherein the bacterial formulation is in an amount effective to treat, inhibit or reduce a skin condition selected from the group consisting of eczema, atopic dermatitis, acne, allergic inflammation, ultra-violet-induced skin damage, and skin hypersensitivity.

2. The method as set forth in claim 1, wherein the bacterial formulation further comprises one or more of *Staphylococcus, Bifidobacterium*, and *Streptococcus*.

3. The method as set forth in claim 1, further comprising administering to the individual one of a prebiotic, a metabolite, and a postbiotic.

4. The method as set forth in claim 1, further comprising administering to the individual a cleanser composition comprising at least one of sodium methyl cocoyl taurate, sodium cocoyl glutamate, coco glucoside, caprylyl/capryl glucoside, sodium cocoyl Isethionate, and cetearyl alcohol; a serum composition comprising at least two of the following: indole-3-carbinol, resveratrol, niacinamide, nicotinic acid, nicotinamide mononucleotide, nicotinamide riboside, quercetin, tryptophan, diiodomethane, *Boswellia serrata*, and indirubin; and at least one barrier-restoring oil comprising at least one of sunflower oil, coconut oil, murumuru oil, sea buckthorn oil, sachi inchi oil, and babbasu oil.

5. The method as set forth in claim 1, wherein at least some bacteria in the bacterial formulation have been modified by using a using a clustered regularly interspaced short palindromic repeats (CRISPR) CRISPR associated protein (Cas) system or a CRISPR from *Prevotella* and *Francisella* 1 (Cpf1) system to reduce the production of a virulence factor.

6. The method as set forth in claim 1, wherein the at least one bacteria is one of *Cutibacterium acnes* and *Janthinobacterium*.

7. The method as set forth in claim 1, wherein the at least one bacteria in the bacterial formulation produce short-chain fatty acids selected from the group consisting of propionate, acetate, butyrate and valerate.

8. The method as set forth in claim 1, wherein the at least one bacteria in the bacterial formulation does at least one of: suppress the growth of *S. aureus*; reduce the colonization of *S. aureus* on the individual's skin; and inhibit biofilm formation by *S. epidermidis*.

9. The method as set forth in claim 1, further comprising killing or retarding the growth of a pathogenic bacteria within the individual, said pathogenic bacteria selected from the group consisting of *Staphylococcus aureus; Pseudomonas aeruginosa; Klebsiella; Streptococcus; Salmonella; Shigella; Mycobacterium tuberculosis; Enterococcus; E coli; Clostridium; Neisseria gonorrhoeae; Acinetobacter baumannii*; and *Campylobacter*.

10. The method as set forth in claim 1, wherein said method further comprises enhancing the growth of a beneficial bacteria in the individual selected from the group consisting of *C. acnes, Akkermansia, Bacteroides, Bifidobacterium, Fusobacterium, Coprococcus, Lactobacillus, Propionibacterium, Nitrosomonas eutropha, Ruminococcus, Veillonella, Prevotella*, and *Streptococcus* bacteria.

11. The method as set forth in claim 1, further comprising administering at least two probiotic strains to the individual's skin in a concentration of at least $1 \times 10^8$ Arbitrary Fluorescence Units (AFU), said at least two probiotic strains being either live or heat-killed and selected from the group consisting of *Cutibacterium, Staphylococcus, Corynebacterium, Micrococcus* spp., Actinobacteria, Proteobacteria, and Firmicutes.

12. The method as set forth in claim 1, further comprising administering to the individual's skin at least one probiotic strain that does not upregulate innate immune response genes selected from the group consisting of CXCL1, CXCL3, CXCL8, CXCL10.

13. The method as set forth in claim 1, further comprising administering to the individual's skin at least one probiotic strain that does not upregulate innate immune response genes selected from the group consisting of IL10RA, PTGS2, F2RL1, TRIM29, TRAF4, LGALS3, CD55, TRIM8, CASP4, IFNGR1, ADA, NOD1, NOS2, and APP.

14. A method of modulating an individual's skin microbiome, comprising, administering to a region of an individual's skin who has a skin condition a therapeutically effective amount of a bacterial formulation comprising *Lactobacillus crispatus*, and at least two bacteria selected from the group consisting of *Lactobacillus reuteri, Lactobacillus johnsonii, Cutibacterium acnes, Janthinobacterium* and *Nitrosomonas eutropha*, said bacterial formulation comprising a lotion, ointment or gel adapted to be rubbed onto a region of the individual's skin, and abiotic augmentations comprising fatty acids, wherein the at least two bacteria comprise heat-killed bacteria and wherein the skin condition is selected from the group consisting of eczema, atopic dermatitis, acne, allergic inflammation, impetigo, ultra-violet-induced skin damage, and skin hypersensitivity.

15. The method as set forth in claim 14, wherein the skin condition is selected from the group consisting of atopic dermatitis, and wherein the individual has a skin infection associated with a topical pathogenic microorganism comprising *Staphylococcus aureus*.

16. The method as set forth in claim 14 further comprising administering to the individual a prebiotic, metabolite, and a postbiotic.

17. The method as set forth in claim 14, wherein said bacterial formulation further comprises bacteria selected from the group consisting of *Faecalibacterium prausnitzii*, *Bifidobacterium*, *Lachnospira*, *Veillonella*, *Coprococcus*, *Akkermansia muciniphila* and *Rothia*.

18. A method of modulating an individual's skin microbiome, comprising, topically administering to a region of an individual's skin a therapeutically effective amount of a bacterial formulation comprising heat-killed *Lactobacillus crispatus* bacteria, and at least one of *Lactobacillus reuteri*, *Lactobacillus johnsonii*, *Lactobacillus crispatus*, *Cutibacterium acnes*, *Bifidobacterium lognum* and *Nitrosomonas eutropha*, said bacterial formulation comprising a lotion, ointment or gel adapted to be rubbed onto a region of the individual's skin, and wherein the bacterial formulation further comprises *Janthinobacterium*.

19. The method as set forth in claim 18, further comprising administering to the individual's skin one of arabinogalactan and a UV protectant chemical.

20. The method as set forth in claim 18, wherein the bacterial formulation is administered to an individual's skin who has a skin condition in an amount sufficient for the bacterial formulation to generate an amount of tryptophan metabolites sufficient to act as aryl hydrocarbon receptor (AHR) agonists to thereby reduce inflammation on the individual's skin, wherein the skin condition is selected from the group consisting of eczema, atopic dermatitis, acne, allergic inflammation, ultra-violet-induced skin damage, and skin hypersensitivity.

* * * * *